(12) United States Patent
Berger et al.

(10) Patent No.: US 11,547,416 B2
(45) Date of Patent: Jan. 10, 2023

(54) LEFT ATRIAL APPENDAGE CLOSURE

(71) Applicant: Append Medical Ltd., Or Yehuda (IL)

(72) Inventors: Zachi Berger, Nes Ziona (IL); Oded Meiri, Moshav Ram-On (IL); Leonid Sternik, Savyon (IL)

(73) Assignee: Append Medical Ltd., Or Yehuda (IL)

( * ) Notice: Subject to any disclaimer, the term of this patent is extended or adjusted under 35 U.S.C. 154(b) by 45 days.

(21) Appl. No.: 16/497,821

(22) PCT Filed: Mar. 27, 2018

(86) PCT No.: PCT/IL2018/050353
§ 371 (c)(1),
(2) Date: Sep. 26, 2019

(87) PCT Pub. No.: WO2018/178979
PCT Pub. Date: Oct. 4, 2018

(65) Prior Publication Data
US 2020/0100796 A1 Apr. 2, 2020

Related U.S. Application Data

(60) Provisional application No. 62/476,881, filed on Mar. 27, 2017.

(51) Int. Cl.
*A61B 17/12* (2006.01)
*A61B 17/00* (2006.01)
*A61B 17/221* (2006.01)

(52) U.S. Cl.
CPC .. *A61B 17/12122* (2013.01); *A61B 17/12013* (2013.01); *A61B 17/12145* (2013.01);
(Continued)

(58) Field of Classification Search
CPC ........ A61B 17/12013; A61B 17/12145; A61B 2017/12018; A61B 2017/1205;
(Continued)

(56) References Cited

U.S. PATENT DOCUMENTS

| 7,050 A | 1/1850 | Caulkins et al. |
|---|---|---|
| 80,163 A | 7/1868 | Gorgas et al. |

(Continued)

FOREIGN PATENT DOCUMENTS

| EP | 1579823 | 9/2005 |
|---|---|---|
| WO | WO 2008/020975 | 2/2008 |

(Continued)

OTHER PUBLICATIONS

Applicant-Initiated Interview Summary dated Nov. 3, 2017 From the US Patent and Trademark Office Re. U.S. Appl. No. 14/232,573. (3 pages).

(Continued)

*Primary Examiner* — Katherine H Schwiker
*Assistant Examiner* — Raihan R Khandker

(57) ABSTRACT

A left atrium appendage (LAA) isolator, including: a body sized and shaped to fit an at least partially inverted LAA of a human adult, wherein a distal end of said body defines a two-state sealing adaptor interface configured in a first state to apply a radially outward force against a wall of said LAA or against a wall of said LAA opening sufficient to anchor said body to the LAA wall, and in a second state the sealing adaptor interface is configured to apply a radially inward force on a portion of the inverted LAA positioned within said body.

19 Claims, 43 Drawing Sheets

(52) U.S. Cl.
CPC ............ *A61B 17/12168* (2013.01); *A61B 2017/00561* (2013.01); *A61B 2017/00867* (2013.01); *A61B 2017/1205* (2013.01); *A61B 2017/12018* (2013.01); *A61B 2017/2215* (2013.01)

(58) Field of Classification Search
CPC ...... A61B 2017/2215; A61B 17/12009; A61B 17/12; A61B 17/12122; A61B 17/0057; A61B 2017/00243; A61B 2017/00561; A61B 2017/306; A61B 17/12168; A61B 17/12172
See application file for complete search history.

(56) References Cited

U.S. PATENT DOCUMENTS

| | | | |
|---|---|---|---|
| 2,235,350 | A | 3/1941 | Anderson |
| 5,224,497 | A | 7/1993 | Ehlers |
| 5,423,830 | A | 6/1995 | Schneebaum et al. |
| 5,792,153 | A | 8/1998 | Swain et al. |
| 6,152,936 | A | 11/2000 | Christy et al. |
| 6,383,198 | B1 | 5/2002 | Hamilton |
| 7,427,279 | B2 | 9/2008 | Frazier et al. |
| 8,647,367 | B2 | 2/2014 | Kassab et al. |
| 8,784,469 | B2 | 7/2014 | Kassab |
| 2001/0041914 | A1 | 11/2001 | Frazier et al. |
| 2003/0158563 | A1 | 8/2003 | McClellan et al. |
| 2005/0021016 | A1 | 1/2005 | Malecki et al. |
| 2007/0043344 | A1 | 2/2007 | McAuley |
| 2007/0083082 | A1 | 4/2007 | Kiser et al. |
| 2007/0225734 | A1 | 9/2007 | Bell et al. |
| 2008/0033241 | A1* | 2/2008 | Peh ............... A61B 1/3137 600/109 |
| 2008/0255427 | A1 | 10/2008 | Satake et al. |
| 2008/0294175 | A1 | 11/2008 | Bardsley et al. |
| 2008/0312664 | A1 | 12/2008 | Bardsley et al. |
| 2009/0326518 | A1 | 12/2009 | Rabin |
| 2010/0145361 | A1 | 6/2010 | Francischelli et al. |
| 2010/0191279 | A1 | 7/2010 | Kassab et al. |
| 2010/0312256 | A1 | 12/2010 | Kassab et al. |
| 2011/0077672 | A1 | 3/2011 | Fleischman et al. |
| 2011/0082495 | A1* | 4/2011 | Ruiz ............... A61B 17/0057 606/213 |
| 2012/0035622 | A1 | 2/2012 | Kiser et al. |
| 2014/0018831 | A1 | 1/2014 | Kassab et al. |
| 2014/0171733 | A1* | 6/2014 | Sternik ............ A61B 17/12122 600/37 |
| 2016/0106437 | A1 | 4/2016 | van der Burg et al. |
| 2017/0065283 | A9 | 3/2017 | Kassab et al. |
| 2019/0262003 | A1* | 8/2019 | Kiser ............... A61B 17/1285 |
| 2019/0321020 | A1 | 11/2019 | Sternik |

FOREIGN PATENT DOCUMENTS

| | | |
|---|---|---|
| WO | WO 2012/103556 | 8/2012 |
| WO | WO 2013/008231 | 1/2013 |
| WO | WO 2018/178979 | 10/2018 |

OTHER PUBLICATIONS

Communication Pursuant to Article 94(3) EPC dated Apr. 19, 2017 From the European Patent Office Re. Application No. 12811116.8. (9 Pages).
Communication Pursuant to Article 94(3) EPC dated Oct. 31, 2018 From the European Patent Office Re. Application No. 12811116.8. (7 Pages).
Communication Pursuant to Rules 161(2) and 162 EPC dated Feb. 27, 2014 From the European Patent Office Re. Application No. 12811116.8. (3 Pages).
International Preliminary Report on Patentability dated Oct. 10, 2019 From the International Bureau of WIPO Re. Application No. PCT/IL2018/050353. (14 Pages).
International Preliminary Report on Patentability dated Jan. 14, 2014 From the International Bureau of WIPO Re. Application No. PCT/IL2012/000278. (10 Pages).
International Search Report and the Written Opinion dated Aug. 14, 2018 From the International Searching Authority Re. Application No. PCT/IL2018/050353. (22 Pages).
International Search Report dated Nov. 11, 2012 From the International Searching Authority Re. Application No. PCT/IL2012/000278. (4 Pages).
Invitation to Pay Additional Fees, Communication Relating to the Results of the Partial International Search and the Provisional Opinion dated Jun. 20, 2018 From the International Searching Authority Re. Application No. PCT/IL2018/050353. (16 Pages).
Notice of Allowance dated Jan. 9, 2019 From the US Patent and Trademark Office Re. U.S. Appl. No. 14/232,573. (13 pages).
Official Action dated Sep. 8, 2016 From the US Patent and Trademark Office Re. U.S. Appl. No. 14/232,573. (12 pages).
Official Action dated Sep. 14, 2017 From the US Patent and Trademark Office Re. U.S. Appl. No. 14/232,573. (18 pages).
Official Action dated Apr. 17, 2017 From the US Patent and Trademark Office Re. U.S. Appl. No. 14/232,573. (18 pages).
Official Action dated May 17, 2016 From the US Patent and Trademark Office Re. U.S. Appl. No. 14/232,573. (11 pages).
Official Action dated Sep. 20, 2018 From the US Patent and Trademark Office Re. U.S. Appl. No. 14/232,573. (24 pages).
Official Action dated Mar. 28, 2018 From the US Patent and Trademark Office Re. U.S. Appl. No. 14/232,573. (19 pages).
Official Action dated Sep. 28, 2015 From the US Patent and Trademark Office Re. U.S. Appl. No. 14/232,573. (11 pages).
Supplementary European Search Report and the European Search Opinion dated Feb. 27, 2015 From the European Patent Office Re. Application No. 12811116.8.(8 Pages).
Written Opinion dated Nov. 11, 2012 From the International Searching Authority Re. Application No. PCT/IL2012/000278. (9 Pages).
Written Opinion dated Oct. 23, 2012 From the International Searching Authority Re. Application No. PCT/IL2012/000278. (8 Pages).
Boston Scientific "Reducing the Risk of Stroke in Atrial Fibrillation With the WATCHMAN™ Left Atrial Appendage (LAA) Closure Device", Boston Scientific, SH-282105-AA, Poster Leaflet, 2 P., Nov. 2014.
Hu et al. "Device-Based Approach to Prevention of Stroke in Atrial Fibrillation", The Journal of Innovations in Cardiac Rhythm Management. 6: 2038-2050, Jun. 2015.
Kreidieh et al. "Left Atrial Appendage Remodeling After Lariat Left Atrial Appendage Ligation", Circulation Arrhythm Electrophysiology, 8(6): 1351-1358, Pubhshed Online Oct. 20, 2015.
Omran "Left Atrial Appendage Anatomy: The LAA i Unique as a Fingerprint, How to Close Those Successfully?", Euro PCR 2016, Slide Show, 37 P., 2016.
Piccini et al. "Left Atrial Appendage Occlusion: Rationale, Evidence, Devices, and Patient Selection", European Heart Journal, EHW330: 1-9, Advance Access Pubheation Sep. 13, 2016.
Interview Summary dated Nov. 3, 2020 from the US Patent and Trademark Office Re. U.S. Appl. No. 16/408,506. (2 pages).
Official Action dated Sep. 1, 2020 from the US Patent and Trademark Office Re. U.S. Appl. No. 16/408,506. (26 pages).
Final Official Action dated May 28, 2021 from the US Patent and Trademark Office Re. U.S. Appl. No. 16/408,506. (17 pages).
Notice of Allowance dated Nov. 1, 2021 together with Interview Summary from the US Patent and Trademark Office Re. U.S. Appl. No. 16/408,406. (11pages).

* cited by examiner

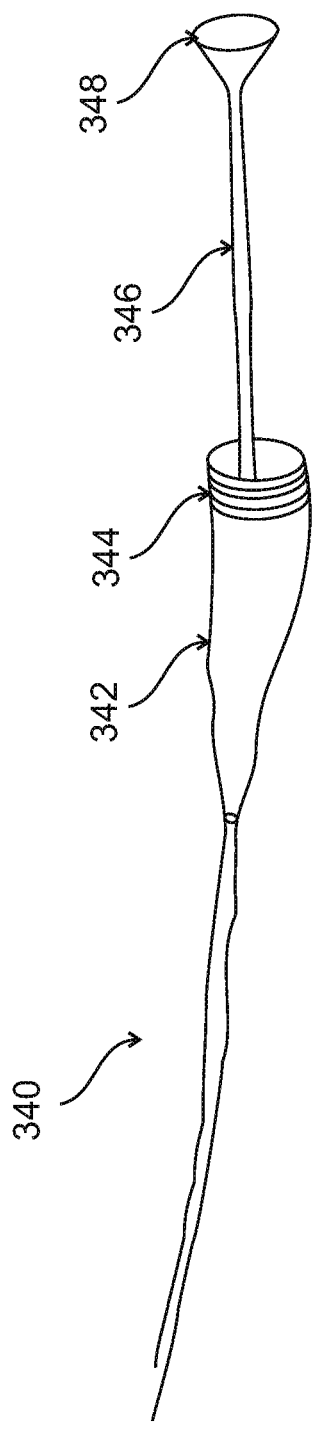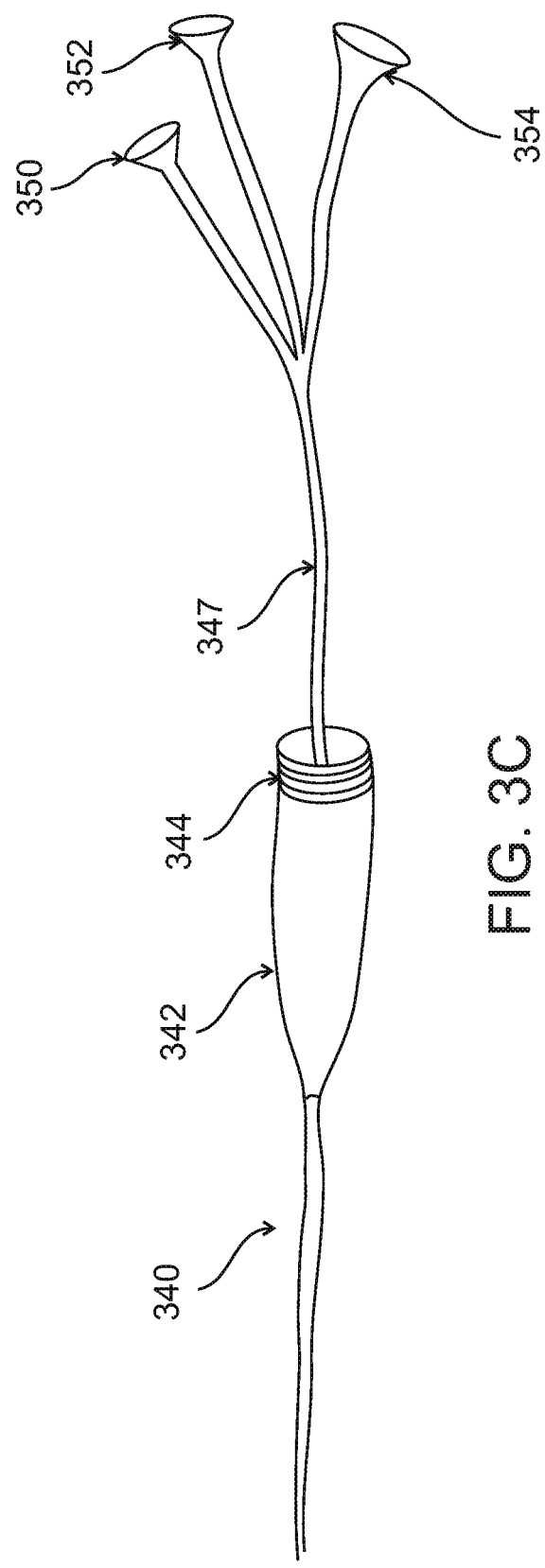

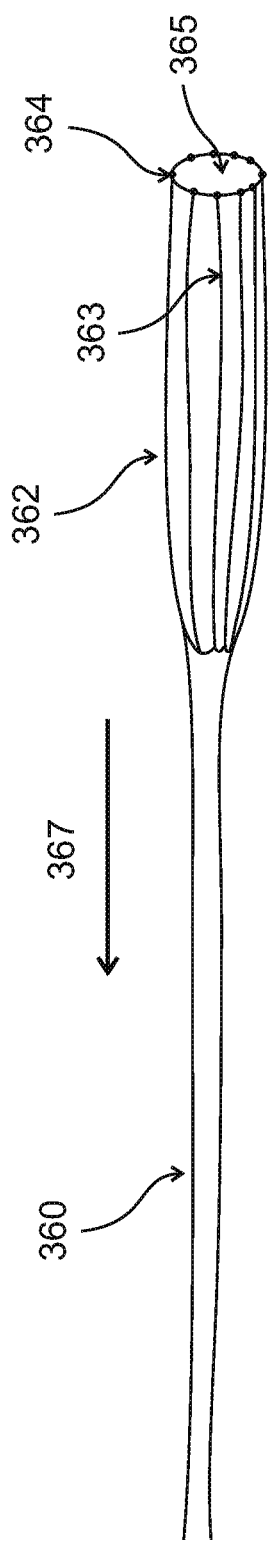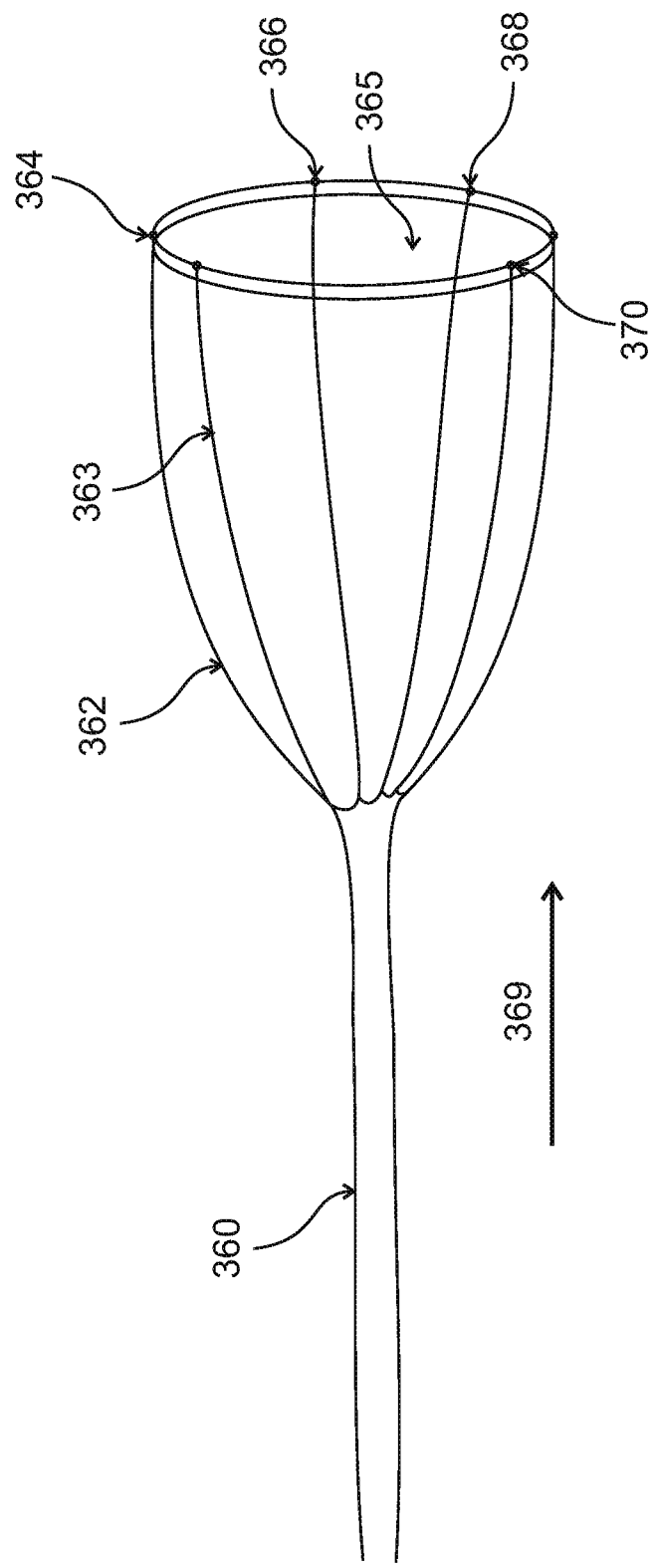

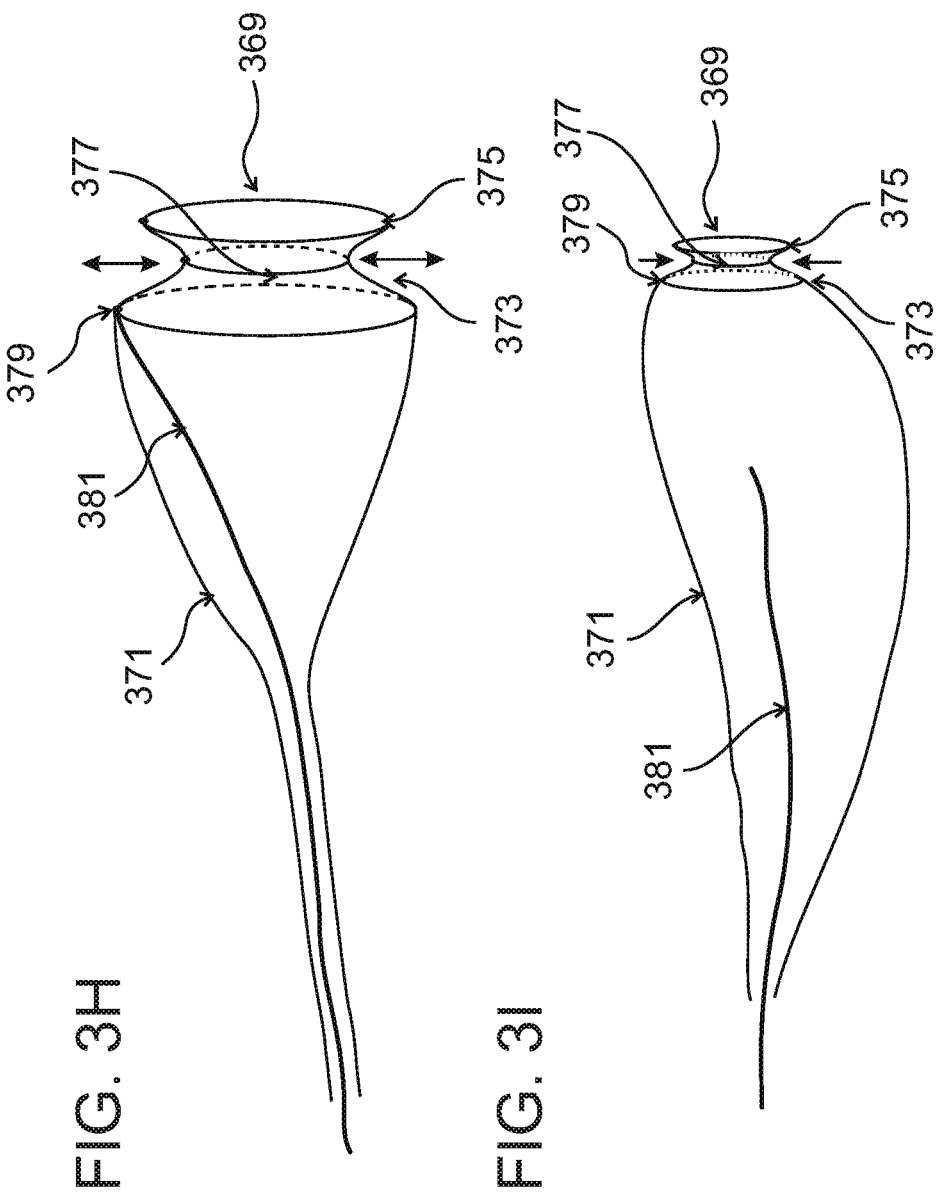

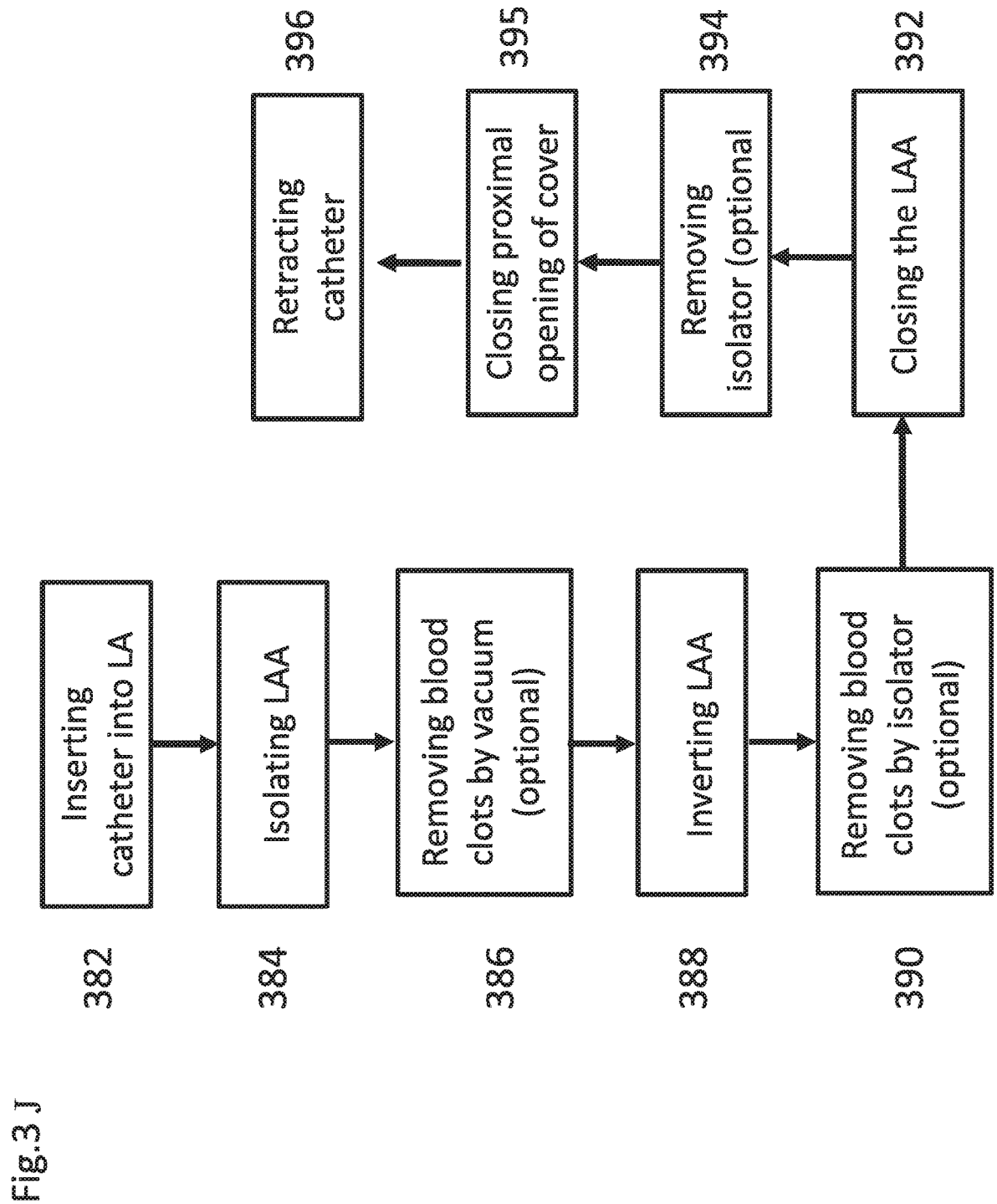

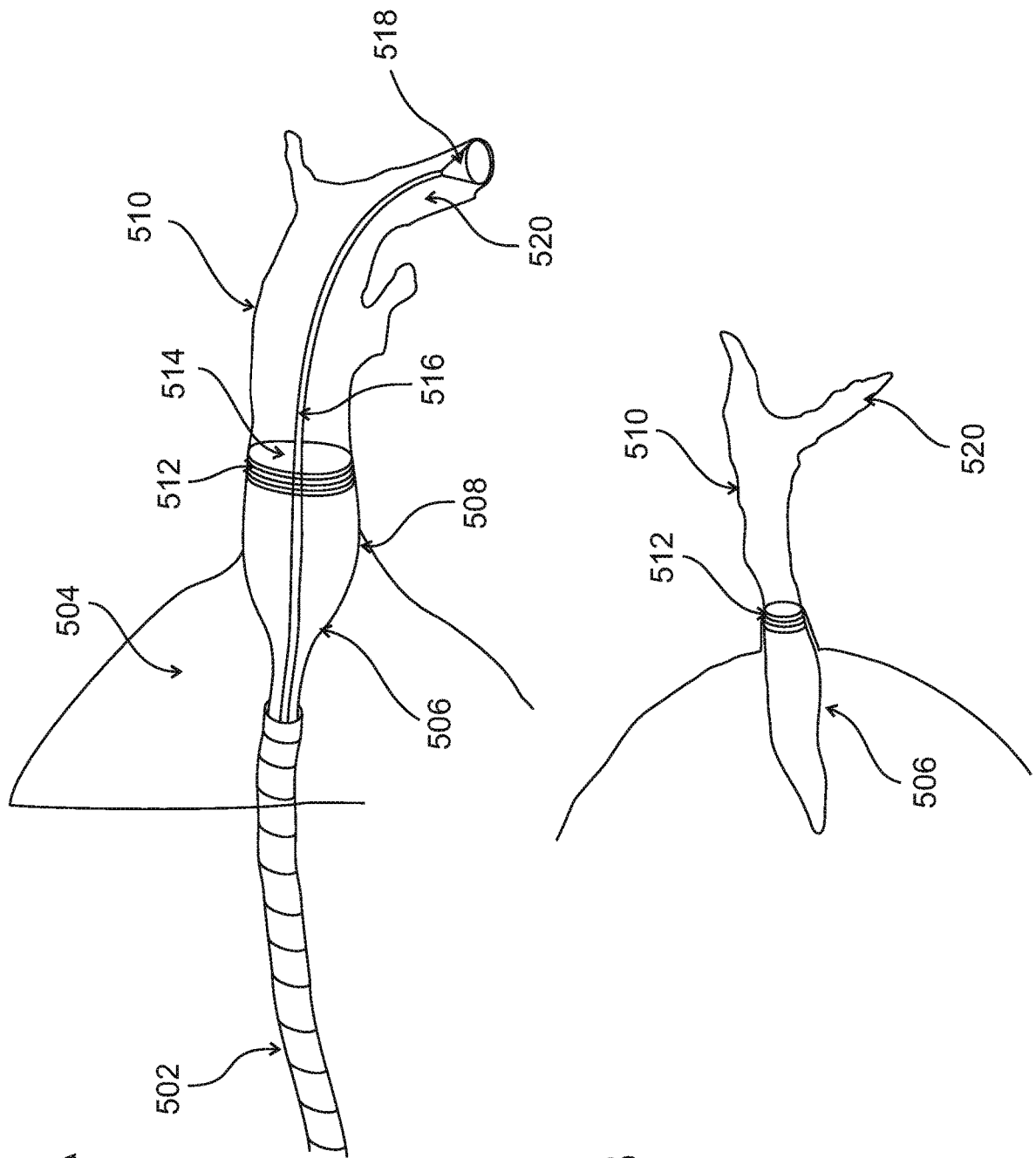

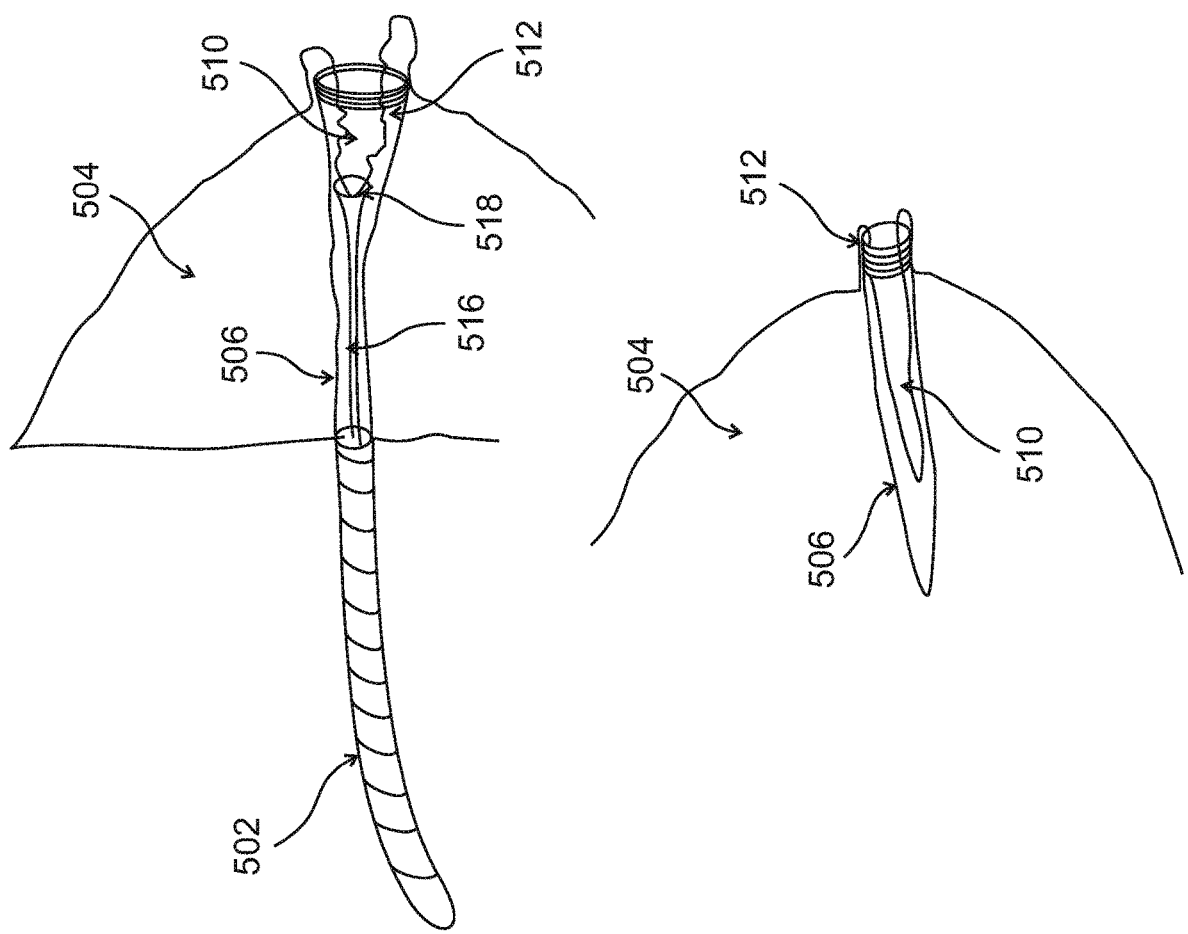

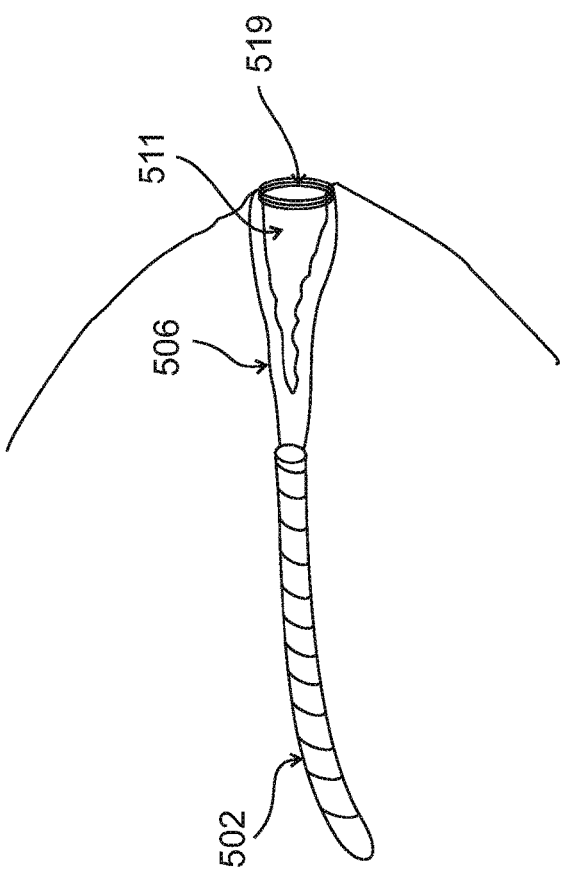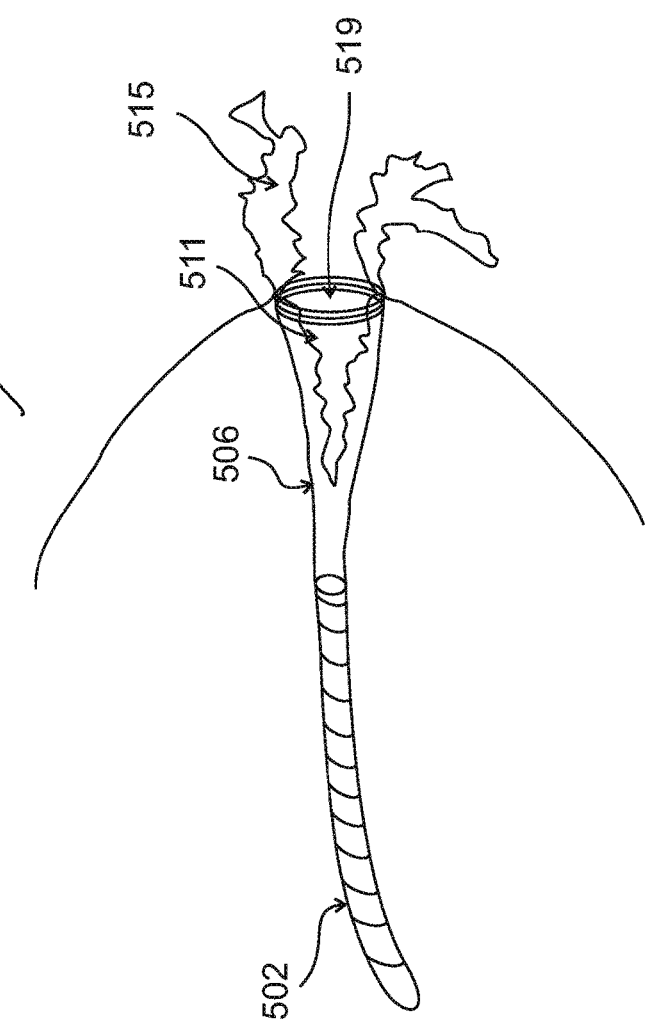

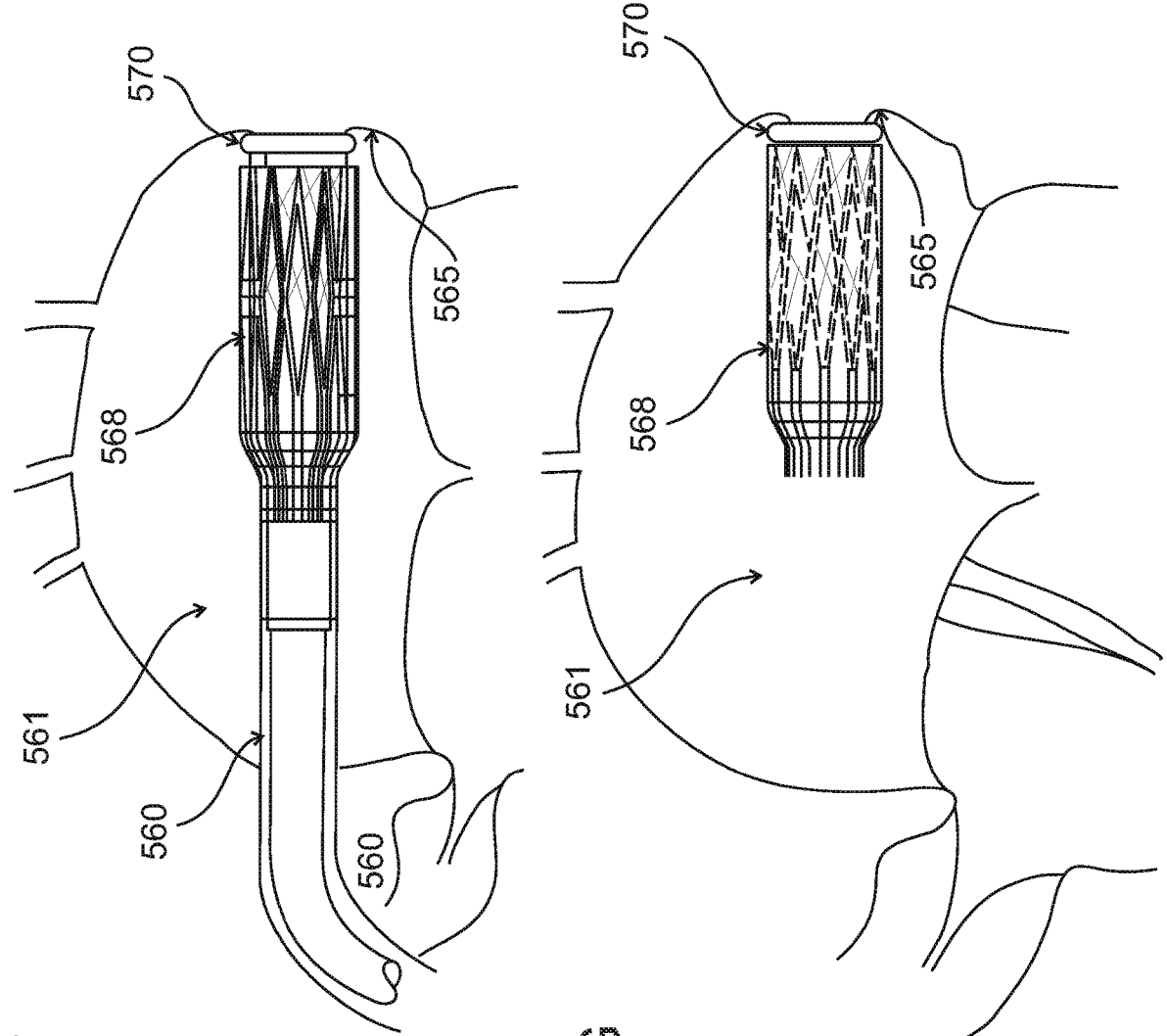

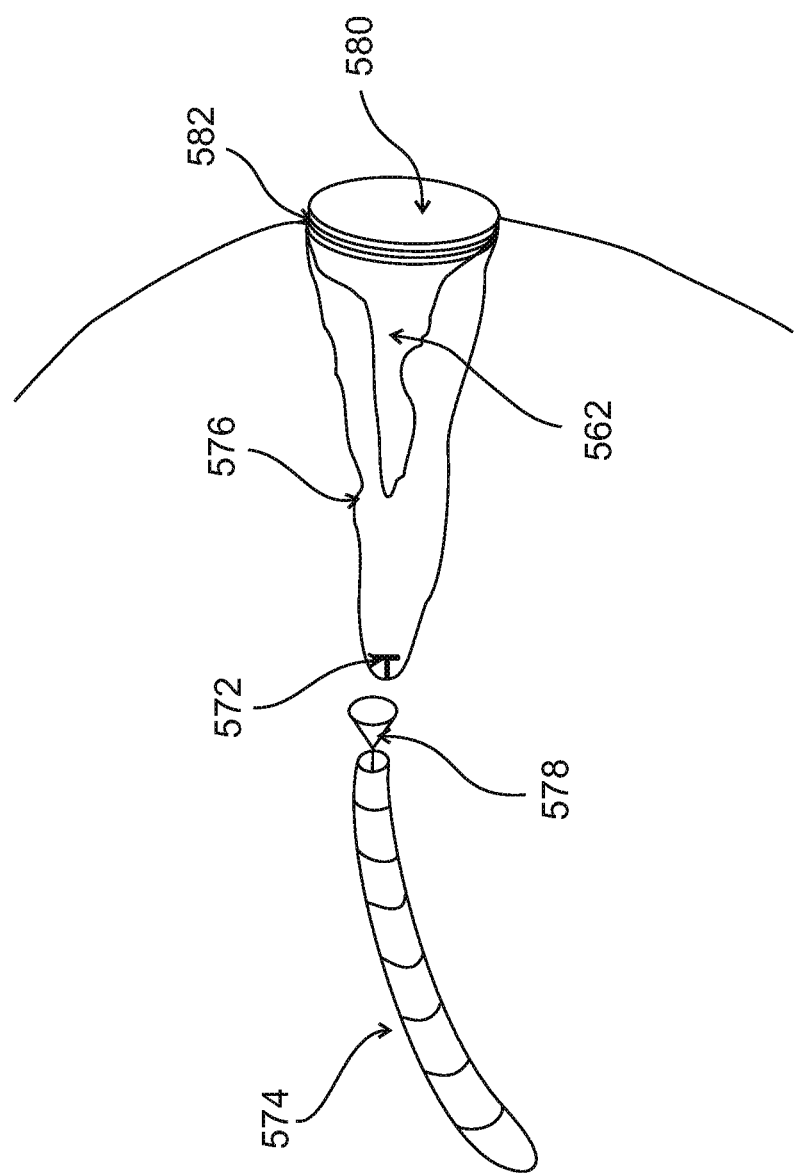

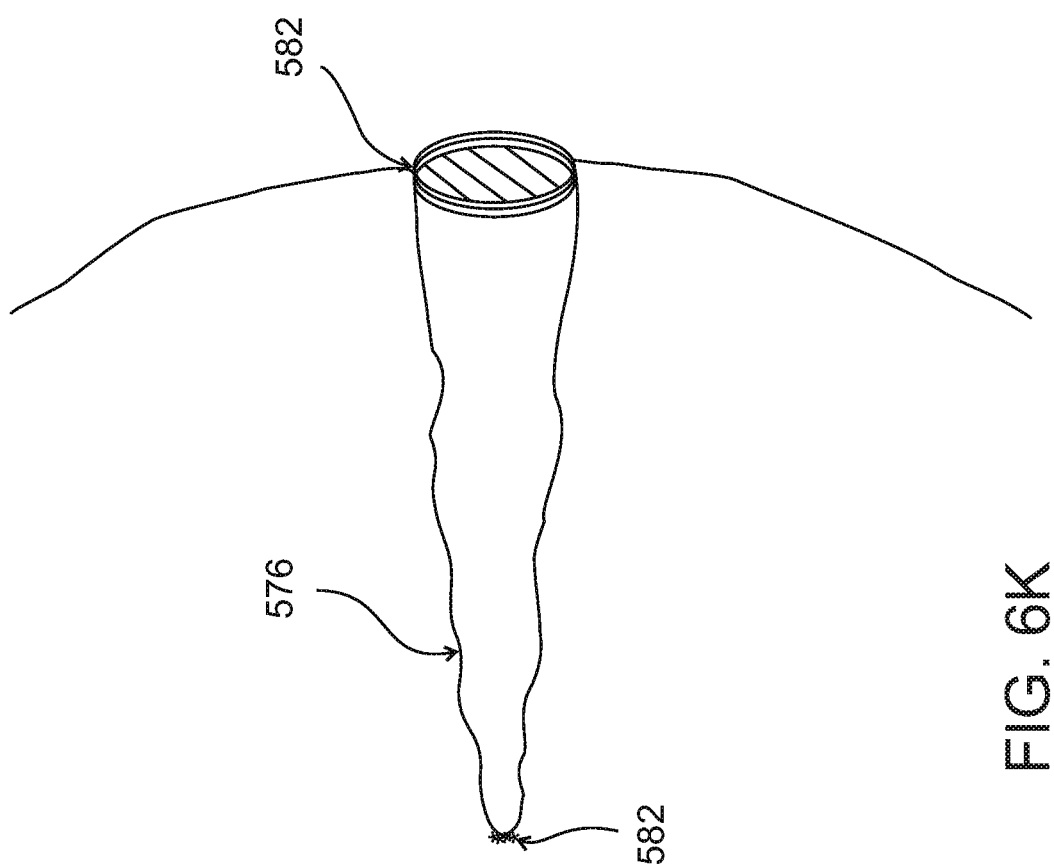

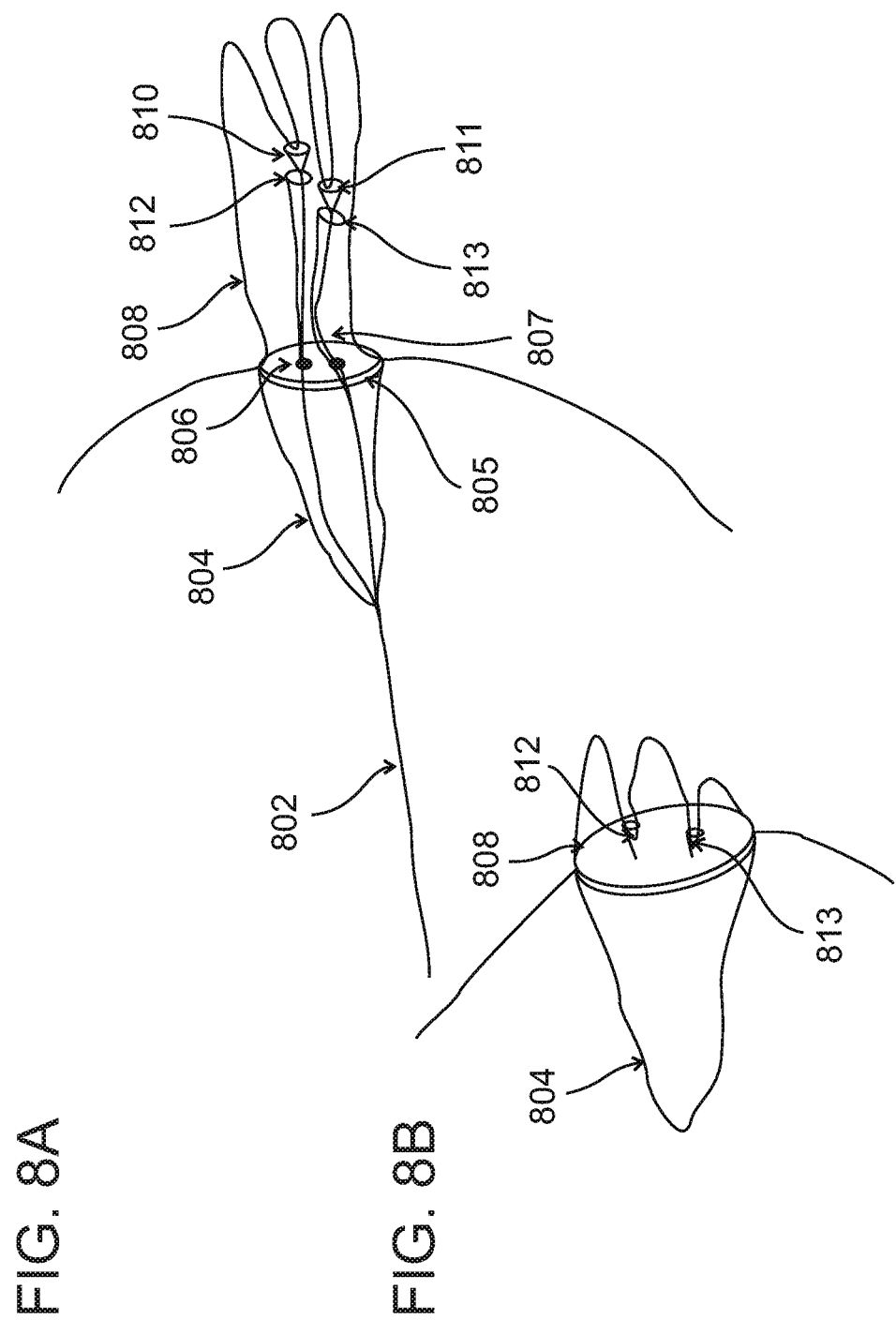

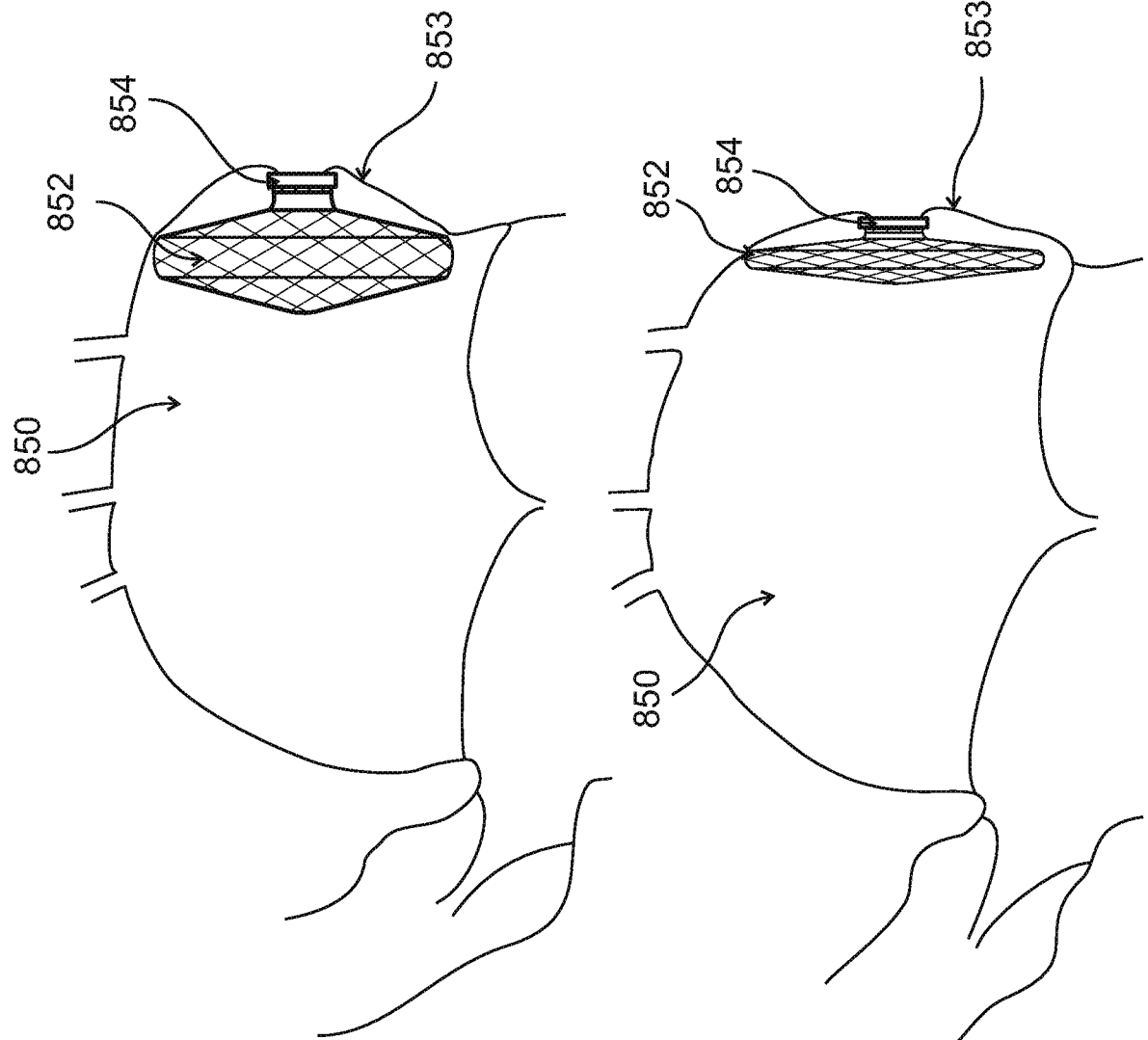

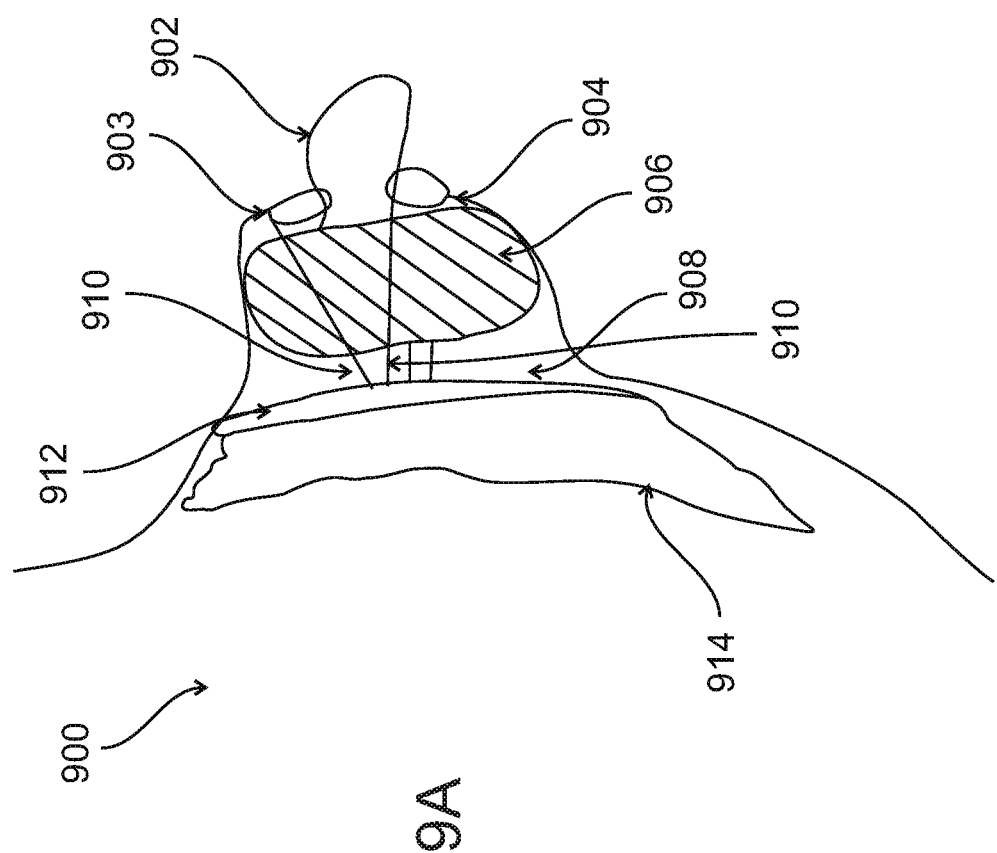

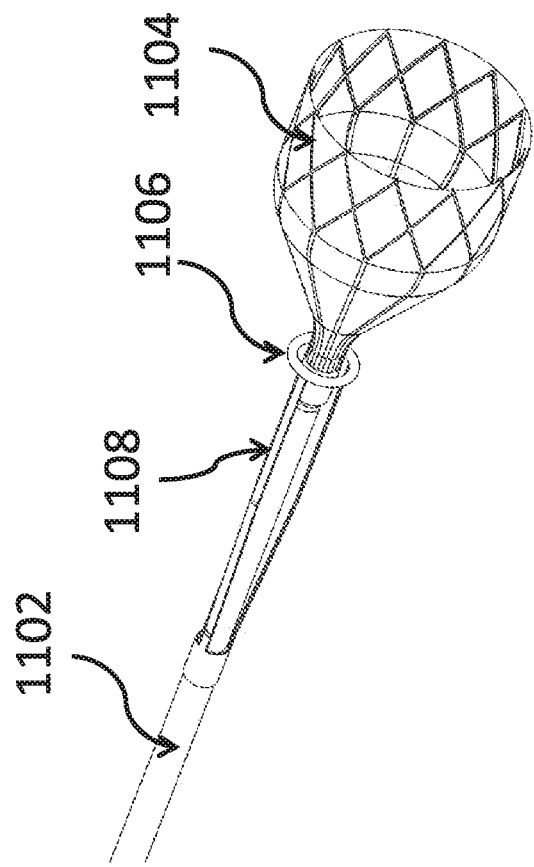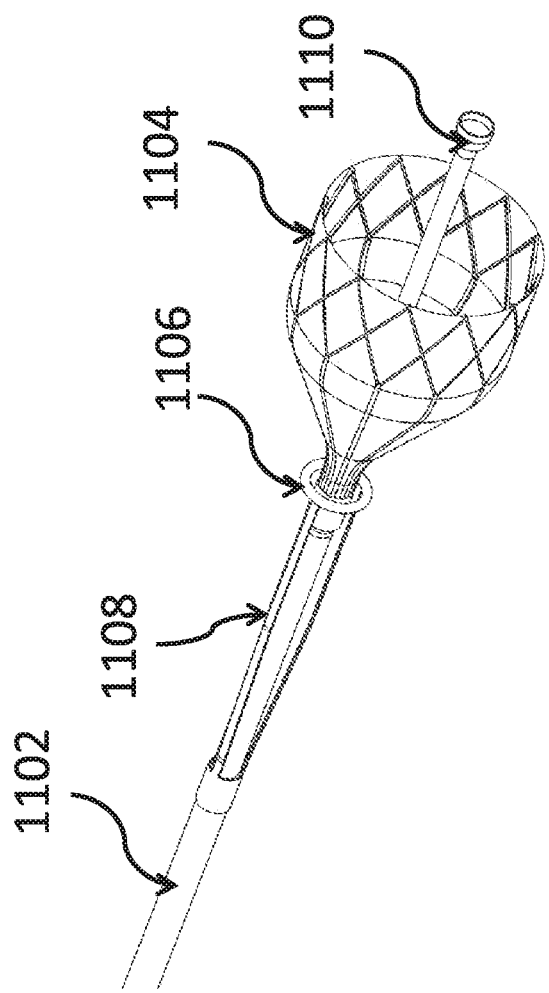
Fig.11C
Fig.11D

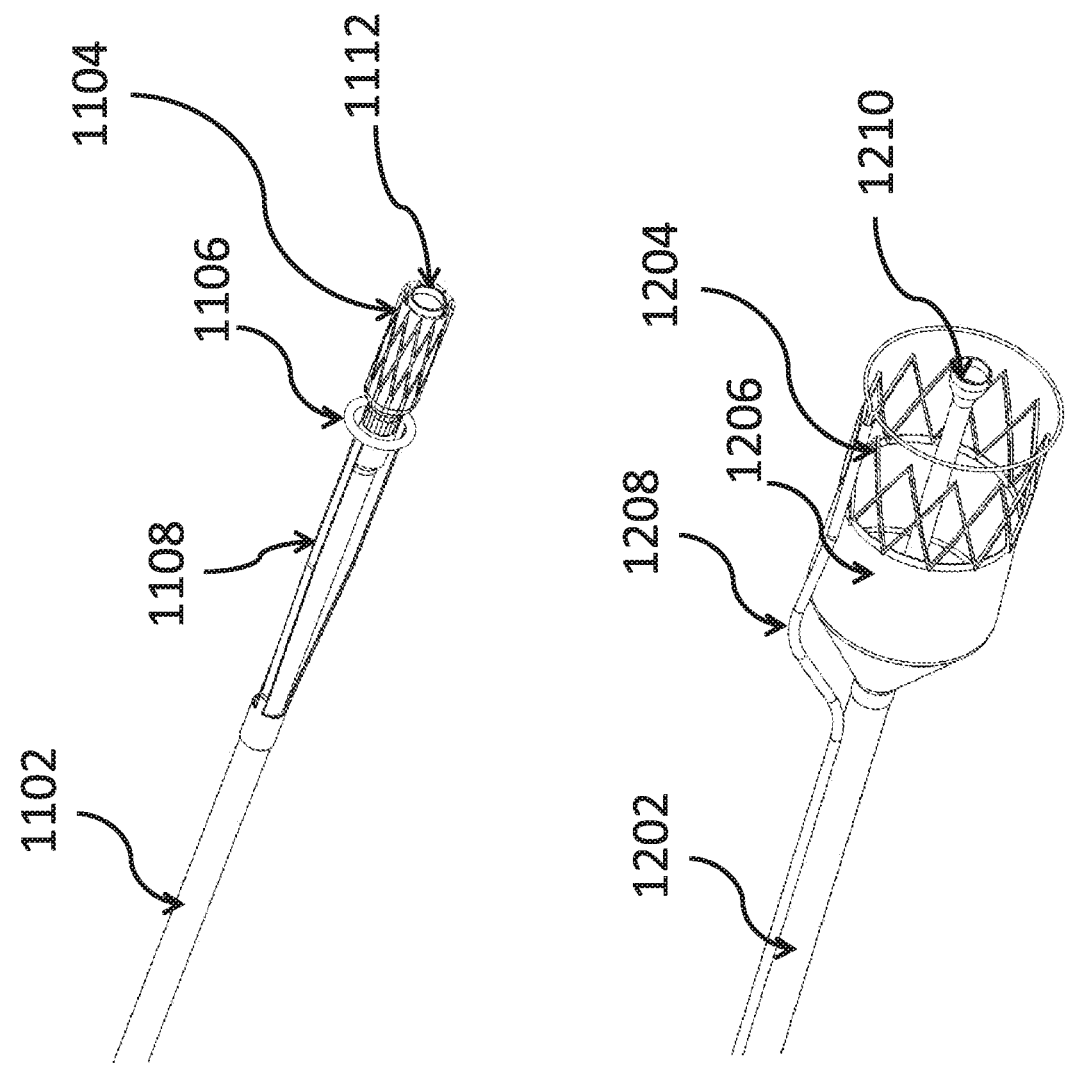

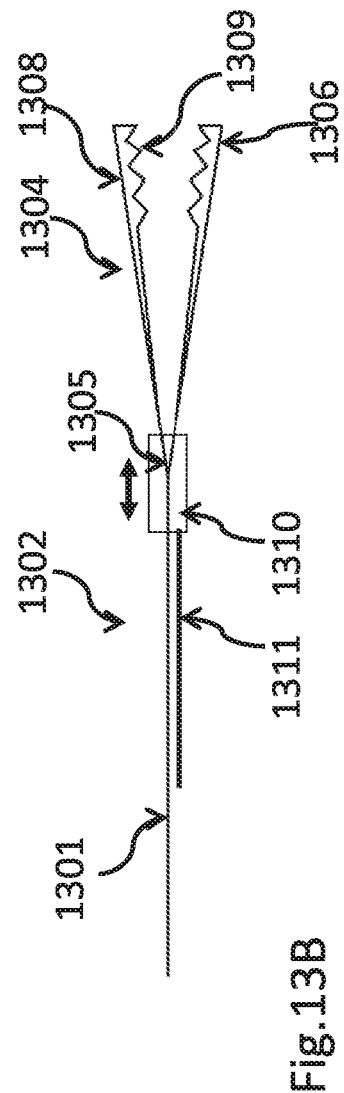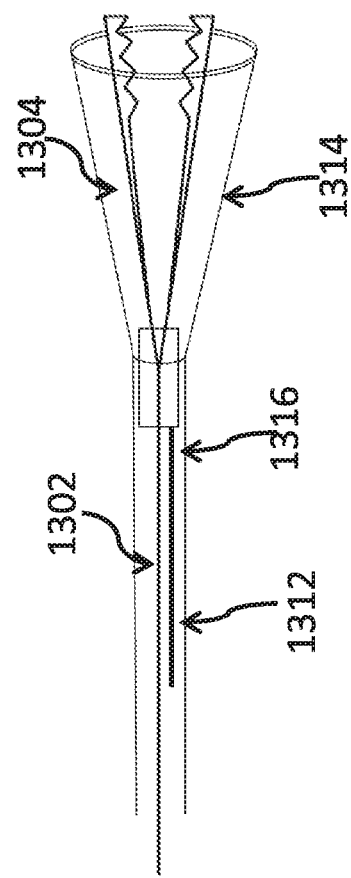
Fig.13A
Fig.13B

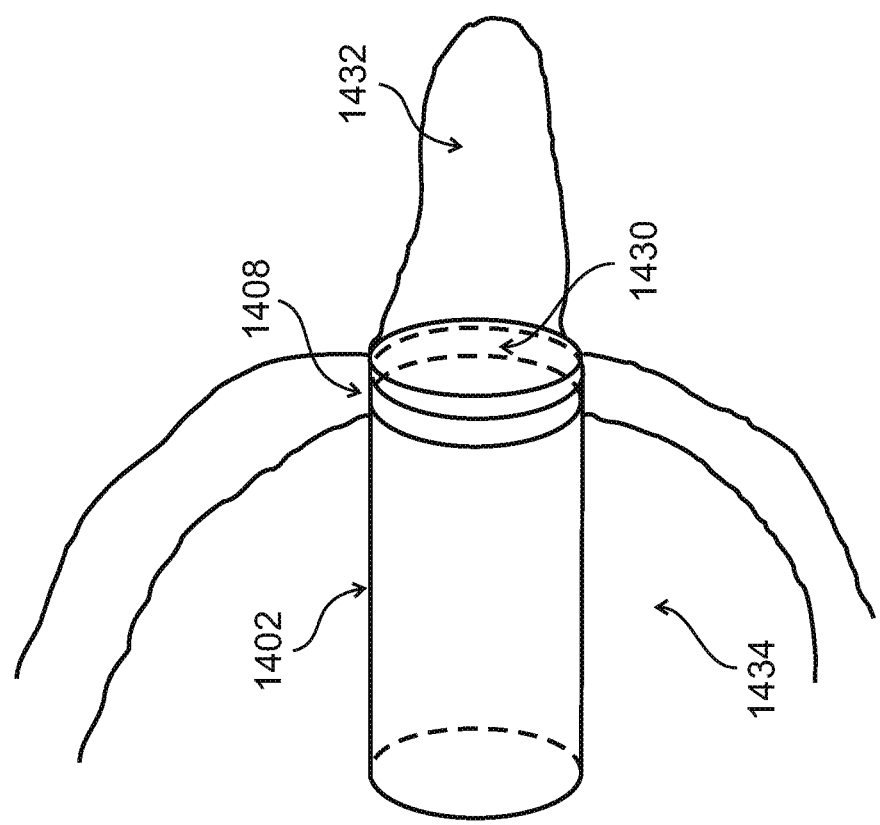

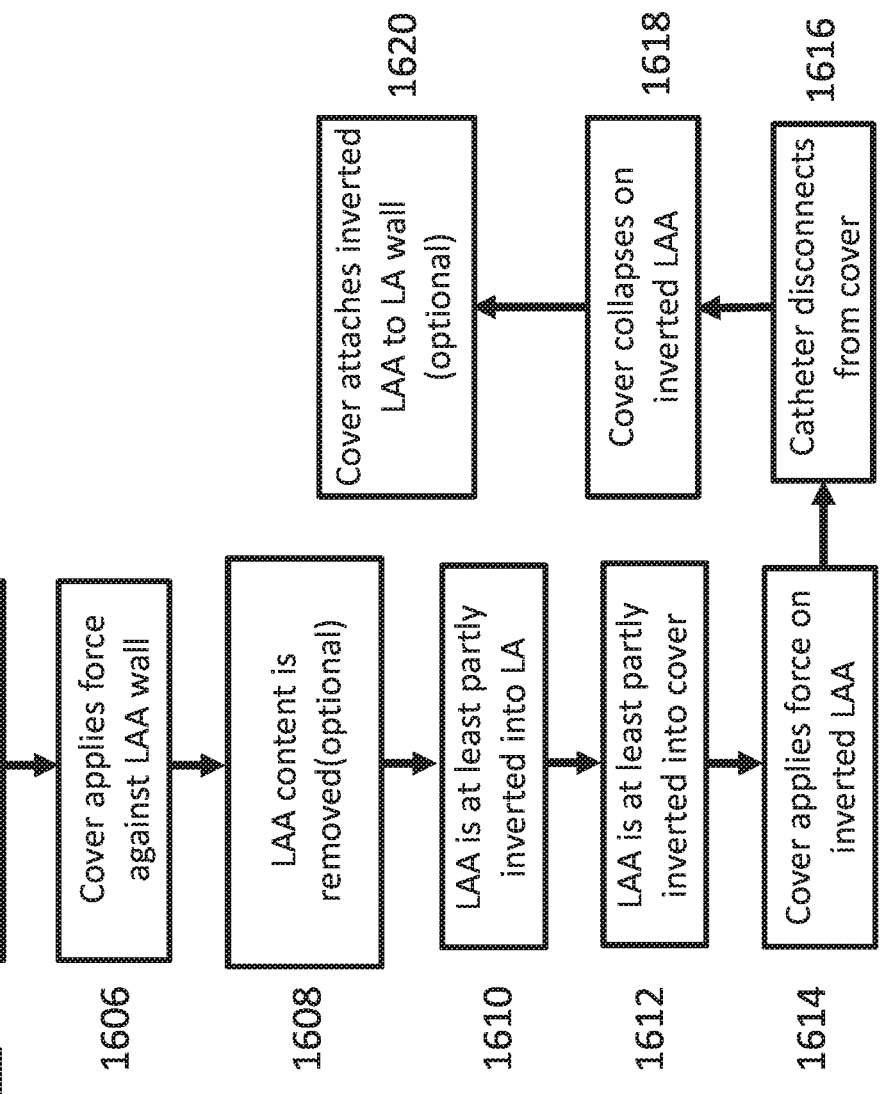

LEFT ATRIAL APPENDAGE CLOSURE

RELATED APPLICATIONS

This application is a National Phase of PCT Patent Application No. PCT/IL2018/050353 having International filing date of Mar. 27, 2018, which claims the benefit of priority under 35 USC § 119(e) of U.S. Provisional Patent Application No. 62/476,881 filed on Mar. 27, 2017. The contents of the above applications are all incorporated by reference as if fully set forth herein by reference in their entirety.

FIELD AND BACKGROUND OF THE INVENTION

The present invention, in some embodiments thereof, relates to closing a cardiac opening and, more particularly, but not exclusively, to closing the left atrial appendage.

The left atrial appendage (LAA) is a small, ear-shaped sac in the muscle wall of the left atrium (LA). Blood clots are often formed inside the LAA, especially in patients suffering from atrial fibrillation (AF), and upon their release to the LA they can lead to thrombotic stroke. In order to solve this problem different approaches are now used to close the LAA by placing a plug inside the LAA or by closing the LAA by fastening a lasso loop around it.

SUMMARY OF THE INVENTION

Some examples of some embodiments of the invention are listed below:

Example 1. A left atrium appendage (LAA) cover comprising:
a mesh body sized and shaped to fit an at least partially everted LAA; and
at least one anchor adapted to attach to an LAA.

Example 2. A cover according to example 1, wherein said anchor comprises a loop.

Example 3. A cover according to example 1 or example 2, wherein said cover is self-collapsing.

Example 4. A cover according to example 1, wherein said anchor comprises a ring.

Example 5. A cover according to example 1, wherein said mesh body comprises pores with a size of up to 100 micron.

Example 6. An LAA isolator system, comprising:
a catheter having a lumen;
an isolator extending form said catheter and having a distal opening large enough to at least match an opening of an LAA, and configured to prevent at least clots from existing said LAA into a general circulation;
an extendible LAA manipulation tool located within said lumen and within said isolator.

Example 7. A system according to example 6, wherein said isolator is porous.

Example 8. A system according to example 7, wherein said isolator is configured to detach from said system and collapse or be collapsed on an LAA.

Example 9. A system according to example 6, comprising an LAA anchor adapted to compress onto an everted LAA and remain anchored thereon.

Example 10. A system according to any one of examples 6 to 9, wherein said extendible LAA manipulation tool comprising a cleaning brush.

Example 11. A system according to any one of examples 6 to 9, wherein said extendible LAA manipulation tool comprises a vacuum head.

Example 12. An LAA isolating cap, comprising:
an LAA anchor adapted to attach to an everted LAA;
a collapsible cap sized to cover an opening into an LAA when collapsed to a flat state.

Example 13. A cap according to example 12, wherein said anchor comprises a cover which collapses on said LAA.

Example 14. A cap according to example 12, wherein said cover is non-porous.

Example 15. A cap according to example 12, wherein said anchor comprises a loop which is fastened around said everted LAA.

Example 16. A method for isolating the LAA, comprising:
inserting a catheter into the LA;
positioning a distal section of an isolator into said LAA while keeping a proximal section of said isolator within a lumen of said catheter;
fastening said isolator to the inner surface of said LAA.

Example 17. The method of example 16, further comprising inserting a manipulating element inside said LAA following said fastening.

Example 18. A method for closing the LAA, comprising:
isolating said LAA from the LA to prevent the release of blood clots from said LAA into said LA;
inverting at least one section of said LAA;
placing a fastening element around said section of said LAA;
fastening said fastening element around said section of said LAA.

Example 19. The method of example 18, wherein said placing comprising advancing said fastening element to a desired location on said LAA before said fastening.

Example 20. The method of examples 18 or 19, further comprising anchoring said fastening element to said section of said LAA.

Example 21. A method for closing the LAA, comprising:
inverting at least partially said LAA;
fastening a fastening element around said partially inverted section.

Example 22. The method of example 21, comprising:
isolating said LAA from the LA before said inverting to prevent the release of blood clots from said LAA into said LA during said inverting.

Example 23. The method of example 21 or 22, wherein said inverting comprises inverting at least partially said LAA inside said LAA.

Example 24. A method for reshaping the LAA, comprising:
inverting at least one section of said LAA at least partly into the LA;
fastening a fastening element around said inverted section;
attaching a cover to said inverted section.

Example 25. The method of example 24, comprising:
isolating said LAA from said LA before said inverting.

Example 26. A method for attaching the LAA to the LA wall, comprising:
positioning a sealing element inside the LA over an opening between said LA and the LLA;
inverting at least one section of said LLA at least partly into the LA;
placing an adjustable closing element around said section of said LLA; fastening said adjustable closing element around said section of said LLA to prevent the opening of said section;
positioning said inverted section of said LLA between said sealing element and said LA wall;

pushing said sealing element to said LA wall with a force sufficient to attach said inverted section of said LLA to said LA wall.

Example 27. A method of treating an LAA, comprising:
isolating said LAA;
manipulating said LAA in a manner which will cause debris to exit said LAA and be captured by said isolator;
removing said isolator.

Example 28. A method according to example 27, wherein said manipulating comprises everting said LAA.

Example 29. A method according to example 27 wherein said manipulating comprises implanting an LAA blocking device.

Example 30. A method of treating an LAA, comprising:
everting an LAA, at least in part;
mounting an LAA reshaping device on said everted LAA, over at least 1 cm of its length.

Example 31. A method of anchoring to an LAA, comprising:
everting an LAA less than 90%;
mounting an anchor on said everted LAA, said anchor also preventing LAA reverse-everting.

Some additional examples of some embodiments of the invention are listed below:

Example 1. A left atrium appendage (LAA) isolator, comprising:
a body sized and shaped to fit an at least partially inverted LAA of a human adult, wherein a distal end of said body defines a two-state sealing adaptor interface configured in a first state to apply a radially outward force against a wall of said LAA or against a wall of said LAA opening sufficient to anchor said body to said LAA wall, and in a second state the sealing adaptor interface is configured to apply a radially inward force on a portion of said inverted LAA positioned within said body.

Example 2. An isolator according to example 1, wherein said radially outward force applied by said two-state sealing adaptor on said LAA wall in said first state is up to 10 Newton.

Example 3. An isolator according to any one of the previous examples, wherein said two-state sealing adaptor defines a circumferential groove in said body, wherein said circumferential groove is shaped and sized to fit said body within said LAA opening.

Example 4. An isolator according to any one of the previous examples, wherein said two-state sealing adaptor deforms said LAA wall to fit an external shape of said body.

Example 5. An isolator according to any one of the previous examples, wherein said sealing adaptor comprises at least one elastic ring associated with said body.

Example 6. An isolator according to example 5, wherein said at least one elastic ring expands under elastic conditions to a maximal width of 4 cm.

Example 7. An isolator according to any one of the previous examples, wherein said sealing adaptor comprises at least 3 elastic rings, and wherein at least one intermediate ring of said at least 3 elastic rings located between a proximal ring and a distal ring within said body is shaped and sized to fit in said LAA opening.

Example 8. An isolator according to example 7, wherein said intermediate ring is configured to expand in a resting state to a maximal expansion range smaller in at least 10% from the maximal expansion range of the proximal ring and/or the distal ring.

Example 9. An isolator according to any one of the previous examples, wherein said body comprises pores with a maximal dimension of up to 200 microns.

Example 10. An isolator according to any one of the previous examples, wherein said body comprises a porous mesh forming a web shaped structure with openings having a maximal dimension of up to 200 microns.

Example 11. An isolator according to example 10, wherein said porous mesh structure is formed from a memory shape alloy.

Example 12. An isolator according to any one of the previous examples, wherein said body is a tubular body defining a distal opening and a proximal opening and wherein said two-state sealing adaptor is associated with said distal opening.

Example 13. An isolator according to example 12, wherein a portion of said body associated with said proximal opening is pre-formed to be self-collapsible.

Example 14. An isolator according to example 12, wherein said body comprises at least one adjustable ring associated with said proximal opening.

Example 15. An isolator according to example 14, wherein said at least one adjustable ring is configured to be irreversibly tightened in response to an external force applied by at least one wire connected to said at least one adjustable ring.

Example 16. An isolator according to example 12, wherein said body comprises at least one self-collapsing ring associated with said proximal opening configured to irreversibly collapse and close said proximal opening.

Example 17. An isolator according to example 16, wherein said at least one self-collapsing ring is formed from a memory shape alloy preformed to construct and close said proximal opening.

Example 18. An isolator according to any one of the previous examples, wherein said body in an expanded state has a length of up to 4 cm from an LA wall.

Example 19. An isolator according to any one of the previous examples, wherein a maximal width or a maximal diameter of said body in an expanded state is up to 4 cm.

Example 20. An isolator according to any one of the previous examples, wherein said body is self-collapsing.

Example 21. An isolator according to example 20, wherein said body is collapsible to a disc-shaped structure having a width of up to 10 mm.

Example 22. An isolator according to example 21, wherein a diameter of said disc-shaped structure is at least 1 cm.

Example 23. An LAA isolator system, comprising:
a catheter having a lumen, wherein said catheter is insertable into the LA of a human adult;
an isolator extending from said catheter into the LA and having a proximal opening facing said catheter and a distal opening large enough to at least match an opening of an LAA, and configured to prevent at least clots from exiting said LAA into a general circulation;
an extendible LAA manipulation tool located within said lumen and within said isolator, wherein said extendible LAA manipulation tool is configured to at least partially invert an LAA portion into said LA.

Example 24. A system according to example 23, wherein said isolator is porous.

Example 25. A system according to any one of examples 23 or 24, wherein said isolator is configured to detach from said system and collapse or be collapsed on an LAA portion inverted into said LA.

Example 26. A system according to any one of examples 23 to 25, comprising an LAA anchor adapted to compress onto an everted LAA and remain anchored thereon.

Example 27. A system according to any one of examples 23 to 26, wherein said extendible LAA manipulation tool comprising a cleaning brush.

Example 28. A system according to any one of examples 23 to 26, wherein said extendible LAA manipulation tool comprises a vacuum head connected to a vacuum channel passing through said lumen of said catheter.

Example 29. A system according to any one of examples 23 to 26, wherein said extendible LAA manipulation tool comprises an extendible grasping member, wherein said grasping member comprises a grasping head with a plurality of protrusions shaped and sized contact and hold a portion of a wall of said LAA.

Example 30. A system according to example 28, wherein said extendible LAA manipulation tool comprises an extendible grasping member extending through said vacuum channel and said vacuum head into said LAA, wherein said grasping member comprises a grasping head with a plurality of protrusions shaped and sized to contact and hold a portion of a wall of said LAA.

Example 31. A system according to any one of examples 23 to 30, wherein said isolator comprises a two-state sealing adaptor associated with said distal opening configured in a first state to apply a radially outward force against said LAA opening sufficient to anchor said isolator to a wall of said LAA opening, and in a second state to collapse on a portion of said LAA inverted into said isolator.

Example 32. A system according to example 31, wherein said two-state sealing adaptor applies force of up to 10N against said wall of said LAA opening.

Example 33. A system according to any one of examples 31 or 32, wherein said two-state sealing adaptor forms a circumferential groove in an external surface of said isolator, wherein said circumferential groove is shaped and sized to be positioned within said LAA opening.

Example 34. A system according to any one of examples 23 to 33, wherein said isolator is pre-formed to be self-collapsible around a proximal opening of said isolator facing said catheter, wherein said isolator is configured to collapse and close said proximal opening when said isolator is disconnected from said catheter.

Example 35. A system according to any one of examples 23 to 34, wherein said isolator is self-collapsible, configured to collapse on an inverted portion of said LAA positioned within said isolator.

Example 36. A system according to any one of examples 23 to 35, wherein said isolator comprises a porous mesh forming a web shaped structure with openings having a maximal dimension of up to 200 microns.

Example 37. A system according to example 36, wherein said porous mesh is formed from a memory shape alloy.

Example 38. A system according to any one of examples 23 to 37, wherein said isolator comprises at least one adjustable ring associated with a proximal opening of said isolator facing said catheter, wherein said at least one adjustable ring closes said proximal opening upon application of an external force on said adjustable ring.

Example 39. A system according to any one of examples 23 to 38, wherein said isolator is self-collapsible into a disc-shaped structure having a width of up to 10 mm.

Example 40. A system according to example 39, wherein a maximal dimension of said disc-shaped structure is at least 1 cm.

Example 41. An LAA isolating cap, comprising:
at least one occluder shaped and sized to be at least partly positioned within an LAA opening;
a collapsible cap sized to cover an opening into an LAA when collapsed to a flat state.

Example 42. A cap according to example 41, comprising at least one LAA anchor adapted to attach to at least one everted LAA portion; wherein said at least one occluder and/or said collapsible cap is connected to said at least one LAA anchor.

Example 43. A cap according to example 42, wherein said at least one LAA anchor LAA comprises a loop which is fastened around one or more of said everted LAA portions.

Example 44. A cap according to any one of example 41 to 43, wherein said cap is non-porous.

Example 45. A cap according to any one of examples 41 to 44 wherein said cap is at least partly porous, having pores with a maximal dimension of up to 200 microns.

Example 46. A method for reshaping the LAA, comprising:
inverting at least one section of said LAA at least partly into the LA;
fastening a fastening element around said inverted section;
attaching a cover to said inverted section.

Example 47. The method of example 46, comprising:
isolating said LAA from said LA before said inverting.

Example 48. A method for closing the LAA, comprising:
isolating said LAA from the LA to prevent the release of blood clots from said LAA into said LA;
inverting at least one section of said LAA at least partially into said LA;
placing a fastening element around said section of said LAA;
fastening said fastening element around said section of said LAA.

Example 49. The method of example 48, wherein said placing comprising advancing said fastening element to a desired location on said LAA before said fastening.

Example 50. The method of any one of examples 48 or 49, further comprising anchoring said fastening element to said section of said LAA.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3B-3C are schematic illustrations of a device for covering at least part of the LAA with a varying number of inverting heads, according to some embodiments of the invention;

FIGS. 3D-3E are schematic illustrations of a cover in a closed and open states, according to some embodiments of the invention;

FIG. 3H is a schematic illustration of a cover comprising at least two rings near a distal opening of the cover in an open conformation, according to some embodiments of the invention;

FIG. 3I is a schematic illustration of a cover comprising at least two rings near a distal opening of the cover, according to some embodiments of the invention;

FIG. 3J is a flow chart describing a process for closing the LAA, according to some embodiments of the invention;

FIGS. 5A and 5B are schematic illustrations of a cover positioned inside the LAA, according to some embodiments of the invention;

FIGS. 6A and 6B are schematic illustrations of a cover wrapped around an inverted section of the LAA, according to some embodiments of the invention;

FIG. 6C is a schematic illustration of a cover wrapped around a fully inverted LAA, according to some embodiments of the invention;

FIG. 6D is a schematic illustration of a cover wrapped around a partially inverted LAA, according to some embodiments of the invention;

FIG. 6F is a schematic illustration of a mesh in a closed conformation wrapped around an inverted LAA, according to some embodiments of the invention;

FIG. 6G is a schematic illustration of a mesh in a closed conformation after the retraction of the catheter, according to some embodiments of the invention;

FIGS. 6H-6K are schematic illustrations of proximal closing mechanisms, according to some embodiments of the invention;

FIGS. 8A-8B are schematic illustrations describing the closure of inverted LAA sections using a lasso, according to some embodiments of the invention;

FIGS. 8C-8D are schematic illustrations of a disc-shaped isolator wrapped around an inverted LAA in an expanded and a contracted conformations, according to some embodiments of the invention;

FIGS. 9A-9C are schematic illustrations of plug devices positioned in the LAA and are isolated from the LA by an isolator, according to some embodiments of the invention;

FIGS. 11A-11E are schematic illustrations of catheter deployment mechanisms, according to some embodiments of the invention;

FIGS. 12A-12H are additional schematic illustrations of a catheter deployment mechanisms, according to some embodiments of the invention;

FIGS. 13A-13B are schematic illustrations of a grasping member, according to some embodiments of the invention;

FIG. 14C is a schematic illustration of a sealing adaptor of a cover sealing the LAA opening, according to some embodiments of the invention;

FIG. 16 is a flow chart of an activation process of a device for closing the LAA, according to some embodiments of the invention.

DESCRIPTION OF SPECIFIC EMBODIMENTS OF THE INVENTION

Figure 1:
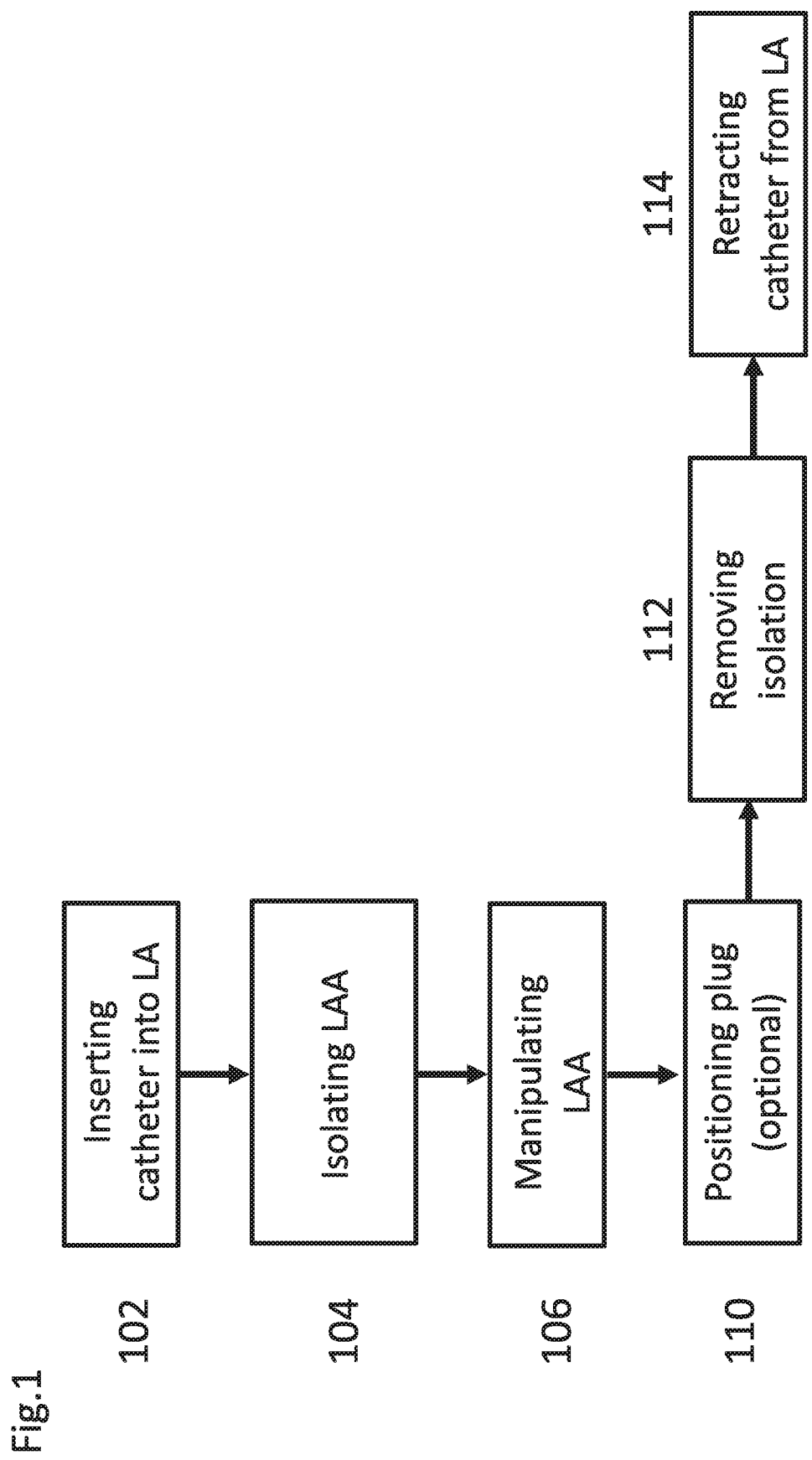
FIG. 1 is a flow chart describing a process for isolating the left atrial appendage (LAA), according to some embodiments of the invention.

The present invention, in some embodiments thereof, relates to closing a cardiac opening and, more particularly, but not exclusively, to closing the left atrial appendage.

An aspect of some embodiments relates to isolating the left atrium appendage (LAA) from the left atrium (LA) before manipulating the LAA. In some embodiments, the LAA is isolated from the LA to prevent the release of blood clots or tissue debris from the LAA lumen into the LA and into the blood stream. In some embodiments, for example in patients suffering from atrial fibrillation (AF), release of blood clots from the LAA may cause thrombotic stroke. Therefore a possible advantage of isolating the LAA content from the LA, for example in AF patients, is that it allows to intentionally treat AF patients that imaging techniques showed that they have blood clots in their LAA by directing the LAA content outside of the body or trapping the LAA content before it enters the blood stream.

According to some embodiments, the LAA is isolated prior to the insertion of a closure element into the LAA, for example in order to prevent the release of the LAA content during the insertion and positioning of the closure element. In some embodiments, the LAA is isolated prior to insertion of elements used to clean the LAA lumen, for example brushes or vacuum applying elements. Alternatively, the LAA is isolated prior to intra-cardiac remodeling of the LAA, for example by internal inverting of the LAA, or extracardiac remodeling of the LAA. In some embodiments, the LAA is isolated prior to any manipulation of the LAA. As used herein and throughout the application inverting the LLA refers to evert the LAA over itself and therefore invert it in space.

In some embodiments, the LAA is partially inverted, for example inverted less than 90%, for example 80%, 70%, 40% or 30% or any intermediate or smaller percentage, of the LAA length before inversion.

According to some embodiments, a catheter is inserted into the LA and positions an isolator, for example an elastic cover over the opening of the LAA. In some embodiments, the proximal end of the cover is placed inside the catheter lumen. In some embodiments, the distal opening of the cover is positioned at least partially within the LAA opening. In some embodiments, the cover is attached to the LA wall surrounding the LAA opening, for example using at least one anchor on the leading edge of the cover, facing the tissue. In some embodiments, the anchor is a reversible anchor configured to be released from the LA wall, for example when the isolation process ends. Alternatively, the cover is actively pushed against the LA wall, for example by the operator or due to his structure, surrounding the LAA opening, during the LAA isolation process. In some embodiments, the cover is pulled towards the LA wall, optionally by vacuum. In some embodiments, the cover is inserted into the LAA, and is optionally pushed against the internal wall of the LAA. Alternatively, the cover is pulled towards the internal wall of the LAA. In some embodiments, the cover directs blood clots or tissue debris from the LAA into the lumen of the catheter, optionally by application of vacuum. Alternatively, the cover traps the blood clots and/or tissue debris on its surface facing the LAA. In some embodiments, the cover is retracted from the LA once the isolation process is over.

In some embodiments, the cover is an elastic mesh with pores in a size of 80-130 microns ($\mu m$). Alternatively, the cover is an elastic mesh with pores having a maximal dimension of up to 200 microns, for example 10 microns, 50 microns, 100 microns, 150 microns or any intermediate, smaller or larger value. In some embodiments, the mesh allows particles smaller than 80 microns ($\mu m$) or any smaller or larger value to flow between the LAA and the LA In some embodiments, the pores allow blood flow between the LA and the LAA but not the flow biological particles larger than the pores size, for example blood clots or tissue debris. In some embodiments, the mesh traps the clots and/or the biological debris, optionally in the pores.

According to some exemplary embodiments, a catheter device is inserted into the LA and pushes an isolator opening, for example a tube distal opening against the LA wall, in a way that the tube distal opening surrounds the LAA opening. In some embodiments, the tube comprises at least one anchor in the distal end of the tube facing the LA wall. Alternatively, the tube is pressed against the LA wall without penetration. In some embodiments, the anchor anchors the distal end of the tube to the LA wall in a way that prevents leakage of blood clots and/or tissue debris from the LAA into the LA. In some embodiments, the anchor is a reversible anchor which allows, for example, detaching the tube from the LA wall when the isolation process is over.

According to some embodiments, the tube is positioned inside the LAA and placed in contact with the internal wall of the LAA. Optionally, the rim of the tube distal opening is pushed against the internal wall of the LAA with a force sufficient to ensure a tight sealing between the tube and the LAA. In some embodiments, the rim associated with the distal opening of the tube applies sufficient force against the internal wall of the LAA or against the internal wall of the LAA opening to anchor the tube. Alternatively, the rim of the tube distal opening is pulled towards the internal wall of the LAA. In some embodiments, the tube is elastic, for example to allow tight attachment between the tube and the LAA wall or the LA wall. Alternatively, at least part of the tube is elastic, for example the distal end of the tube facing the tissue. In some embodiments, the tube is anchored to the internal wall of the LAA by at least one anchor. Optionally, the anchor is a reversible anchor configured to be released from the tissue when the isolation process is over. In some embodiments, the tube is pulled towards the LAA wall by vacuum.

According to some embodiments, the rim associated with the tube applies force of up to 20N (Newton), for example 5N, 10N, 15N or any intermediate, smaller or larger value against the LAA wall or against the LAA opening wall, for example to anchor the tube.

An aspect of some embodiments relates to isolating and closing the LAA of an adult human by an LAA isolator. In some embodiments, the LAA is isolated from the LA and is closed by a single LAA isolator, for example a cover. In some embodiments, a distal opening of the isolator is shaped and sized to be positioned, at least partly, within LAA openings having variable sizes and/or shapes. In some embodiments, the isolator is sized and shaped to fit an LAA portion inverted at least partially into the LA. Alternatively or additionally, the isolator is sized and shaped to fit an LAA portion inverted at least partially through the distal opening into the isolator.

According to some embodiments, the LAA isolator comprises a body, optionally a tubular body having a distal opening, for example an opening facing the LAA, and a proximal opening, for example an opening facing a catheter used to deploy the isolator. In some embodiments, a distal end of the body, optionally located near the distal opening of the body, defines a two-state sealing adaptor interface. In some embodiments, the sealing adaptor interface is configured in a first state to apply a radially outward force against a wall of the LAA or the LAA opening, sufficient to anchor the body. In some embodiments, the radially outward force applied by the sealing adaptor interface is up to 20N, for example 5N, 10N, 15N or any intermediate, smaller or larger value. In some embodiments, in a second state, the sealing adaptor is configured to apply a radially inward force on an LAA portion inverted into the body.

According to some embodiments, the radially inward force applied by the sealing adaptor on the inverted portion of the LAA is adjusted not to cause necrosis of the LAA. Alternatively, the radially inward force applied by the sealing adaptor on the inverted portion of the LAA is adjusted to cause necrosis of the LAA. A possible advantage of applying force to cause necrosis of LAA tissue is the ability to damage or ablate LAA tissue which generates or delivers unwanted electric pulses.

According to some embodiments, the body does not comprise a proximal opening. In some embodiments, a manipulation tool or an inverting tool is introduced into the LAA through pores in the body, for example pores in a body made of a mesh. Alternatively an inverting tool, for example a cap of an inverting tool is attached to the outer surface of the body, for example a porous body. In some embodiments, the inverting tool attached to the outer surface of the porous body applies vacuum, for example to invert at least part of the LAA through the pores of the body.

According to some embodiments, the sealing adaptor defines a circumferential groove in the body that is shaped and sized to be positioned in LAA openings with variable sizes and shapes, for example in LAA openings having a maximal dimension in a range of 0.1 mm to 30 mm, for example 0.5 mm, 5 mm, 15 mm, 20 mm or any intermediate, smaller or larger value. In some embodiments, the two-state sealing adaptor deforms the LAA wall or the LAA opening wall to fit the external shape of the body, for example to fit the LAA wall or the LAA opening wall to the circumferential groove. In some embodiments, the body is partly in contact with the LAA wall or the LAA opening wall, having a gap of up to 2 mm between the external surface of the body and the LAA wall or the LAA opening wall, for example a gap of 0.1 mm, 0.5 mm, 1 mm or any intermediate, smaller or larger value.

According to some embodiments, the body is a self-expandable body configured to self-expand upon deployment from a catheter. Optionally, the sealing adaptor is self-expandable is said first state. In some embodiments, the sealing adaptor contracts, optionally irreversibly contracts on an inverted portion of the LA in response to an external force applied on the body or on the sealing adaptor. In some embodiments, the body and/or the sealing adaptor are self-collapsible. In some embodiments, the body and/or the sealing adaptor are configured to expand and to apply force against the LAA wall or the LAA opening wall in response to an external force. In some embodiments, a first external force is applied in one direction on the body or the sealing adaptor to expand the body and/or to apply force against the LAA wall or the LAA opening wall. In some embodiments, a second external force is applied in a second direction, optionally in an opposite direction on the body or on the sealing adaptor to collapse, optionally irreversibly collapse the body on the inverted portion of the LAA.

According to some embodiments, the body is configured to collapse into a disc-shaped structure. In some embodiments, the disc-shaped structure has a width of up to 15 mm, for example 5 mm, 10 mm, 12 mm or any intermediate, smaller or larger value. In some embodiments, the disc-shaped structure is shaped and sized to cover the LAA opening. In some embodiments, the disc-shaped structure has a diameter of at least 1 cm, for example 1 cm, 2 cm, 3 cm or any intermediate, smaller or larger value.

According to some embodiments, the body comprises at least two rings, optionally associated with the distal opening of the body. In some embodiments, at least one ring is an elastic ring configured to self-expand and to anchor the body within the LAA opening or the LAA. In some embodiments, at least one of the rings, for example a different ring is an elastic ring configured to self-collapse and to optionally to constrict or tighten the body, or a portion of the body, for example a distal opening of the body on an inverted portion of the LAA. In some embodiments, application of an external force on the at least one self-expanding elastic ring irreversibly collapses the ring. In some embodiments, the at least two rings and the isolator and/or the body are positioned on a similar axis. In some embodiments, the at least two rings are not spaced-apart from the body.

According to some embodiments, the body comprises at least one adjustable elastic ring, optionally associated with a distal opening of the body. In some embodiments, the at least one adjustable ring is self-expandable configured to self-expand and anchor the body at least partly within an LAA opening or at least partly within the LAA. In some embodiments, the at least one ring collapses, optionally irreversibly collapses on an inverted portion of the LAA positioned within the body, in response to an external force applied on the at least one ring.

According to some embodiments, the body comprises at least one adjustable elastic ring, optionally associated with a distal opening of the body. In some embodiments, the at least one ring is self-collapsible. In some embodiments, application of an external force on the at least one elastic ring expands the ring to make contact with the LAA opening wall or the LA wall. In some embodiments, the at least one ring collapses on an inverted portion of the LAA, for example when application of the external force is stopped.

According to some embodiments, a portion of the body optionally associated with the proximal opening is self-collapsible configured to collapse and close the proximal opening when the isolator disconnects from a delivery system, for example a catheter used to deploy the isolator. In some embodiments, the body comprises at least one ring associated with the proximal opening. In some embodiments, the at least one ring is an adjustable ring, configured to constrict and close the proximal opening in response to an external force applied on the ring.

According to some embodiments, one or more of the rings associated with the body, as discussed herein are lasso rings or lasso loops, configured to expand and/or constrict in response to an external force applied by a wire connected to the ring. In some embodiments, at least some of the rings and the body are positioned on the same axis or on the same plane. Optionally, all the rings associated with the body and the body are positioned on the same axis or on the same plane. In some embodiments all of the rings are co-planar. In some embodiments, some or all of the rings associated with the body and the body are co-planar. In some embodiments, the rings are not spaced-apart from the body.

According to some embodiments, at least one ring associated with the body, for example a porous body, or a mesh body is positioned around and on top of the body. Alternatively, the at least one ring is positioned under the body, for example under the mesh body. Optionally, the at least one ring is interlaced within the body.

According to some embodiments, the body is a non-porous body. In some embodiments, the body comprises a mesh having a plurality of openings. In some embodiments, a maximal dimension of the openings is up to 200 microns, for example 10 microns, 50 microns, 100 microns or any intermediate, smaller or larger value. In some embodiments, an axial length of the body in a fully expanded state is up to 4 cm from the LA wall, for example up to 2 cm, 3 cm, 4 cm or any intermediate, smaller or larger value from the LA wall.

According to some embodiments, the body is self-collapsible, optionally formed from a memory shape alloy, for example nitinol. In some embodiments, in a collapsed state, the body is positioned at a maximal distance of up to 15 mm, for example 3 mm, 5 mm, 8 mm from the LA wall. In some embodiments, a maximal dimension of the body, for example diameter, in a collapsed state is up to 4 cm, for example 1 cm, 1.5 cm. 2 cm or any intermediate, smaller or larger value.

An aspect of some embodiments relates to closing the LAA by a ring having at least one anchor. In some embodiments, at least one section of the LAA is partly or fully inverted into the LA lumen. Alternatively, the inverted section of the LAA remains inside the LAA. In some embodiments, the ring is shaped and sized to be wrapped around and anchored to the inverted section of the LAA. In some embodiments, after the LAA is inverted, the ring is positioned and fastened around the inverted section of the LAA, for example to close the inverted section. In some embodiments, when the ring is fastened, the ring anchor penetrates into the LAA wall to make sure that the ring will not be opened or detached from the LAA. In some embodiments, the ring is anchored to the LAA wall with a force that does not tear the LAA, for example with a force of up to 7 Kg using a lasso with 0.7 mm wire. In some embodiments, the anchor comprises at least one pin or at least one hook or any type of structure shaped to enter into the LAA wall in a way that prevents the release of the ring from the LAA wall.

According to some exemplary embodiments, the ring or any other fastening element, for example a lasso or a clip is fastened around the inverted LAA. In some embodiments, the fastening element is fastens the inverted LAA in a distance of up to 40 mm from the LA wall, for example 5, 10, 15, 20 mm or any intermediate larger or smaller distance from the LA wall. In some embodiments, is optionally an elastic ring with an adjustable diameter. In some embodiments, the ring is positioned around the isolator, for example a tube, a cover, or a mesh. Optionally, the ring surrounds the isolator and fastens the isolator to the inverted LAA. Alternatively, the ring is fastened around the inverted LAA, and is optionally positioned in a distance of at least 0.5 mm from the isolator, for example 0.5, 1, 1.5, 5 mm or any intermediate or larger distance from the isolator. In some embodiments, the isolator is positioned around the ring.

An aspect of some embodiments relates to closing a partially inverted LAA. In some embodiments, at least part of the LAA is inverted into the LA. Alternatively, at least part of the LAA is inverted and remains in the LAA. In some embodiments, a plug, for example an occluder, is positioned inside the LAA and is optionally in contact with the partially inverted LAA. Alternatively, a plug or a cover is connected to the inverted section of the LAA placed inside the LA. A possible advantage of closing a partially inverted LAA is that it allows multiple anchoring points between the plug and the LAA wall that remain within the heart lumen and do not penetrate through the heart wall to the outside, and therefore minimizes the risk of blood leakage from the heart.

In some embodiments, the LAA is partially inverted in at least one section, for example 1, 2, 3, 4, 5 sections or any larger number of sections. In some embodiments, the inverted sections of the LAA remain inside the LAA lumen. Alternatively, some or all of the inverted sections enter at least partially into the LA. In some embodiments, the LAA wall is inverted by application of vacuum on the LAA wall, for example a vacuum force of up to 1 atmosphere suction. In some embodiments, the LAA wall is inverted by inserting at least one screw or at least one pin into the LAA wall and pulling the LAA wall towards the LA.

An aspect of some embodiments of the invention relates to anchoring a plug or a device positioned inside the LAA to at least one inverted section of the LAA. According to some embodiments, at least one inverted section of the LAA is closed by a fastening element, for example in the form of a loop. Some examples for a fastening element comprise a lasso, a wire, a ring, or a clip. In some embodiments, the fastening element serves as an anchoring point for other devices. In some embodiments, a device that anchors against the LAA wall or a cover that is placed in the LA can be connected to the fastening element or directly to the inverted LAA.

According to some embodiments, a device, for example a cap for isolating the LAA from the LA is anchored to at least one, optionally at least two inverted portions of the LAA. In some embodiments, the at least two inverted portions are positioned within the LAA lumen. In some embodiments, the at least one inverted portion of the is inverted using an inverting element, for example by application of vacuum of the LAA wall and/or by a grasping member, as described herein. In some embodiments, at least two LAA anchors are attached to the at least one inverted portion of the LAA. Optionally, each of the at least two inverted portions of the LAA are connected to a separate anchor. In some embodiments, the anchors comprise a fastening element as described above. In some embodiments, the device, for example the cap is connected to at least one of the anchors by a wire. In some embodiments, the device is shaped and sized to be positioned at least partly within the LAA. In some embodiments, the device is shaped and sized to cover the LAA opening.

According to some embodiments, the device comprises a plurality of pores having a maximal dimension of up to 200 microns, for example 20 microns, 50 microns, 100 microns, 150 microns or any intermediate, smaller or larger value.

An aspect of some embodiments relates to reshaping the LAA by covering at least part of an inverted LAA. In some embodiments, covering of at least part of the inverted LAA traps blood clots or debris released from the LAA. In some embodiments, the cover applies a shrinking force on the inverted LAA In some embodiments, at least part of the LAA is inverted into the LA and covered. In some embodiments, the inverted section of the LAA is covered by a sealed cover that does not allow any blood flow towards the covered LAA. Alternatively, the inverted LAA is covered by a permeable or a semi-permeable cover, that optionally allows blood to flow from the LA to the covered LAA but does not allow LAA tissue debris to penetrate into the LA. In some embodiments, the permeable or semi-permeable cover comprises a mesh having a plurality of pores in a size range of 80-130 microns ($\mu$m). In some embodiments, the permeable or semi-permeable cover comprises a mesh having a plurality of pores having a maximal dimension of up to 200 microns, for example 10 microns, 50 microns, 100 microns, 150 microns or any intermediate, smaller or larger value.

According to some embodiments, a catheter that inverts at least part of the LAA, covers the inverted section with the cover. Alternatively, a catheter vacuum is inserted into the LAA through the catheter and a different device deploys the cover on top of the inverted section.

According to some embodiments, the cover is pre-shaped, and optionally is made from a memory alloy, for example Nitinol. In some embodiments, as the tissue between the cover and the LA wall shrinks, the cover returns to its original pre-shape structure. In some embodiments, the pre-shape is a disc that presses the LAA tissue against the LA wall, or brings it closer to the LA wall. A possible advantage of having a pre-shaped cover that return to its original disc shape is that it allows to adjust the cover to the inner surface of the LA wall. This allows to have minimal interference with blood flow in the LA.

An aspect of some embodiments relates to attaching an inverted part of the LAA to the LA wall. In some embodiments, the inverted part of the LAA is attached to the LA wall by a cover or a sealing element, for example a sealing cap that pushes the inverted LAA to the LA wall. Alternatively, the cover or the sealing element brings the inverted LAA closer to the LA wall. In some embodiments, anchors on the cover or on the sealing element prevent the detachment of the LAA from the LA wall.

In some embodiments, a cover or a sealing cap is attached to the LA wall around the LAA opening, for example to isolate the LAA from the LA. Optionally, the cover is deformed to act as a cap, for example when the cover is made from a shape-memory metal alloy. In some embodiments, at least part of the LAA is inverted into the LA lumen as describe above. In some embodiments, the cover or the sealing cap are pushed against the LA wall, leading to the attachment of the LAA to the LA. Alternatively, the cover or the sealing cap is pulled towards the LA wall. In some embodiments, the cover is a sealed cover that prevents any blood flow between the LA and the covered part of the LAA. Alternatively the cover is a permeable or a semi-permeable cover that optionally allows blood to flow from the LA to the covered LAA but does not allow LAA tissue debris to penetrate into the LA. In some embodiments, the permeable or semi-permeable cover comprises a mesh having a plurality of pores in a size range of 80-130 microns (μm). In some embodiments, the permeable or semi-permeable cover comprises a mesh having a plurality of pores having a maximal dimension of up to 200 microns, for example 10 microns, 50 microns, 100 microns, 150 microns or any intermediate, smaller or larger value. In some embodiments, the cover is an elastic cover shaped to cover varying sizes and/or volumes and/or shapes of the inverted LAA positioned inside the LA.

According to some embodiments, the cover comprises at least one anchor for anchoring the cover to the LA wall and optionally through the covered LAA wall. In some embodiments, the anchor comprises at least one hook or pin sized and shaped to penetrate through the LA wall.

In some embodiments of the invention, a system for closing the LAA comprising a catheter with an elongated body surrounded by a cover, and a self-expandable isolator, for example a mesh positioned inside the lumen of the elongated body. In some embodiments, for example when the catheter is inserted into the LA and positioned near the LAA opening, the catheter body or cover is retracted and exposes the isolator. In some embodiments, the isolator is surrounded with a constraining element, for example a ring or a tubular cover that prevents the expansion of the isolator upon exposure. In some embodiments, the distal opening of the isolator and the constraining element is inserted at least 1 mm into the LAA. Alternatively, the distal opening of the isolator is placed near to the LAA opening.

In some embodiments, the constraining element is retraced into the lumen of the catheter, for example to allow the expansion of the isolator. In some embodiments, expansion of the isolator within the LAA anchors the isolator by applying force against the inner surface of the LAA. Alternatively, following expansion outside of the LAA the distal opening of the isolator is pushed against the LA wall surrounding the LAA opening.

In some embodiments, an inverting element is inserted into the LAA, and inverts at least part of the LAA into the isolator. In some embodiments, the inverted LAA is inserted at least 2 mm, for example 2, 4, 6, 8 mm or any intermediate or larger distance into the LAA. In some embodiments, when the inverted LAA is positioned in a desired location within the LAA, a closing mechanism for example a loop surrounding the distal opening of the isolator is fastened. In some embodiments, fastening the closing mechanism attaches the isolator at least partially to the inverted LAA. In some embodiments, the closing mechanism is fastened by pulling a wire optionally in an axial direction towards the catheter lumen. In some embodiments, the wire is connected to the closing mechanism in a collapsible connection that allows, for example the detachment of the wire from the closing mechanism when the wire is pulled with a specific force. In some embodiments, upon activation of the specific force, the wire detaches from the closing mechanism and pulled into the catheter lumen.

In some embodiments, the inverting element is retracted into the lumen following the fastening of distal opening of the isolator to the inverted LAA. In some embodiments, a closing mechanism is advanced to close the proximal opening of the isolator, for example by a clip or suture. Alternatively, a closing element is pulled from within the isolator through the proximal opening to close the proximal opening. In some embodiments, when the proximal opening is closed the catheter is retracted out from the LA.

An aspect of some embodiments relates to placing an isolator, for example an isolating cover or a cover at least partly within the LAA by adjusting the distal opening of the cover to the shape and/or the size of the LAA opening. In some embodiments, a sealing adaptor, for example a sealing adaptor interface is positioned near or around the distal opening of the cover, optionally as part of the cover. Alternatively, the sealing adaptor is associated with a proximal opening of the isolator. In some embodiments, the sealing adaptor comprises at least two adjustable elements. In some embodiments, each of the sealing adaptors is configured to contract and/or expand independently from the rest of the adjustable elements of the sealing adaptor.

According to some embodiments, the sealing adaptor comprises at least two adjustable rings, for example 2, 3, 4, 5, 6 rings or any intermediate, smaller or larger number of rings. In some embodiments, at least some of the rings are configured to contract and/or expand independently from other rings, optionally adjacent rings, of the same cover. In some embodiments, contraction of the adjustable rings reduces the diameter of the distal opening of the cover. In some embodiments, expansion of the adjustable rings increases the diameter of the distal opening. In some embodiments, expansion of the sealing adaptor comprising the rings within the LAA opening allows, for example for each of the rings to expand to a different diameter according to the shape and diameter of the LAA opening.

According to some embodiments, the sealing adaptor interface is defined by the isolator. In some embodiments, the sealing adaptor interface is a two state sealing adaptor interface configured in a first state to anchor the isolator within an LAA opening or within the LA wall and in a second state to collapse on an inverted portion of the LAA. In some embodiments, the rings and or the sealing adaptor defines a circumferential groove in the external surface of the isolator. In some embodiments, the circumferential groove is shaped and sized to fit LAA openings with varying sizes and shapes. In some embodiments, the isolator fits into LAA openings having a maximal dimension in a range of 0.1 mm to 25 mm, for example 0.5 mm, 1 mm, 5 mm, 10 mm, 15 mm or any intermediate, smaller or larger value.

A possible advantage of some embodiments of the invention is that the isolator as described herein fits LAA openings with different sizes and/or shapes, without the need of prior-measurements of the LAA or numerous insertions of LAA closure devices into the heart.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Process for Isolating the LAA from the LA

According to some exemplary embodiments, the LAA lumen may include blood clots or tissue debris that can enter the LA, travel to the brain and cause stroke. This is extremely important in atrial fibrillation patients that are considered to be in high risk for forming blood clots. In some embodiments, in order to prevent the release of blood clots from the LAA, the LAA is isolated from the LA prior to any manipulation of the LAA, for example before and/or during any manipulation within the LAA lumen. Reference is now made to FIG. 1 describing a process for isolation of the LAA, according to some embodiments of the invention.

According to some exemplary embodiments, a catheter is inserted into the LA at 102. In some embodiments, the distal section of the catheter is inserted through an opening in the septum between the atria, into the LA.

According to some exemplary embodiments, the LAA is isolated from the LA at 104. In some embodiments, a tube is deployed through the catheter and into the LAA opening. In some embodiments, when the tube is positioned inside the LAA opening, then the outer surface of the tube placed inside the LAA is in contact at least partially with the inner surface of the LAA wall. Alternatively, if the diameter of the tube is larger than the diameter of the LAA opening, the tube is positioned in contact with the LA wall. In some embodiments, the tube distal opening surrounds the LAA opening. In some embodiments, at least part of the tube, for example the distal part of the tube facing the LA wall is flexible and/or elastic. In some embodiments, at least part of the tube is flexible and/or elastic to allow optimal adjustment of the distal part of the tube to the LA wall surrounding the LAA opening. In some embodiments, when the tube is pushed or pulled into the LAA opening the flexible and/or distal part of the tube allows, for example to better fit the tube inside the LAA opening. In some embodiments, the proximal opening of the tube is placed within the catheter lumen and allows for example to deliver blood clots and debris from the LAA outside of the body, optionally by applying vacuum.

According to some exemplary embodiments, the LAA is isolated by positioning a flexible cover over the LAA opening inside the LA. Alternatively, the flexible cover is positioned inside the LAA, and contacts at least part of the LAA inner surface with sufficient force to prevent any leakage from the LAA. In some embodiments, the cover impermeable to blood flow between the LA and the LAA. Alternatively, the cover is semi-permeable optionally in the form of a mesh and allows, for example blood to flow between the LA and the LAA flow but prevents the release of blood clots or tissue debris from the LAA. In some embodiments, the proximal opening of the tube is placed within the catheter lumen and allows for example to deliver blood clots and debris from the LAA outside of the body, optionally by applying vacuum.

According to some exemplary embodiments, the LAA is manipulated at 106. In some embodiments, the LAA is manipulated by catheters inserted into the LAA lumen, for example vacuum catheters or brushes used to clean the LAA lumen. In some embodiments, the LAA is manipulated from outside the heart, for example when a lasso is wrapped around the outer surface of the LAA wall.

According to some exemplary embodiments, a plug is positioned inside the LAA at 110. In some embodiments, the plug is anchored by pressing against the inner surface of the LAA wall and/or to a disk placed in the LA, for example a WATCHMAN™ device or an AMPLATZER™ device or a Lambre™ device. According to some exemplary embodiments, the LAA isolation is removed at 112. In some embodiments, the isolation is removed only when the LAA manipulation is over and/or after a plug is positioned. In some embodiments, the tube, the cover or the mesh are retracted into the catheter lumen.

According to some exemplary embodiments, the catheter is retracted from the LA at 114.

Exemplary Process for Placing a Cover Over a Part of the LAA

Figure 2:
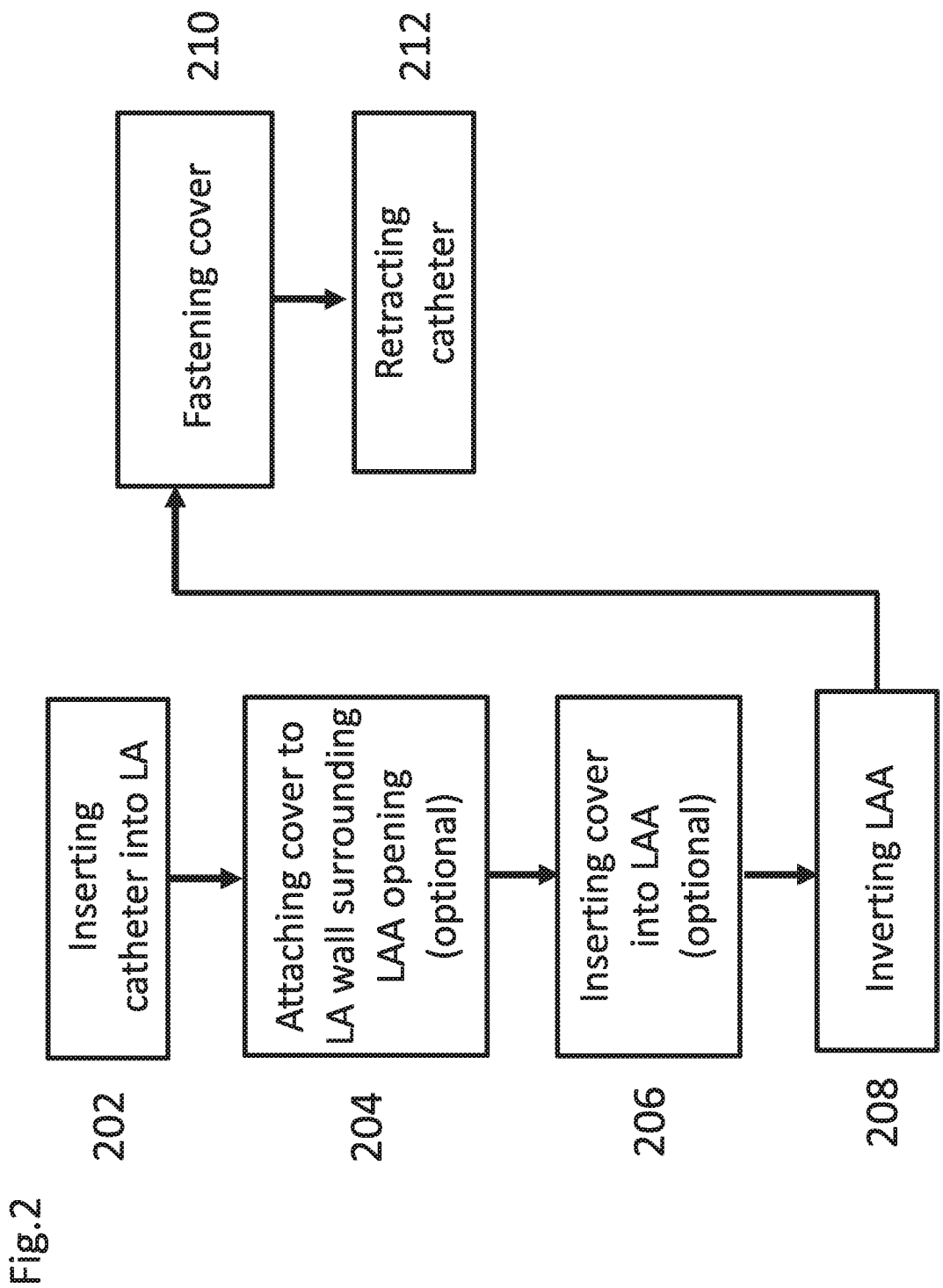
FIG. 2 is a flow chart describing a process for applying a cover over at least part of the LAA.

According to some exemplary embodiments, the LAA is closed by wrapping a cover around an inverted section of the LAA and by tightly attaching the LAA walls to each other. A possible advantage of covering inverted parts of the LAA is that it prevents the entry of blood clots from the LAA into the LA. Reference is now made to FIG. 2 describing a process for covering at least part of the LAA, according to some embodiments of the invention.

According to some exemplary embodiments, a catheter is inserted into the LA at 202. In some embodiments, the catheter is inserted as previously described at 102.

According to some exemplary embodiments, an elastic cover is attached to the LA wall surrounding the LAA opening at 204, for example to isolate the LA from the LAA lumen. In some embodiments, the cover is anchored to the LA wall by at least one anchor, for example to prevent the detachment of the cover from the LA wall, and to prevent leakage of blood clots from the LAA into the LA. Alternatively, the cover is inserted and deployed inside the LAA at 206. In some embodiments, the outer surface of the cover is in contact with the inner surface of the LAA wall. Optionally, the cover is anchored to the inner surface of the wall. In some embodiments, the cover comprises a mesh with pores that allow, for example blood flow through the mesh but not blood clots or debris with a size of 80 microns ($\mu m$) and larger. In some embodiments, the cover comprises a ring or a lasso loop attached to the circumference of the distal opening of the cover.

According to some exemplary embodiments, at least part of the LAA is inverted at 208. In some embodiments, a plurality of sections of the LAA are inverted, for example 2, 3, 4, 5, optionally simultaneously. In some embodiments, the LAA is inverted at least partly into the LA. Alternatively, the inverted sections of LAA remain inside the LAA lumen, and do not penetrate into the LA. In some embodiments, the LAA is completely inverted into the LA. Optionally, at least 80% of the LAA is inverted into the LA, for example 80%, 90%, 95%, 100% or any intermediate or smaller percentage of the LAA is inverted into the LA.

In some embodiments, at least one vacuum head is inserted into the LAA and contacts the LAA wall. In some embodiments, the vacuum head pulls at least part of the LAA wall towards the LA using vacuum suction. Alternatively, an elongated element, for example a flexible shaft, a rod or a catheter is inserted into the LAA. In some embodiments, the elongated element is connected to the LAA wall by inserting an anchor for example at least one pin, a screw or a hook into the LAA wall. In some embodiments, the elongated element is retracted out from the LAA, pulling the LAA, which causes the LAA to be at least partly inverted.

According to some exemplary embodiments, the inverted section of the LAA held by the vacuum or the anchor is pulled into the distal opening of the cover and through the ring or the lasso surrounding the distal opening.

According to some exemplary embodiments, the cover is fastened around the inverted section of the LAA at 210. In some embodiments, the distal opening of the cover is fastened around the inverted section of the LAA that is positioned inside the cover. In some embodiments, if the LAA is fully inverted into the LA, then the distal opening of the cover is fastened proximally to the LAA base, optionally near the LA wall.

According to some embodiments, the distal opening of the cover is fastened by fastening the ring or a lasso around the inverted LAA. In some embodiments, the ring comprises at least one anchor that penetrates into the LAA wall when the ring is tightened. In some embodiments, the anchor is connected with sufficient force and/or in a way that prevents the opening of the ring. In some embodiments, the lasso wire is wrapped around the inverted LAA and is tied, for example to close the inverted LAA and optionally to prevent the detachment of the cover from the inverted LAA.

According to some exemplary embodiments, the catheter is retracted from the LA at 212. In some embodiments, the proximal opening of the cover that was positioned in the catheter lumen is closed. In some embodiments, when the catheter is retracted through the proximal opening of the cover, a closing element, for example a clip closes the opening. Alternatively, a lasso or at least one ring positioned around the proximal opening contracts and closes the proximal opening. In some embodiments, the ring is made from a memory shape alloy, for example Nitinol.

Exemplary Catheter for Placing a Cover Over the LAA

Figure 3A:
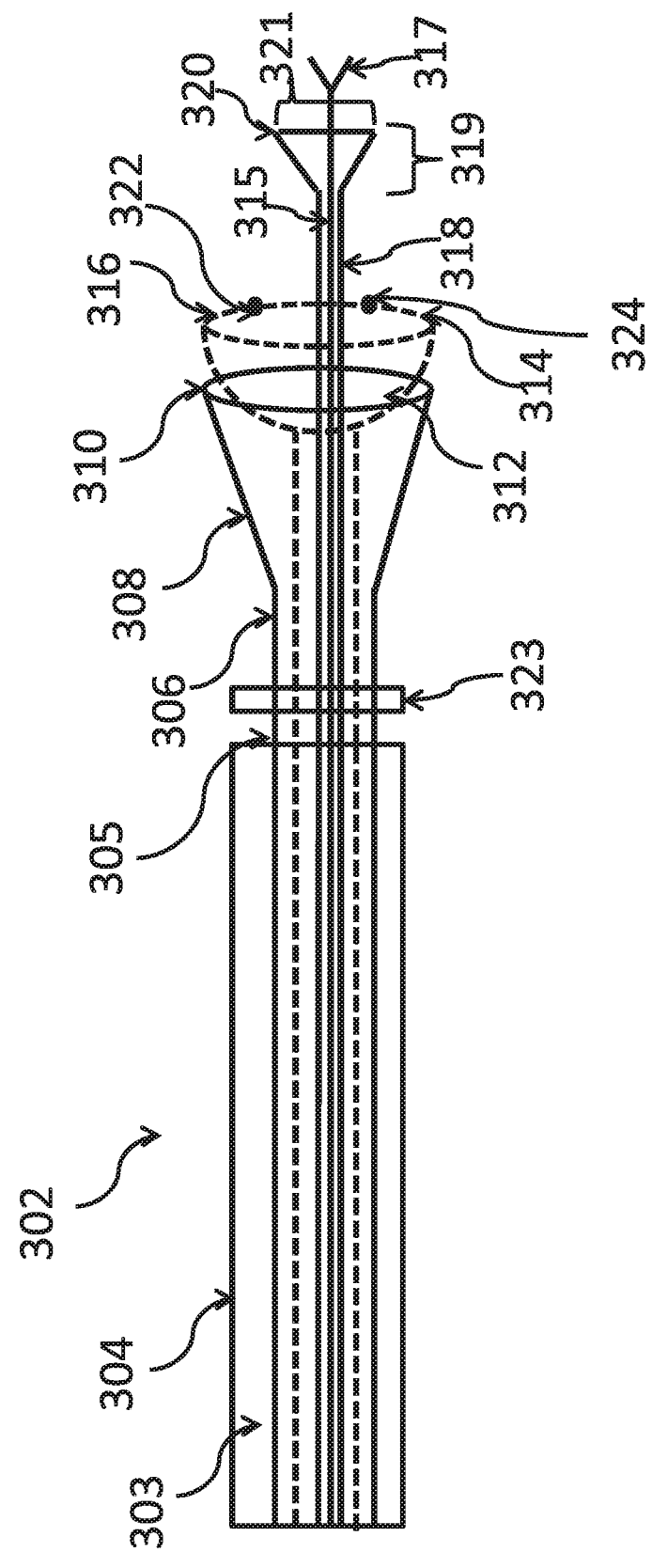
FIG. 3A is a block diagram of a device for deployment a cover over at least part of the LAA, according to some embodiments of the invention.

Reference is now made to FIG. 3A describing a device for covering at least part of the LAA, according to some embodiments of the invention.

According to some exemplary embodiments, catheter 302 comprises an elongated flexible catheter body 304. In some embodiments, catheter 302 is cylindrical and comprises an internal lumen 303 along the catheter 302 elongated axis. The catheter 302 is shaped and sized to be inserted through an opening in the septum between the right and left atria into the LA.

Exemplary Sealer with a Sealing Cap

According to some exemplary embodiments, catheter 302 comprises a sealer 306 having an elongated body positioned within the lumen 303 that is configured to be pushed or pulled into the LA through the distal opening 305 of the catheter 302. In some embodiments, sealer 306 comprises a sealing cap 308, optionally conical. In some embodiments, the sealing cap is configured to be positioned within the LA, and to be attached to the LA wall around the LAA opening. In some embodiments, the sealing a textile or sponge portion is connected to the edge of the sealing cap, and is shaped and sized to be placed in contact with the LA wall or the LAA wall. Optionally, the sealing cap edge applies force, for example radial force against the LA wall or the LAA wall. In some embodiments, a distal opening 310 of the sealing cap has a larger diameter than the diameter of the LAA opening, which has an opening with a diameter in the range of 10-40 mm. In some embodiments, the distal opening 310 of the sealing cap has a diameter of at least 10 mm, for example 10, 20, 30, 40, 50, 60 mm or any intermediate or larger diameter. In some embodiments, the sealing cap 308 is flexible, and optionally elastic around the distal opening 310, for example to allow a best fitting of the sealing cap to the LA wall.

In some embodiments, the sealer 306 is an elongated tube configured to be inserted into the LAA. In some embodiments, the distal opening 310 of the tube has a diameter which is smaller than the diameter of the LAA. In some embodiments, the catheter 302 and the sealer are two separate devices, for example when the catheter 302 forms a channel for insertion of a separate sealer device.

Exemplary Cover

According to some exemplary embodiments, an isolator, for example cover 312 is positioned at least partially within lumen 303. In some embodiments, the cover 312 is pushed or pulled through the distal opening 305 of the catheter into the LA or into the LAA. In some embodiments, the distal end 314 of the cover 312 comprises a fastening element 316 surrounding the cover distal opening. In some embodiments, the fastening element 316 controls the opening degree of the cover opening and the cover opening diameter. In some embodiments, when the fastening element expands or opened, the cover opening is opened, for example to surround tissue with large volume or size. In some embodiments, when the fastening element contracts or is closed, the cover opening closes and contacts the tissue.

According to some exemplary embodiments, the cover 312 is a mesh with pores in a size of up to 130 microns (μm), for example 130, 80, 85, 90, 95 microns or any intermediate or smaller pore size. In some embodiments, the cover 312 is a mesh having openings with a maximal dimension, for example size, diameter or width, of up to 200 microns, for example 50 microns, 100 microns, 150 microns or any intermediate, smaller or larger value. In some embodiments, the pore size does not allow the flow of blood clots through the mesh. In some embodiments, the cover is an elastic self-expandable mesh. In some embodiments, when the mesh is fully expanded, the distal opening of the mesh has a diameter in the range of 7-70 mm, for example 7, 8, 10, 20, 30, 40, 50 mm, or any intermediate or larger diameter. In some embodiments, the mesh diameter in a fully contracted conformation has a diameter of in a range of 2-20 mm, for example 2, 3, 4, 8, 9, 10 mm or any intermediate or larger diameter. In some embodiments, the mesh is made from a memory shape alloy, for example Nitinol.

According to some exemplary embodiments, the mesh is a plastic deformable mesh. In some embodiments, to expand the mesh a balloon is inflated inside the mesh. In some embodiments, when a contractible ring is placed around the mesh and contracts, the mesh structure is deformed and optionally, the mesh cannot further expand.

According to some exemplary embodiments, when the mesh is inserted at least 1 mm into the LAA, for example 1, 2, 5, 10 mm into the LAA. In some embodiments, the mesh is inserted into the LAA in a contracted conformation and expanded when deployed. In some embodiments, a ring surrounding the mesh is retracted, for example to allow the expansion of the mesh. In some embodiments, when the mesh is expanded within the LAA, the mesh applies force against the inner surface of the LAA, for example to anchor the mesh. In some embodiments, the mesh expands and applies force, for example radial force, against the LAA wall or the LAA opening wall. Alternatively, at least one ring associated with the mesh is manipulated and expands to apply force, for example radial force against the LAA wall or the LAA opening wall.

According to some exemplary embodiments, the isolator is a tube with a diameter in the range of 10-50 mm, for example 10, 20, 30, 40, 50 mm or any intermediate diameter. In some embodiments, the tube is pushed at least 1 mm into the LLA, for example 1, 2, 3, 4 mm. Alternatively, the tube is positioned in the LA around the LAA opening. In some embodiments, at least the distal end of the tube, for example the part of the tube surrounding the distal opening is elastic. In some embodiments, the elastic end of the tube allows, for example to attach the tube to the LA wall in a way that prevents leakage of blood clots from the LAA.

According to some exemplary embodiments, a fastening element 323, for example a lasso or a ring is positioned around the isolator. In some embodiments, when the isolator is deployed the fastening element surrounds the isolator, for example to limit or prevent the expansion of the isolator. In some embodiments, when the isolator, for example the mesh is inserted into the LAA, the fastening element 323 is retracted towards the catheter body 304 for example, to allow the expansion and anchoring of the isolator within the LAA. In some embodiments, when the LAA is inverted into the isolator, the ring 323 is advanced towards the LA wall and fastens the mesh around the inverted LAA.

According to some exemplary embodiments, the cover comprises at least one anchor, for example anchor 324 and/or anchor 322 positioned on the cover edge facing the tissue. In some embodiments, the anchor is inserted into the LA or LAA wall, for example to make sure that the cover 312 is firmly attached to the tissue. Optionally, the anchor is configured to allow reversible anchoring, for example by manipulation of the anchor using a control unit or handle of the catheter, optionally to allow detachment of the cover from the tissue. In some embodiments, the anchor comprises a hook, a pin, a screw, or a thread shaped and sized, to be inserted into the LA or LAA wall, for example in a way that prevents the release of the cover from the wall. Alternatively, the anchor comprises a ring with holes that can apply vacuum to attach or to be inserted into the LA or LAA wall, for example in a way that prevents the release of the cover from the wall.

In some embodiments, a tissue inverting element 318 is inserted through lumen 303 into the LA or into the LAA. In some embodiments, the inverting element 318 comprises an elongated flexible body, for example to allow steering into narrow sections of the LAA.

In some embodiments, the inverting element 318 is a vacuum catheter having a vacuum head 320 at the distal end facing the tissue. In some embodiments, the vacuum head 320 is elastic and/or foldable, for example to allow its insertion and steering through the lumen 303 of catheter 302 into the LAA. Optionally, the elasticity of the vacuum head allows for example, better adjustment of the vacuum head to varying sizes and/or shapes of the LAA.

In some embodiments, the inverting element 318 is a flexible elongated device, for example, a rod or a shaft inserted into the LAA. In some embodiments, the flexible elongated device is configured to be attached to a section of the LAA wall, by insertion of an anchor through the internal LAA wall. In some embodiments, the anchor comprises a pin, a hook, or a screw. In some embodiments, once the anchor is placed inside the LAA wall, the flexible elongated device is retracted towards the LA while pulling and inverting at least part of the LAA. In some embodiments, the anchor is connected to the LAA wall in a reversible connection that allows to release the anchor from the LAA wall.

According to some exemplary embodiments, the vacuum head 320 has a conical shape with an oval or a round distal opening facing the tissue. In some embodiments, a width 321 and/or a diameter of the distal opening is in a range of 0.3-2 cm, for example 0.3 cm, 0.5 cm, 1 cm or any intermediate, smaller or larger value. In some embodiments, a length 319 of the vacuum head is in a range 0.3-3 cm, for example 0.3 cm, 0.5 cm, 1 cm, 1.5 cm or any intermediate, smaller or larger value. Optionally at least a portion of the vacuum head 320 is elastic, for example the portion which is placed in contact with the LAA wall. In some embodiments, the vacuum head can be made from any biocompatible material as Teflon, rubber, plastic, Silicon or a special mesh design of Nitinol/stainless coated feature.

According to some exemplary embodiments, the vacuum head 320 is connected to a negative pressure source positioned outside the body. In some embodiments, the negative pressure source applies negative pressure of up to 1 atmospheric pressure, for example 0.2 atm, 0.5 atm, 0.8 atm or any intermediate, smaller or larger value. In some embodiments, the negative pressure is applied through the vacuum head on the internal surface of the LAA wall.

According to some exemplary embodiments, a grasping member 315 is positioned within the vacuum head 320. In some embodiments, the grasping member 315 is configured to be advanced within the tissue inverting element 318, for example within a channel of the tissue inverting element 318.

According to some exemplary embodiments, the grasping member 315 comprises a grasping head 317 at the distal end of the grasping member 315. In some embodiments, the grasping head 317 is configured to be advanced into the LAA, optionally forward and away from the vacuum head 320 and grasp a portion of the LAA wall, for example a portion of the internal surface of the LAA wall. In some embodiments, retraction of the grasping member 315 within the channel of the tissue inverting element 318 while the grasping member grasps a portion of the LAA wall, places the portion of the LAA within the vacuum head 320. A possible advantage of having a grasping member is that it allows to place portions of the LAA having one or more invaginations within the vacuum head.

According to some exemplary embodiments, the grasping head 317 is a movable grasping head configured to reversibly move between an open position and a closed position, optionally under a control of a control unit or a control handle positioned outside the body. In some embodiments, the grasping member comprises at least one pin shaped and sized to penetrate at least partially through the LAA wall. Alternatively or additionally, the grasping head 317 comprises a plurality of projections, for example teeth, or a plurality of protrusions, shaped and sized to grasp a portion of the LAA wall without penetrating through the LAA wall or tearing the LAA wall.

According to some exemplary embodiments, the catheter 302 comprises only the grasping member 315 without the vacuum head. In some embodiments, the grasping member is advanced within the lumen of the catheter 302 into the LAA lumen.

Exemplary Tissue Inverting Element

Reference is now made to FIGS. 3B-3C describing a tissue inverting element, according to some embodiments of the invention. According to some exemplary embodiments, catheter 340 comprises a cover 342 and an inverting element 346 that is pushed or pulled through the distal opening 344 of the cover 342. In some embodiments, the inverting element 346, for example as shown in FIG. 3B comprises a single inverting head 348 configured to be connected to a single section of the LAA wall. In some embodiments, this allows, for example to invert only a single section of the LAA.

According to some exemplary embodiments, the inverting element, for example inverting element 346 comprises at least two inverting heads, for example inverting heads 350, 352 and 354. In some embodiments, having at least two inverting heads allows, for example to inverts at least two sections of the LAA.

A possible advantage of inverting several sections of the LAA is that it allows better shrinkage of the LAA size and/or volume when the inverted sections are tied, for example by a lasso. In some embodiments, the inverted LAA section serves as a plug for closing the LAA opening. In some embodiments, the inverted LAA sections generate a plurality of anchoring points for LAA plugs or any device that needs to be anchored within the LAA or the LA, for example a WATCHMAN™ device or an AMPLATZER™ or a Lambre™ device.

Exemplary Cover and Fastening Mechanisms

According to some exemplary embodiments, the catheter comprises an adjustable cover with a distal opening facing the tissue that can be opened or closed. In some embodiments, when a large section of the LAA is planned to be covered, the distal opening is opened to allow the insertion of the large LAA section into the cover. In some embodiments, when the LAA section is positioned inside the cover, the distal opening is closed, for example to allow maximal contact between the cover and the LAA section.

Reference is now being made to FIGS. 3D-3G, depicting different closing mechanisms of covers.

According to some exemplary embodiments, a cover, for example cover 362 comprises a ring 364 surrounding the distal opening 365 of the cover. In some embodiments, the ring comprises at least one anchor for example, anchors 366, 368, 370 which allow the anchoring of the cover to tissue, optionally in a reversible way.

According to some exemplary embodiments, the ring 364 controls the opening degree of distal opening 365. In some embodiments, when the ring 364 is closed or contracts, for example as shown in FIG. 3D, the distal opening 365 is closed. Optionally or additionally, when the ring 364 is closed the cover 362 is collapsed. In some embodiments, when the cover 362 is collapsed it can be pushed or pulled through the lumen of catheter 360 into the LA or into the LAA. In some embodiments, when the ring 364 is opened or expanded, for example as shown in FIG. 3E, the distal opening 365 is opened. Optionally or additionally, when the ring 364 is open the cover expands, for example to allow large sections of the LAA to enter through opening 365 into the cover 362.

According to some exemplary embodiments, at least one string or wire, for example wire 363 is connected to the ring 364. In some embodiments, when the wire moves away from the cover, for example in direction 367 it contracts the ring 364 and optionally closes the distal opening 365. In some embodiments, when the wire 363 moves towards the cover, for example in direction 369, the ring 364 expands, and the distal opening 365 is opened. Alternatively, when the wire 363 moves away from the cover, the ring 364 expands and when the wire moves towards the cover the ring contracts. In some embodiments, when wire 363 is pulled it is designed to be detached from the cover.

Figure 3F:
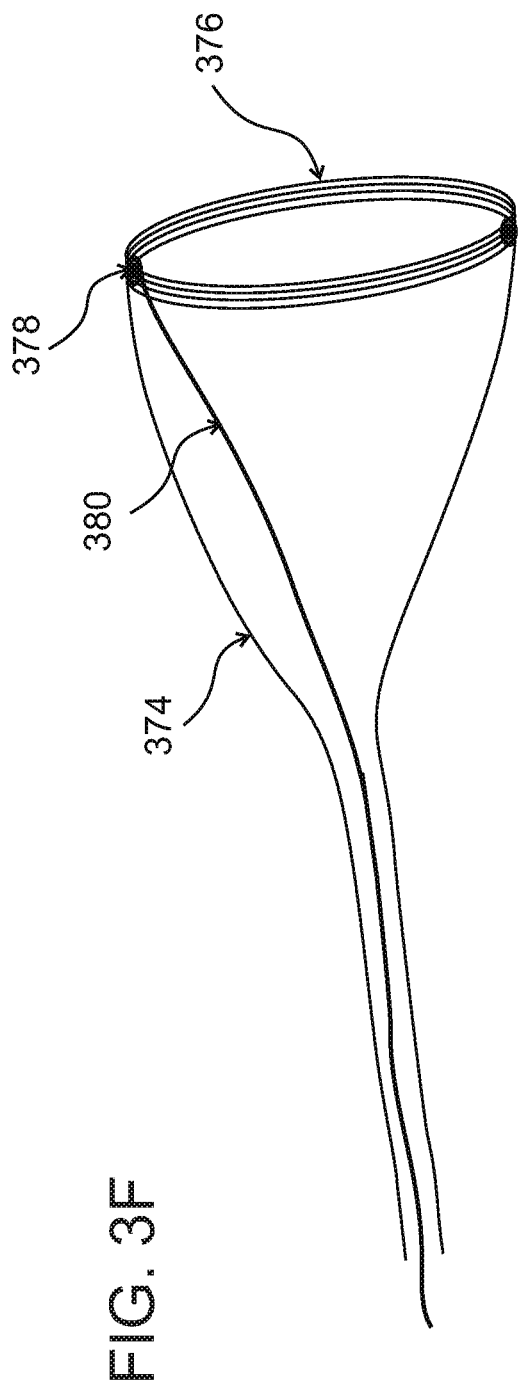
FIGS. 3F and 3G are schematic illustrations of a cover with a lasso closing mechanism, according to some embodiments of the invention.
Figure 3G:
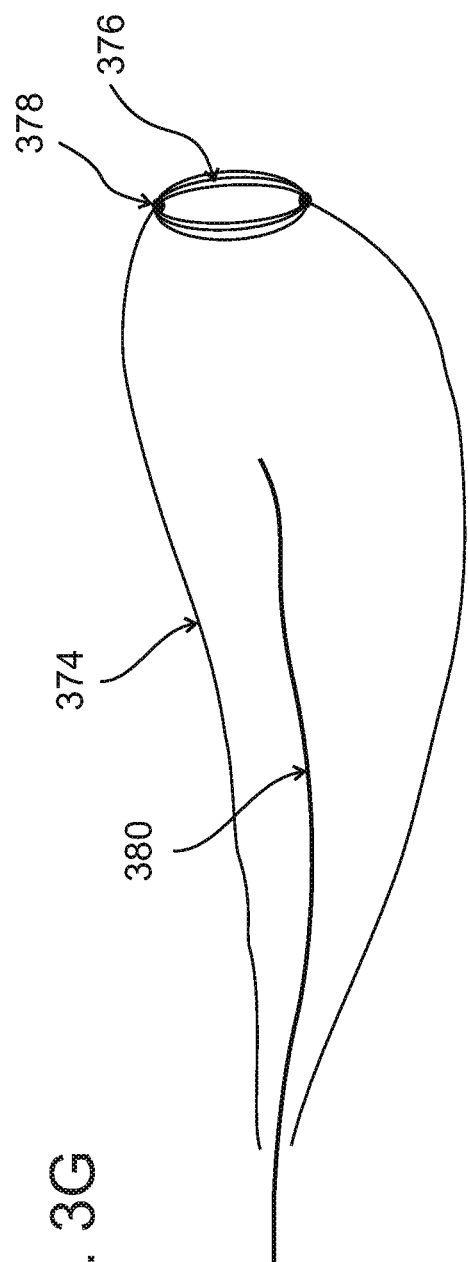

According to some exemplary embodiments, for example as shown in FIGS. 3F and 3G the cover 374 comprises a lasso 378 around the distal opening 376 of the cover. In some embodiments, the lasso 378 is connected by at least one wire 380, for example to a user, to a catheter button or to a catheter handle. In some embodiments, when wire 380 is relaxed, the lasso 378 is open, for example to allow insertion of tissue into the cover 374. In some embodiments, when the wire 380 is pulled away from the lasso 378, the lasso and the distal opening 376 is closed. In some embodiments, when the wire 380 is pulled it is designed to be detached from the lasso 378, for example to allow its removal from the body.

In some embodiments, wire 363 and wire 380 are made from an x-ray detectable material, for example to allow tracking of the wire after it is detached from the cover and/or to detect the LAA closure locations.

Reference is now made to FIGS. 3H and 3I depicting a cover with adjustable rings, according to some exemplary embodiments of the invention.

According to some exemplary embodiments, a cover, for example cover 371 comprises at least 2 rings near or around a distal opening of the cover, for example 2 rings, 3 rings, 4 rings or any intermediate or larger number of rings near or around the distal opening of the cover. In some embodiments, the most distal ring, for example distal ring 375 is positioned around the distal opening 360 of the cover 371. In some embodiments, a proximal ring, for example proximal ring 379 is positioned around the cover 371 in a distance of up to 5 mm, for example 1 mm, 2 mm, 3 mm, 4 mm, 5 mm or any intermediate, smaller or larger value from the distal opening 369 of the cover 371. In some embodiments, an additional ring, for example ring 377 is positioned between the distal ring 375 and the most proximal ring 379. In some embodiments, the distance between the rings is at least 0.5 mm, for example 0.5 mm, 1 mm, 1.5 mm, 2 mm, 2.5 mm or any intermediate, smaller or larger value.

According to some exemplary embodiments, at least some of the rings are adjustable rings, capable of adjusting their width or diameter. In some embodiments, some of the rings have an expansion range larger than the other rings, for example rings 375 and 379 have a larger expansion range compared to the ring 377 positioned between them. Optionally, the most distal ring, for example ring 375 and the most proximal ring 379 expand to a greater size that all or some of the rings positioned between them. In some embodiments, at least some of the rings are configured to expand and contract independently from the rest of the rings. In some embodiments, at least some of the rings are made from a shape memory alloy, for example Nitinol.

According to some exemplary embodiments, at least one wire, for example wire 381 is connected to one or more of the rings. In some embodiments, moving the wire allows, for example to contract or expand at least some of the rings. In some embodiments, for example as shown in FIG. 3I, pulling the wire 381 contracts at least some of the rings and optionally detaches the wire 381 from the rings.

Exemplary Process for Closing the LAA

Reference is now made to FIG. 3J describing a process for closing the LAA, according to some embodiments of the invention.

According to some exemplary embodiments, a catheter is inserted into the LA at 382. In some embodiments, the catheter is inserted into the LA through an opening in the septum between the atria.

According to some exemplary embodiments, the LAA is isolated at 384. In some embodiments, the LAA is isolated to prevent the entry of blood clots from the LAA into the LA. In some embodiments, the LAA is isolated by positioning an isolator, for example a cover at least partly inside the LAA, and/or at least partially inside the LAA opening or over the LAA opening in the LA. In some embodiments, a sealing cap is attached to the LA wall surrounding the LAA opening.

According to some exemplary embodiments, when placing the cover at least partially within the LAA or the LAA opening, the external surface of the cover applies force against the internal surface of the LAA or against the internal surface of the LAA opening, for example to isolate the LAA from the LA. Optionally, at least some of the rings, for example the rings shown in FIGS. 3H and 3I expand and apply force against the internal surface of the LAA and/or against the LAA opening.

According to some exemplary embodiments, blood clots in the LAA are removed by vacuum at 386 or by applying negative pressure within the cover. In some embodiments, a vacuum head is inserted into the LAA and removes the blood clots by applying negative pressure, for example by applying vacuum.

According to some exemplary embodiments, the LAA is inverted at 388. In some embodiments, at least one section of the LAA is inverted, optionally into the LA. In some embodiments, the LAA is inverted by pulling the LAA wall using vacuum. Alternatively, an anchor for example a pin or a hook is inserted into the LAA wall, and used for pulling the LAA towards the LA. In some embodiments, a grasping member which optionally comprises a plurality of teeth extends into the LAA and grasps a section of the LAA wall. In some embodiments, retraction of the grasping member, for example into a catheter lumen inverts the portion of the LAA into the LA. In some embodiments, the inverted LAA section remains at least partially in the LAA. Alternatively, at least part of the inverted section is inserted into the LA.

According to some exemplary embodiments, blood clots are removed by the isolator at 390. In some embodiments, blood clots that were released when the LAA is inverted are trapped by the isolator and/or are directed through a proximal opening of the isolator outside of the body through the lumen of the catheter.

According to some exemplary embodiments, the inverted section of the LAA is closed at 392. In some embodiments, the inverted section of the LAA is closed by at least one ring, or at least one clip placed around the LAA and fastened. Alternatively, the inverted section is closed by a lasso tightened around the LAA, optionally around the base of the LAA.

According to some exemplary embodiments, the isolator is removed from the LA at 394. In some embodiments, the closed LAA remains uncovered inside the LA. Alternatively, the isolator is pushed or pulled against the LA wall and traps the inverted LAA between the isolator and the LA wall. Alternatively, the isolator for example a cover collapses and traps the inverted LAA within the cover.

According to some exemplary embodiments, a proximal opening of the cover is closed at 395. In some embodiments, the proximal opening of the cover is closed by at least one ring positioned around the proximal opening. In some embodiments, the at least one ring contracts, for example to close the proximal opening of the cover. Alternatively, the proximal opening is closed by at least lasso wire tightened around the proximal opening. In some embodiments, the proximal opening of the cover is closed by advancing a ring towards and around the proximal opening. Optionally the advanced ring is configured to contract and close the proximal opening.

According to some exemplary embodiments, the catheter is retracted from the LA at 396. In some embodiments, the catheter is retracted while closing the proximal opening at 395.

Exemplary Covering the LAA

According to some exemplary embodiments, in order to prevent the release of blood clots from the LAA into the LA, which may lead to a stroke, an LAA closure procedure is performed.

Figure 4:
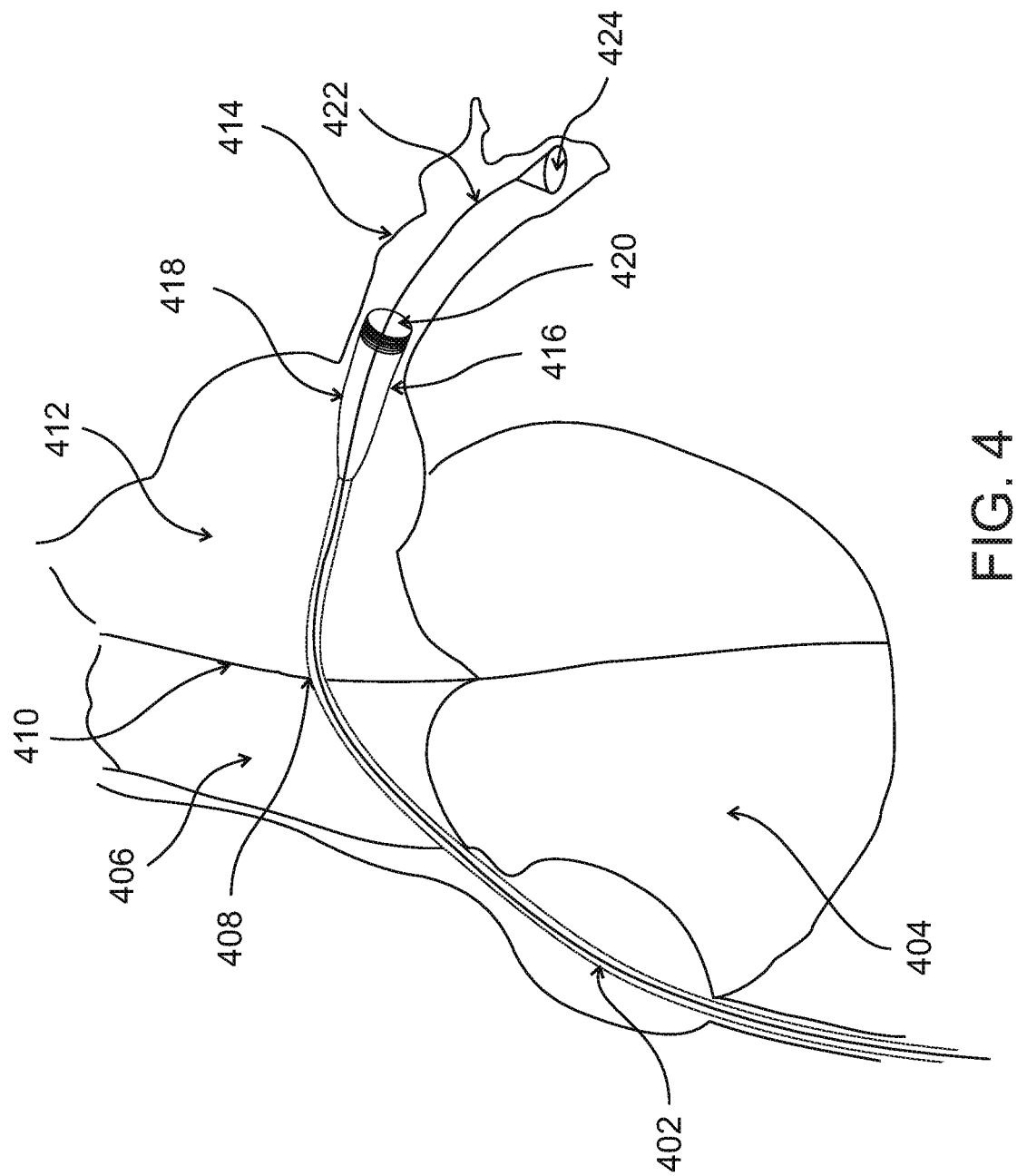
FIG. 4 is a schematic illustration of a device for covering at least part of the LAA inside the heart, according to some embodiments of the invention.

Reference is now made to FIG. 4, describing the insertion of a catheter into the LA, according to some embodiments of the invention.

According to some exemplary embodiments, catheter 402 is navigated through the right room 404 of the heart and into the right atrium 406. In some embodiments, the catheter 402 is then inserted through an opening 408 in the septum 410 between the atria, into the LA 412.

According to some exemplary embodiments, a cover 418 is deployed from the lumen of the catheter, through the LAA opening 416 and is inserted into the LAA 414. In some embodiments, the cover is inserted at least 10 mm, for example 10, 20, 30 mm or any intermediate or larger distance into the LAA.

Reference is now made to FIGS. 5A-5B, describing the positioning of a cover inside the LAA, according to some embodiments of the invention.

According to some exemplary embodiments, a catheter 502 is positioned inside the LA 504. In some embodiments, a cover 506 is deployed from the catheter 502 and is inserted through the LAA opening 508 at least 1 mm, for example 1, 5, 10 mm into the LAA 510. In some embodiments, a closing element 512 of the cover 506 adjusts the diameter of the distal opening 514 of the cover 506, for example to allow the insertion of the cover into the LAA 510. Optionally the closing element 512 comprises at least two rings, for example the rings 375, 377 and 379 shown in FIGS. 3H and 3I In some embodiments, the closing element 512 reduces the diameter of the distal opening 514 to allow its insertion into the LAA 510. Optionally, when the cover 506 is in a desired location within the LAA 510, the closing element expands and applies force against the inner surface of the LAA 510 wall. In some embodiments, application of force on the inner surface of the LAA 510 allows for example, to form a sealed fluid flow from the LAA into the cover, and therefore to isolate the LAA from the LA. In some embodiments, isolation of the LAA from the LA prevents the release of blood clots and/or tissue debris into the LA and the blood stream as described herein.

According to some exemplary embodiments, once the LAA is isolated from the LA, a flexible inverting element 516, for example a vacuum catheter is pushed or pulled through the cover 506 into the LAA 510. In some embodiments, an inverting head 518 of the inverting element 516 is advanced into the LAA 510 until it contacts the LAA wall. Optionally, the inverting head 518 is advanced or steered into a protrusion 520 of the LAA 518, where it contacts the LAA wall. According to some exemplary embodiments, a grasping member comprising a plurality of teeth is advanced through the inverting head 518 into the LAA, for example to grasp a portion of the LAA wall. In some embodiments, retraction of the grasping member positions the grasped LAA wall portion within the inverting head. In some embodiments, negative pressure, for example vacuum forces are applied through the inverting head 518 on the LAA wall portion.

Figure 5C:
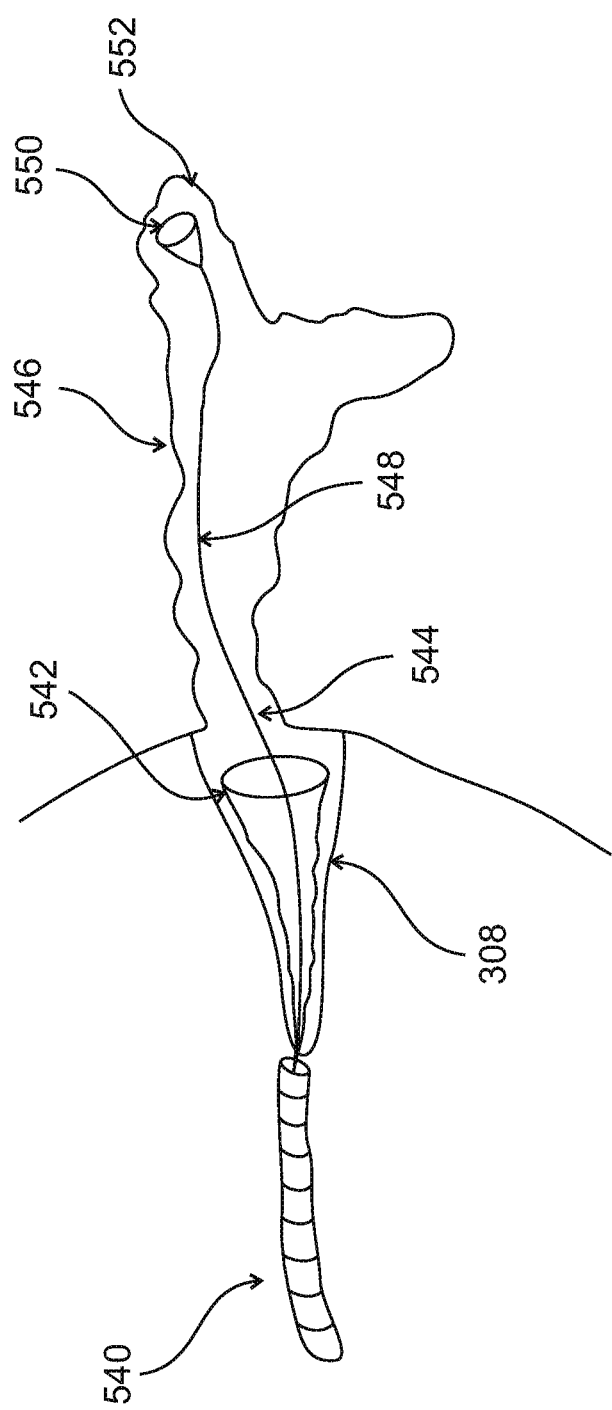
FIGS. 5C and 5D are schematic illustrations of a cover positioned outside of the LAA, according to some embodiments of the invention.
Figure 5D:
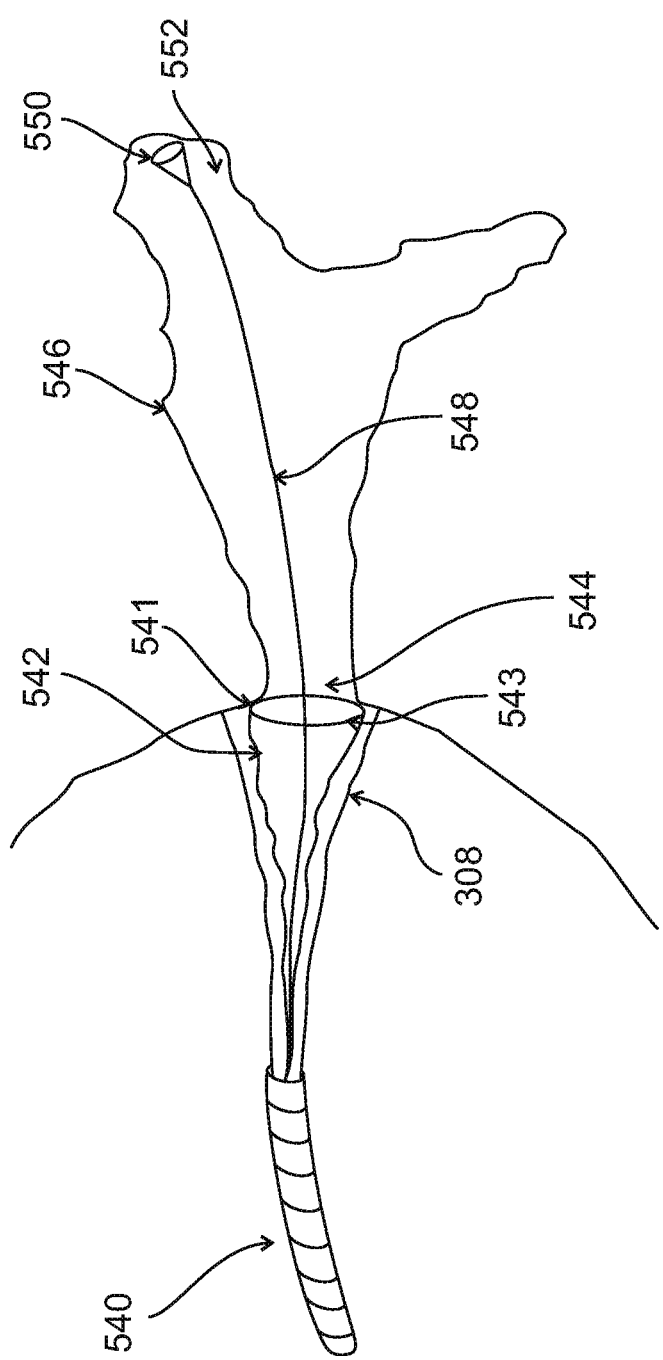

Reference is now made to FIGS. 5C and 5D describing the positioning of the cover outside of the LAA, according to some embodiments of the invention.

According to some exemplary embodiments, a catheter 540 is introduced into the LA and deploys a sealing cap, for example sealing cap 308 around the LAA opening 544. In some embodiments, the cap is pushed or pulled against the LA wall with a sufficient force, for example to allow isolation of the LAA from the LA. Alternatively or additionally, the cap is anchored to the LA wall by a plurality of anchors. In some embodiments, the cap comprises a ring with a plurality of opening that allows, for example to attach the cap by application of vacuum through the openings.

According to some exemplary embodiments, only after the LAA is isolated from the LA, a cover 542 is deployed from the catheter 540 and is placed in direct contact with the LAA opening or in a distance from the LAA opening 544. In some embodiments, a rim 543 surrounding the distal opening of the mesh is in a direct contact with the LA wall 541 surrounding the LAA opening 544.

In some embodiments, an inverting element 548, for example a vacuum catheter is inserted into the LAA 546. In some embodiments, the inverting head 550 of the inverting element 548 is advanced into the LAA 546 until it contacts the LAA wall. Optionally, the inverting head 550 is advanced and/or steered into a protrusion 552 of the LAA 546, where it contacts the LAA wall.

Reference is now made to FIGS. 6A-6D describing the covering of an inverted LAA section, according to some embodiments of the invention.

According to some exemplary embodiments, the inverting head 518 contacts the LAA wall with sufficient force that allows for example, to pull the LA wall into the cover 506. In some embodiments, the inverting head 518 pulls the LA wall and at least partly inverts the LA. In some embodiments, the inverted section of the LAA remains in the LAA lumen. Alternatively, the inverted section of the LAA is at least partly positioned within the LA.

According to some exemplary embodiments, when the LAA is inverted in a desired degree or is positioned in a desired distance from the closing element 512, the closing element 512, for example a ring or a lasso closes the distal opening 514 of the cover 506. In some embodiments, the ring comprises a plurality of anchors, for example pins, or hooks that penetrate into the LA wall when the ring is tightly attached to the LAA. In some embodiments, the lasso is closed with a force of up to 10 KG, for example 1, 2, 3, 4 KG or any intermediate, larger or smaller value.

In some embodiments, the LAA is inverted to a desired distance based on x-ray visualization and/or ultrasound imaging technique. In some embodiments, the inversion distance of the LAA is controlled, optionally by a user, to verify that there is no damage or an undesired effect to the Mitral Valve.

According to some exemplary embodiments, for example as shown in FIG. 6C, the LAA 511 is fully inverted through distal opening 519 of the cover 506 into the LA. Alternatively, for example as shown in FIG. 6D, the LAA 511 is partly inverted through the distal opening 519 of the cover 506 into the LA, while leaving some sections of the LAA, for example sections 515 and 519 outside of the cover 506.

Figure 6E:
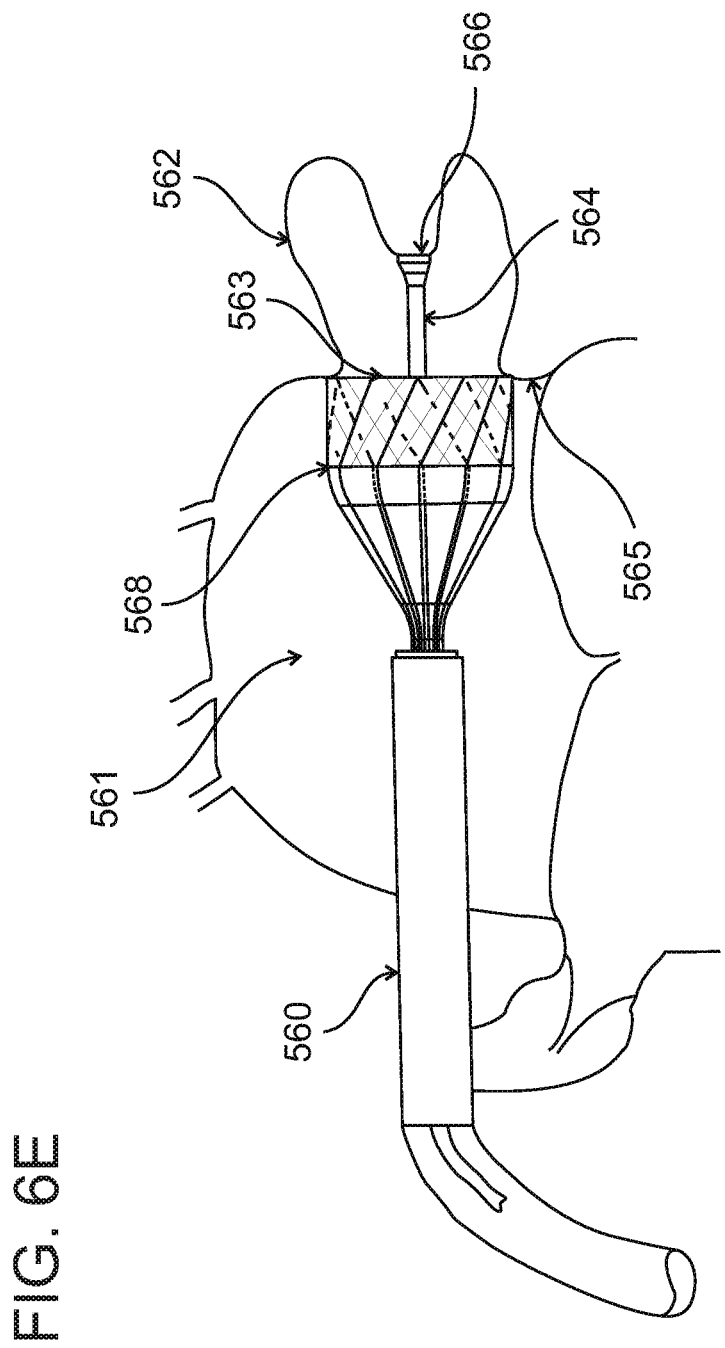
FIG. 6E is a schematic illustration of a mesh in an open conformation wrapped around an inverted LAA, according to some embodiments of the invention.

Reference is now made to FIGS. 6E-6G describing the covering of an inverted LAA by a mesh, according to some embodiments of the invention.

According to some exemplary embodiments, for example as shown in FIG. 6E, a catheter 560 is inserted into the LA 561 and deploys a cover, for example mesh 568. In some embodiments, the mesh 568 comprises a metal web, optionally a tubular metal web. In some embodiments, the tubular metal web comprises a plurality of openings larger enough to allow blood flow and smaller enough to prevents passage of cell and tissue debris. In some embodiments the openings have a maximal dimension of up to 200 microns, for example 10 microns, 50 microns, 100 microns, 150 microns or any intermediate, smaller or larger value. Optionally, the mesh comprises a woven tube, for example a woven polyester tube associated at least partly with the metal web. In some embodiments, the mesh 564 is deployed by retracting the catheter cover surrounding the mesh 568. In some embodiments, when the catheter cover is retracted, the mesh which is optionally made from a shape memory alloy, for example Nitinol expands to a relaxed conformation. In some embodiments, when the mesh 568 is in a relaxed conformation, the diameter of the distal opening of the mesh 568 is larger than the diameter of the LAA opening. In some embodiments, the mesh 568 expands at least partly within the LAA and/or at least partly within the LAA opening.

According to some exemplary embodiments, a rim 563 surrounding and/or associated with the distal opening of the mesh is positioned in a direct contact with the LA wall 565, for example to isolate the LAA from the LA. Alternatively, the rim 563, optionally comprising one or more rings expands at least partly within the LAA opening. In some embodiments, expansion of the rim 563 within the LAA opening applies force on the internal surface of the LAA opening. In some embodiments, the force applied by the rim is sufficient to prevent leakage of blood between the rim and the LAA opening. In some embodiments, the force applied by the rim 563 on the internal surface is a radial force of up to 20 Newton (N), for example 1N, 2N, 5N, 10N or any intermediate, smaller or larger value.

According to some exemplary embodiments, an inverting element, for example vacuum catheter 564 is inserted into the LAA. In some embodiments, a vacuum head 566 of the vacuum catheter 564 applies vacuum on the internal surface of the LAA wall. In some embodiments, the vacuum head is then retracted towards the LA and inverts at least partly the LAA 562.

According to some exemplary embodiments, for example as shown in FIG. 6F, when at least part of the inverted LAA is positioned inside the mesh 568, a ring 570 surrounding the mesh 568 is advanced towards the LA wall 565, and optionally placed in direct contact with the LA wall 565. Alternatively, the ring 570 is advanced until it reaches the distal end of the mesh.

According to some exemplary embodiments, the ring 570 is a flexible ring having an adjustable diameter. In some embodiments, the flexible ring is contracted when the ring is in contact with the LA wall 565. In some embodiments, when the ring contracts, it causes the mesh 568 to contract to a closed conformation. Optionally, when the mesh 568 is contracted to a closed conformation, the mesh closes inverted LAA positioned inside it.

According to some exemplary embodiments, the ring 570 has a fixed diameter which is smaller than the diameter of the mesh 568 in an open conformation. In some embodiments, when the ring 570 is advanced towards the LA wall 565, it contracts the mesh 568 around the inverted LAA. In some embodiments, the mesh 568 is designed and shaped to irreversibly contract and cannot acquire an open conformation once contracted. In some embodiments, when the mesh 568 irreversibly contracts, the ring 570 is optionally retracted out from the body. Alternatively, when the mesh 568 is shaped and sized to reversibly contract, the ring 570 is fixed on the mesh 568 and optionally next to the LA wall, for example to prevent the re-opening of the mesh 568.

According to some exemplary embodiments, for example as shown in FIG. 6G when the ring 570 is fixed and/or the mesh 568 is fastened around the inverted LAA, catheter 560 is retracted from the heart.

Exemplary Cover Closing Mechanisms

Figure 6H:
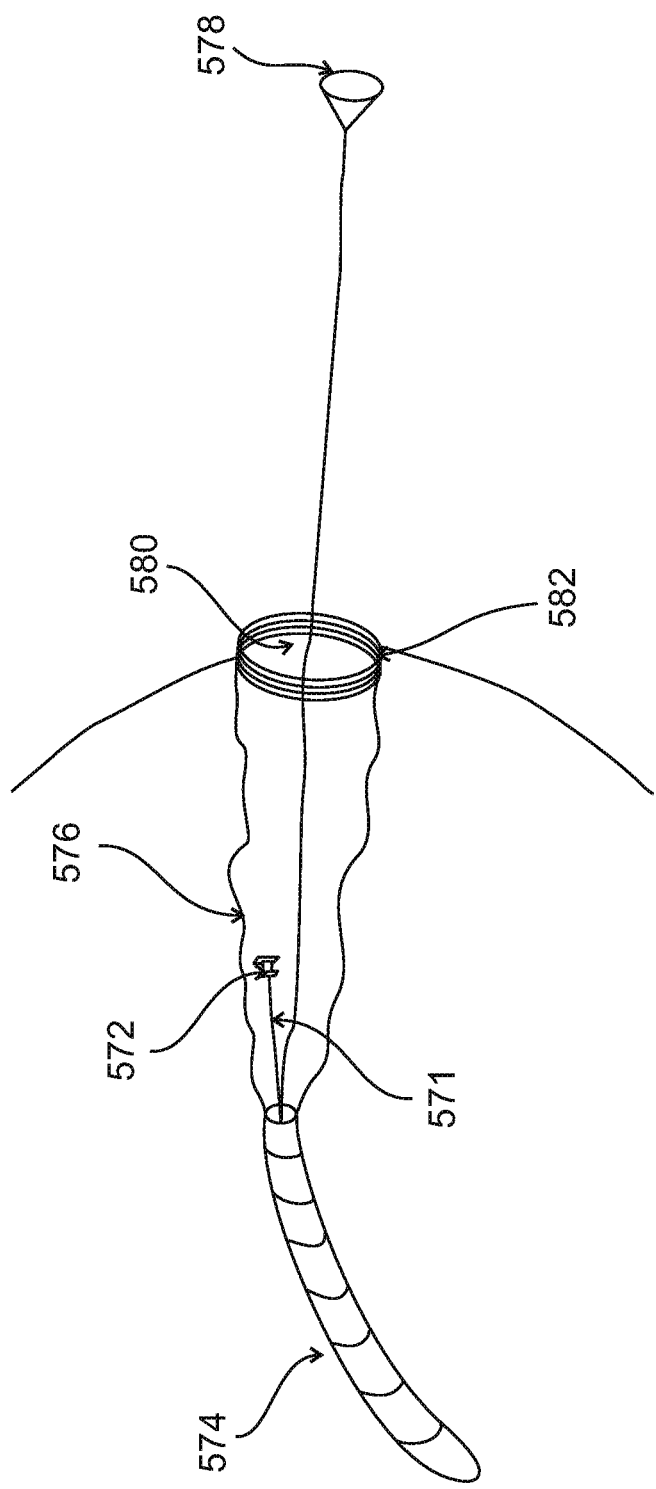

Reference is now made to FIGS. 6H-6K, describing closing mechanisms of the cover, according to some embodiments of the invention. According to some exemplary embodiments, for example as shown in FIG. 6H, catheter 574 deploys a cover, for example a mesh 576 near the LAA opening. In some embodiments, the distal opening 580 of the mesh 576 is in a direct contact with the LA wall, and surrounds the LAA opening. In some embodiments, an inverting element, for example vacuum head 578 extends through the distal opening 580, optionally into the LAA. In some embodiments, catheter 574 comprises a closing mechanism of the proximal opening of the mesh 576. In some embodiments, the closing mechanism comprises a clip 572, optionally connected to catheter 574 by wire 571. Optionally, the closing mechanism comprises a flexible ring with an adjustable diameter.

According to some exemplary embodiments, for example as shown in FIG. 6I, when the mesh 576 is fastened around an inverted LAA 562, for example by closing the distal opening 580 using a ring 582 or a lasso, the vacuum head is retraced out from the mesh 576. In some embodiments, the clip 572 is retraced into or around the proximal opening of the mesh 576, for example to close the proximal opening.

Figure 6J:
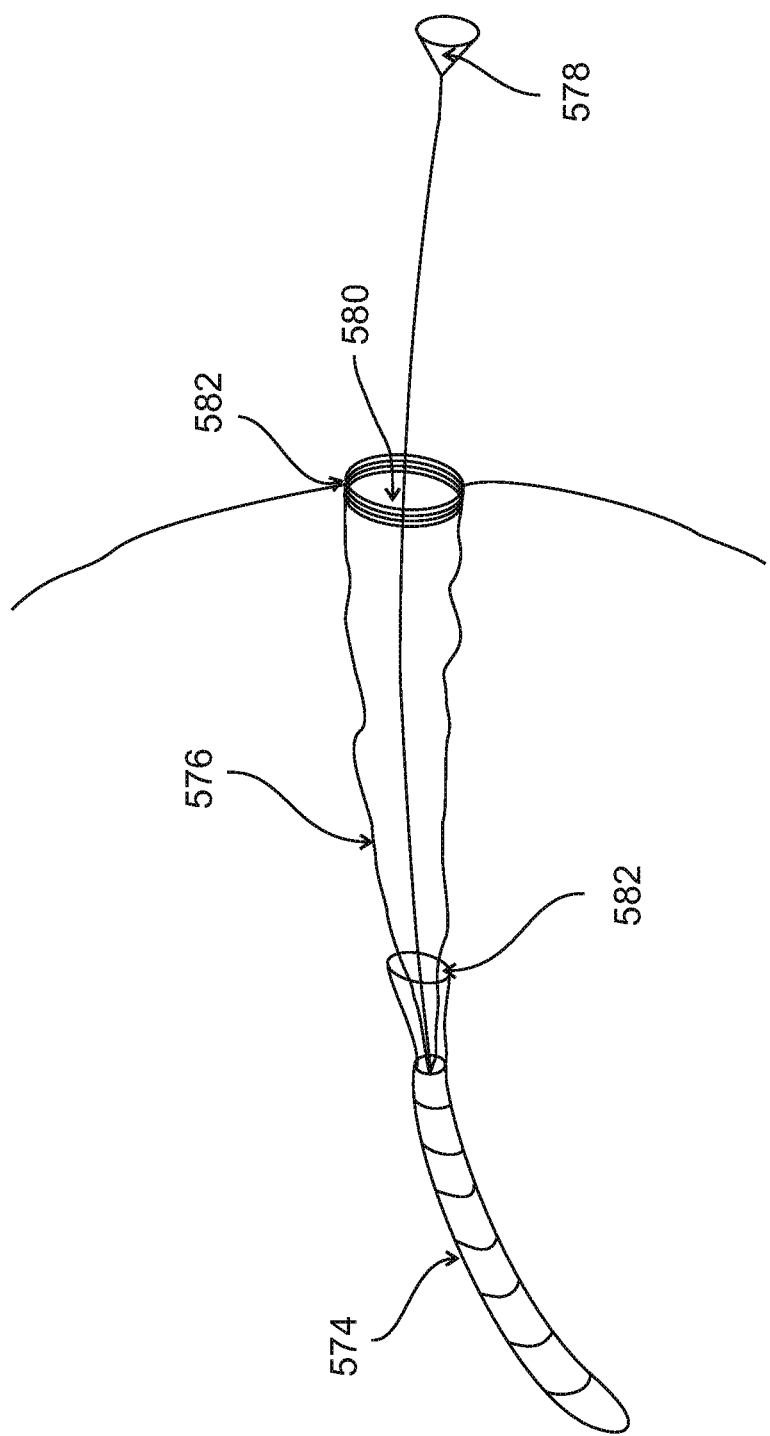

According to some exemplary embodiments, for example as shown in FIG. 6J, the catheter 574 comprises a loop, for example a lasso 582 around the proximal opening of the mesh 576. In some embodiments, for example as shown in FIG. 6K, when the vacuum head 578 is retracted through the proximal opening of the mesh 576, the lasso 582 is fastened around the mesh 576 and closes the proximal opening. In some embodiments, when the proximal opening is closed, the catheter 574 is retracted out from the heart. Optionally, at least one ring is positioned around the catheter, and is advanced to be placed around the proximal opening and to close the opening when it contracts.

Exemplary Reshaping the LAA Tissue

Reference is now made to FIGS. 6L-6M and 7A-7C describing the reshaping of the LAA tissue following the covering procedure, according to some embodiments of the invention.

Figure 6L:
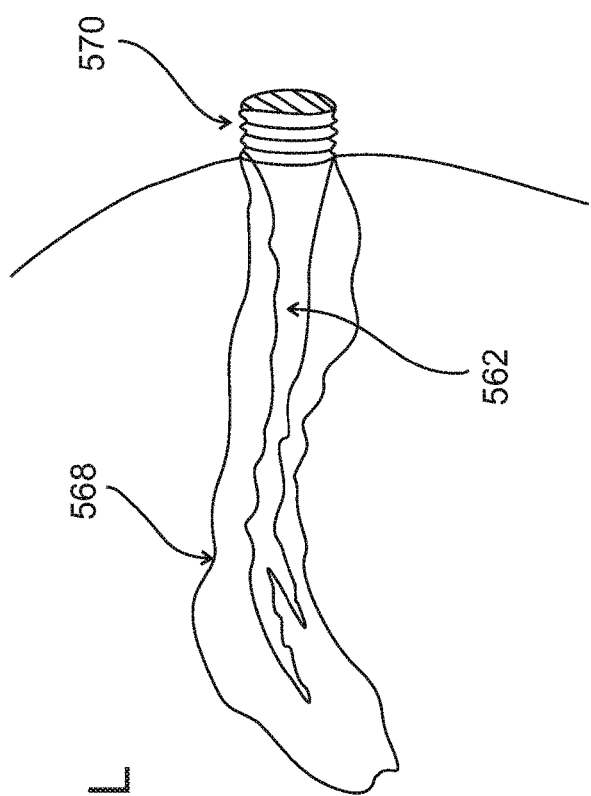
FIG. 6L is a schematic illustration of a cover positioned partly within the LAA, and wrapped around an inverted section of the LAA, according to some embodiments of the invention.
Figure 6M:
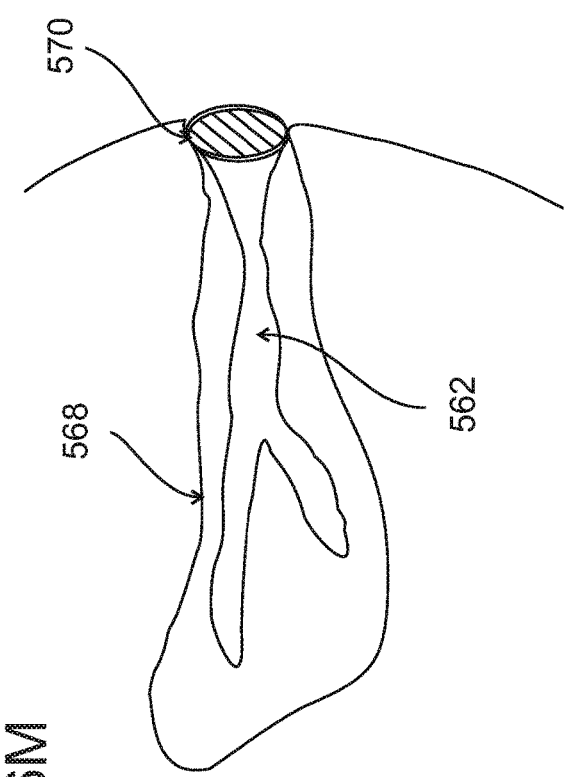
FIG. 6M is a schematic illustration of a cover positioned inside of the LA and wrapped around an inverted section of the LAA, according to some embodiments of the invention.

According to some exemplary embodiments, an inverted section of the LAA 562 is wrapped with a cover, for example mesh 568. In some embodiments, for example as shown in FIG. 6L, the mesh 568 is positioned partially inside the LAA. In some embodiments, the distal opening 570 of the mesh 568 is fastened inside the LAA. In some embodiments, for example as shown in FIG. 6M, the mesh 568 remains inside the LA, and the distal opening 570 of the mesh 568 is fastened inside the LA.

Figures 7A, 7B:
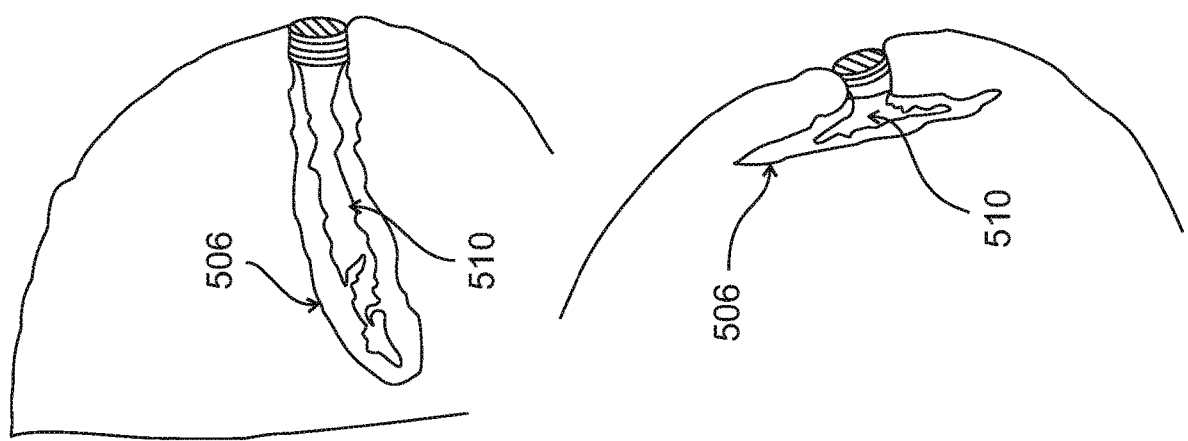
FIGS. 7A-7C are schematic illustrations of a reshaped LAA, placed in a cover, according to some embodiments of the invention.
Figure 7C:
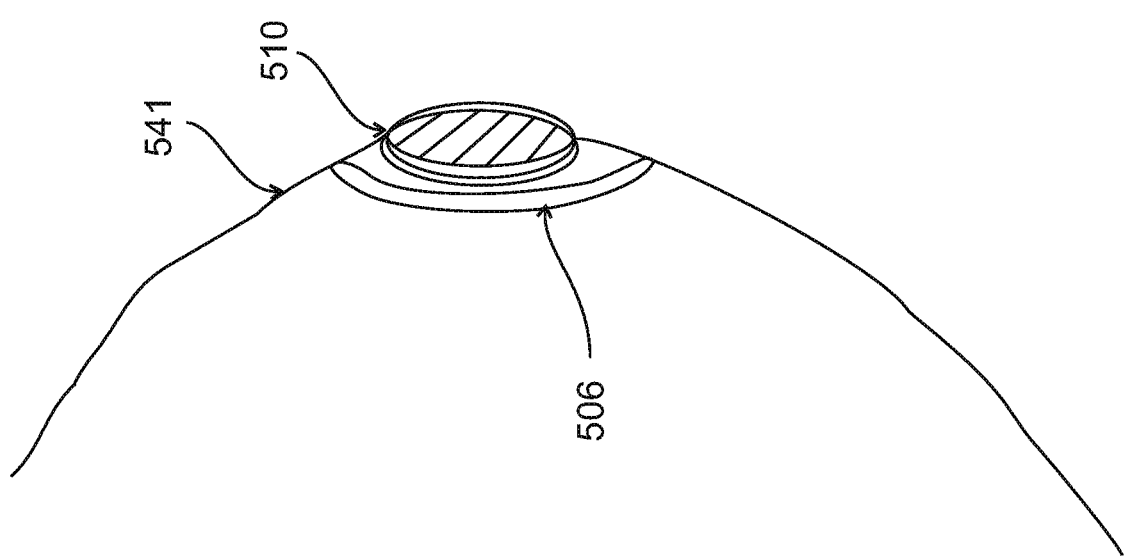

According to some exemplary embodiments, for example as shown in FIGS. 7A-7C following a covering procedure, the covered LAA tissue 510 optionally undergoes different fibrotic procedures. In some embodiments, if the cover 506 is a mesh, then the LAA tissue is constantly washed with blood from the LA, but LAA tissue debris cannot pass the mesh into the LA. In some embodiments, the cover is made from or coated with biocompatible materials that speed up the fibrotic process, for example to shrink the LAA tissue faster.

According to some exemplary embodiments, the LAA tissue shrinks due to different biological processes. In some embodiments, the mesh functions as a LAA tissue collector. In some embodiments, the cover is pre-shaped as a disc and is made from a memory-shape alloy material, for example Nitinol. In some embodiments, as the LAA shrinks the pre-shaped cover return to its disc shape and pushes the LAA tissue against the LA wall.

According to some exemplary embodiments, for example as shown in FIG. 7C, the cover 506 pushes the inverted LAA 510 closer to the LA wall 541, until optionally the until the LAA 510 shrinks completely, and the cover 506 fully contacts the LA wall 541.

Exemplary LAA Closure by a Lasso

According to some exemplary embodiments, a lasso is positioned around at least one inverted section of LAA. In some embodiments, the lasso is then tightened to close the inverted section.

Reference is now made to FIGS. 8A-8B describing the closure of LAA inverted sections using a lasso, according to some embodiments of the invention.

According to some exemplary embodiments, a catheter 802 is inserted into the LA. In some embodiments, a cover 804, for example a mesh is deployed from the catheter and is positioned over the LAA opening 806. In some embodiments, the distal opening 806 of the cover 804 surrounds the LAA opening 807. In some embodiments, the cover 804 comprises a flexible ring 805 positioned around the distal opening 806. In some embodiments, the ring 805 is pushed or pulled against the LA wall, for example to isolate the LAA 808 from the LA by the cover 804. Optionally, the ring comprises a plurality of anchors that anchor the ring to the LA wall.

According to some exemplary embodiments, once the LAA 808 is isolated, at least one inverting element, for example vacuum heads 811 and 810 are inserted into the LAA 808 and contact the LAA wall, for example as shown in FIG. 5A. In some embodiments, vacuum is applied and the vacuum heads 811 and 810 are retracted towards the LA while pulling the LAA wall. Optionally, at least one grasping member is advanced from some of the vacuum heads into the LAA, for example to grasp a portion of the LAA wall. In some embodiments, the grasping member is retracted into the lumen of the vacuum head while placing the portion of the LAA within the vacuum head. In some embodiments, for example as shown in FIGS. 8A and 8B, two sections of the LAA 808 are inverted and remain inside the LAA 808. In some embodiments, each of the vacuum heads 811 and 810 is surrounded by a lasso. In some embodiments, each of the vacuum heads pulls an inverted section of the LAA into the lasso, for example when the lasso is pre-mounted on the cover. Alternatively, the lasso is advanced to be positioned around the inverted sections of the LAA.

According to some exemplary embodiments, for example as shown in FIG. 8B, the lasso, for example lasso 812 and lasso 813 are fastened around the inverted LAA sections. In some embodiments, after the lasso are tightened around the LAA, the wire connected to the lasso is detached from the lasso and is removed from the heart, for example as described in FIGS. 3F and 3G.

According to some embodiments, the lasso is made from a wire having a diameter in the range of 0.2-2 millimeters, for example 0.5-1.2 millimeters, 0.2-1 millimeters or any other range of diameters. In some embodiments, the lasso wire is detectable by imaging techniques, for example X-ray radiation.

Exemplary Attachment of an Inverted LAA Section to the LA Wall

According to some exemplary embodiments, a catheter is inserted into the LA. In some embodiments, an isolating cover is deployed over the LAA opening, for example to isolate the LAA from the LA. In some embodiments, the isolating cover forms an isolated working room, for example to allow safe manipulation of the LAA. In some embodiments, the isolating cover is anchored to the LA tissue surrounding the LAA opening. In some embodiments, at least one inverting element is inserted into the LAA and inverts a section of the LAA at least partially into the LA.

According to some exemplary embodiments, the inverted section is fastened by a lasso, a ring, a clip or any fastening means capable of fastening the LA wall. In some embodiments, the isolating cap or the cover, for example as shown in FIG. 7C is then pushed or pulled against the LA wall and optionally attaching the inverted section of the LAA to the inner surface of the LA wall. Optionally, the isolating cap comprises a plurality of anchors positioned between the outer circumference of the cap and the cap center, for example to anchor the cap to the inner surface of the LA wall.

According to some exemplary embodiments, once the inverted LAA is covered, it undergoes different biological processes that cause the LAA to shrink after few months. In some embodiments, when the LAA shrinks it is being covered with endocarp cells.

Exemplary Disc-Shaped Cover

Reference is now made to FIGS. 8C and 8D, describing a disc-shaped cover, according to some embodiments of the invention. According to some exemplary embodiments, the cover comprises a disc 852. In some embodiments, the LAA is inverted into the disc 852 and is fastened by a ring 854 positioned between the disc 852 and the LA wall 853. Optionally, ring 854 is fastened around the inverted LAA. In some embodiments, the fastened ring prevents the release of the inverted LAA from the disc 852.

According to some embodiments, the disc 852 has a width of up to 15 mm, for example 5 mm, 10 mm, 12 mm or any intermediate, smaller or larger value. In some embodiments, the disc 852 is shaped and sized to cover the LAA opening. In some embodiments, the disc 852 has a diameter of at least 1 cm, for example 1 cm, 2 cm, 3 cm or any intermediate, smaller or larger value.

According to some exemplary embodiments, the disc 852 adjusts to the size and volume of the inverted LAA. In some embodiments, the disc 852 is made from a shape memory alloy, for example Nitinol. In some embodiments, for example as shown in FIG. 8D, the disc 852 acquires a flattened shape as the inverted LAA shrinks.

Exemplary Devices Placed Inside Isolator

According to some exemplary embodiments, when placing a device, for example a plug into the LAA, there is a risk that blood clots or debris found inside the LAA will be release into the LA and into the blood stream. These blood clots may travel to the brain and cause thrombotic stroke. In some embodiments, in order to avoid any release of blood clots or debris from the LAA, the LAA is first isolated from the LA by placing a cover over the LAA opening, or inside the LAA. In some embodiments the plug is positioned inside the LAA and is isolated from the LA by the cover.

Reference is now made to FIG. 9A describing the positioning of a device that comprises a plug or a plate positioned inside the LAA and a plate placed inside the LA, for example an AMPLATZER™ device. According to some exemplary embodiments, an isolator, for example cover 914 is positioned inside the LA 900 and over the LAA opening 908 to isolate the LAA 902 from the LA 900. Alternatively, the cover is inserted into the LAA opening. In some embodiments, at least one inverting device is inserted into the LAA 902 and inverts at least one section of the LAA 902. In some embodiments, this section is then fastened by a lasso, for example lasso 903 and lasso 904. Alternatively, the inverted section is fastened by a ring, a clip or optionally by any fastening means capable of fastening the LAA. In some embodiments, a plug device 906, for example an AMPLATZER™ device is positioned inside the LAA 902 and is optionally anchored by wires to at least one of the fastened lasso, for example lasso 903 or lasso 904 by wires 904 interconnecting the lasso and the plug device 906.

Figure 9B:
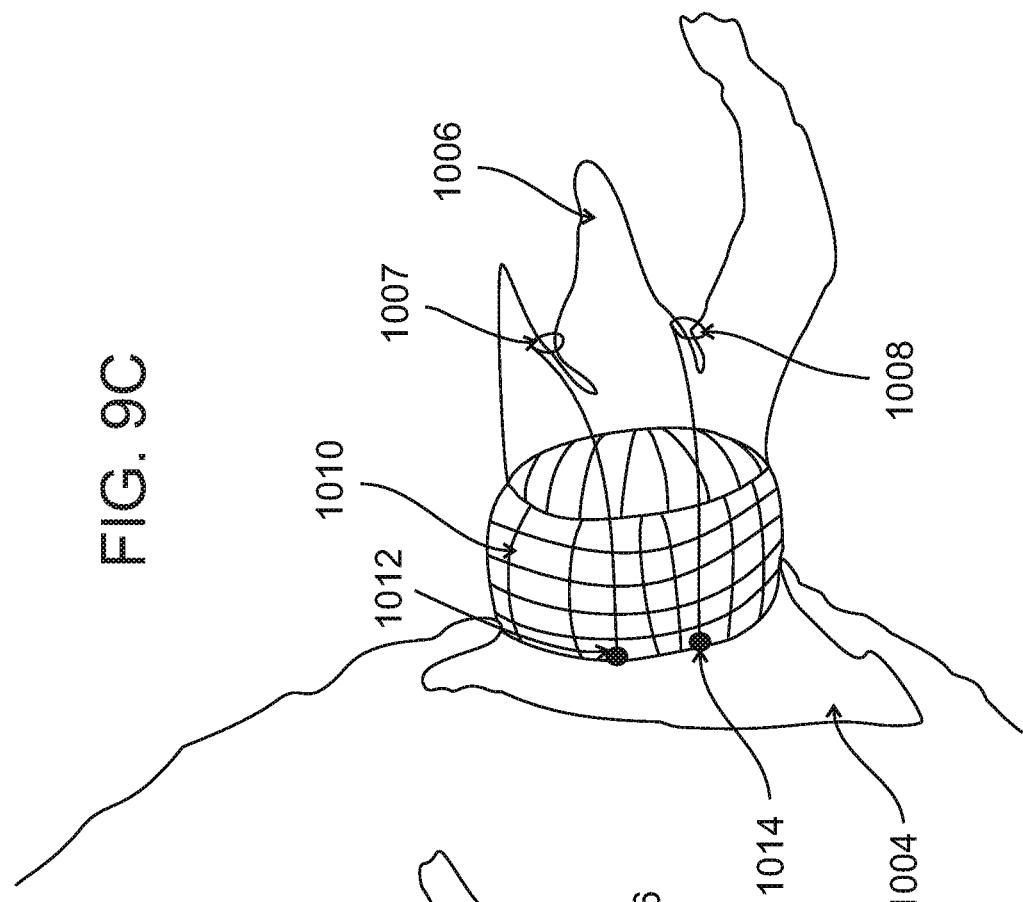
Figure 9C:
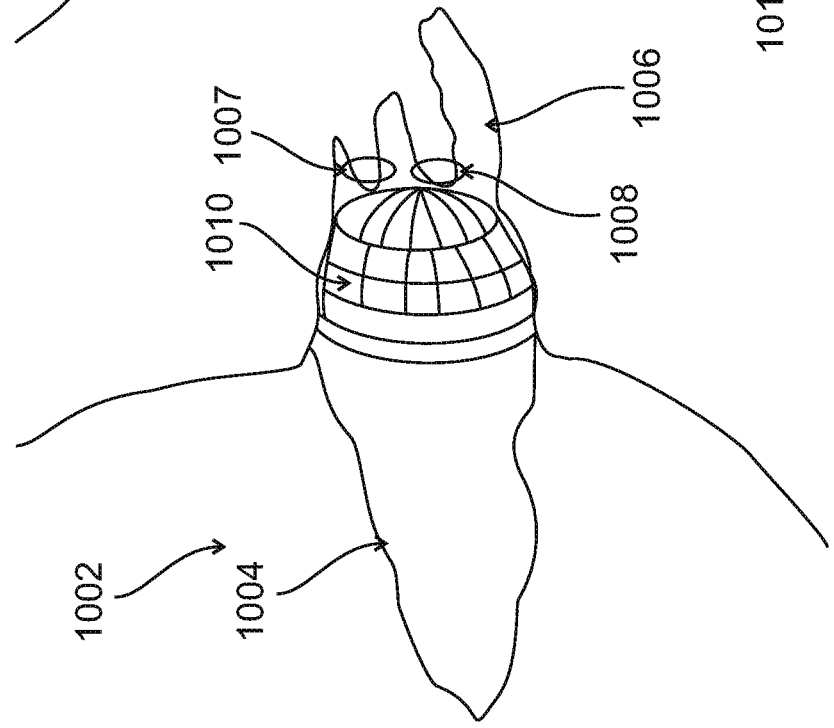

Reference is now made to FIGS. 9B and 9C describing the positioning of a device inside the LAA, that is anchored against the LAA walls, for example a WATCHMAN™ device.

According to some exemplary embodiments, an isolator, for example cover 1004, is placed over the LAA opening or inserted into the LAA 1006, to isolate the LAA from the LA. In some embodiments, at least one section of the LAA 1006 is inverted and fastened by a lasso, for example lasso 1007 and lasso 1008. Alternatively, the inverted section of the LAA 1006 is fastened by a ring or by a clip. Optionally, the inverted section of the LAA is fastened by any fastening means capable of fastening the LAA.

According to some exemplary embodiments, a plug device 1010 is then positioned inside the LAA and is optionally anchored to the fastening means, for example a lasso, a ring or a clip by wires. Alternatively, the wires interconnect the cover 1004 and the fastening means connected to the LAA. Optionally, the wires are tightened, for example to hold the plug device between the cover 1004 and the inverted sections of the LAA.

As described above, a possible advantage of using a plug device in combination with the device and method described herein, is that they allow to minimize the risk of blood clot release from the LAA during the positioning of the devices. An additional advantage is that the devices can be anchored within the LAA to partially inverted sections of the LAA using wires fastened around the inverted sections, instead of using pins that penetrate into the LA wall. In some embodiments, placing an isolator to isolate the LAA and then closing an inverted section of the LAA as described herein is an alternative approach to anchoring plugs inside the LAA.

Exemplary Cleaning the LAA

Figure 10:
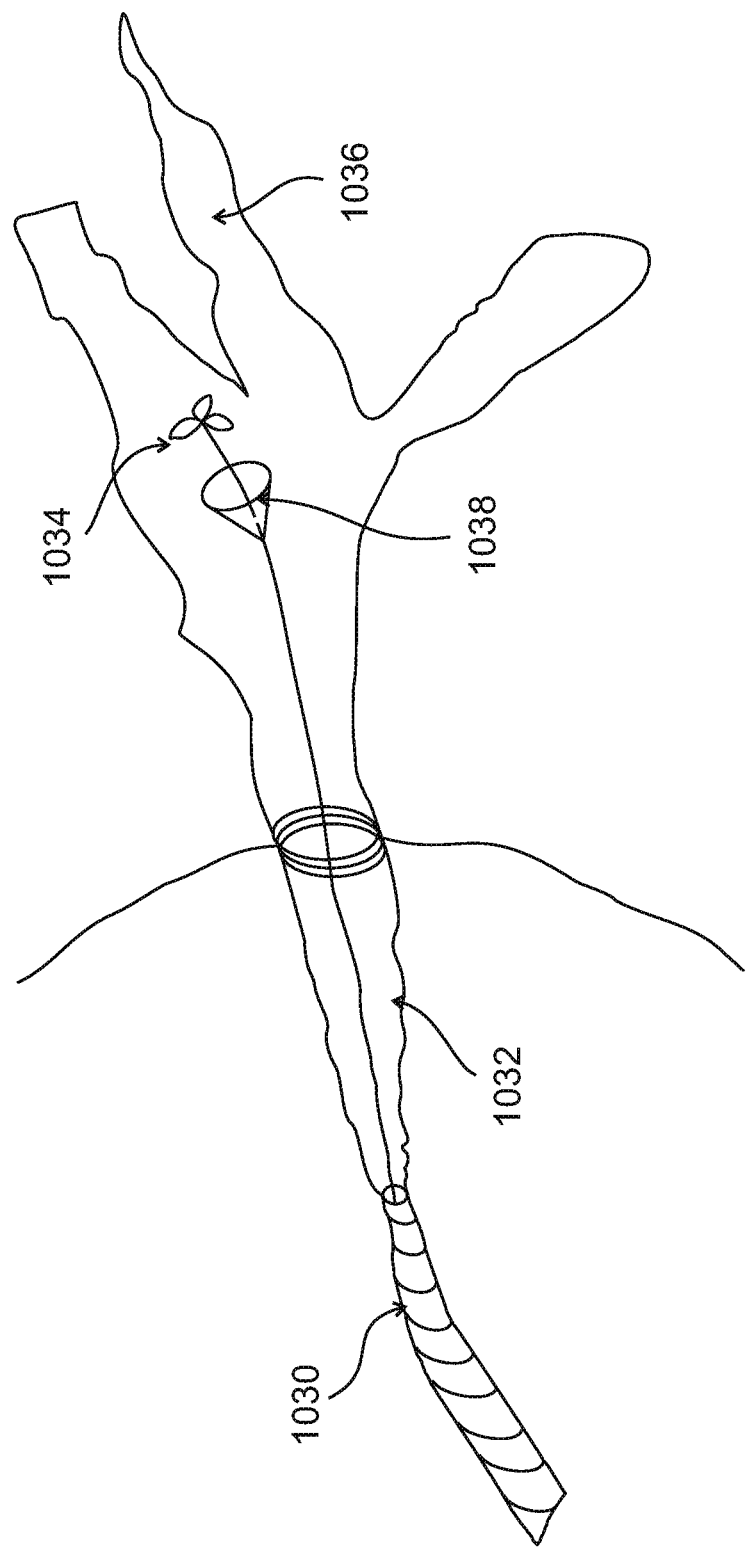
FIG. 10 is a schematic illustration of a cleaning brush inside the LAA, according to some embodiments of the invention.

Reference is now made to FIG. 10 describing a catheter device with a cleaning brush, according to some embodiments of the invention.

According to some exemplary embodiments, a cover, for example a mesh 1032 is deployed from catheter 1030. In some embodiments, the mesh 1032 is inserted into the LAA 1036 or positioned over the LAA opening, for example to isolate the LAA 1036 from the LA prior to a cleaning process of the LAA. In some embodiments, once the LAA 1036 is isolated from the LA, a cleaning element, for example a cleaning brush 1034 and/or a vacuum head 1038 is inserted into the LAA 1036. In some embodiments, the cleaning element removes blood clots and tissue debris found inside the LAA 1036. In some embodiments, the vacuum head applies vacuum and removes the blood clots and debris outside from the body. In some embodiments, the cleaning brush 1034, release blood clots from within the LAA 1036. In some embodiments, the blood clots are then trapped by the mesh 1032. Alternatively, they are directed by the mesh 1032 through the lumen of catheter 1030 outside from the heart.

Exemplary Deployment of an Isolator

Reference is now made to FIGS. 11A-11E, describing the deployment of a mesh isolator, for example a cover, according to some embodiments of the invention.

According to some exemplary embodiments, catheter 1102 comprising an isolator cover, for example a mesh 1104 and a ring 1106. In some embodiments, the mesh 1104 comprises a metal web, optionally a tubular metal web. In some embodiments, the tubular metal web comprises a plurality of openings larger enough to allow blood flow and smaller enough to prevents passage of cell and tissue debris. In some embodiments, the mesh openings have a maximal dimension of up to 200 microns, for example 10 microns, 50 microns, 100 microns, 150 microns or any intermediate, smaller or larger value. Optionally, the mesh comprises a woven tube, for example a woven polyester tube associated at least partly with the metal web.

Figure 11A:
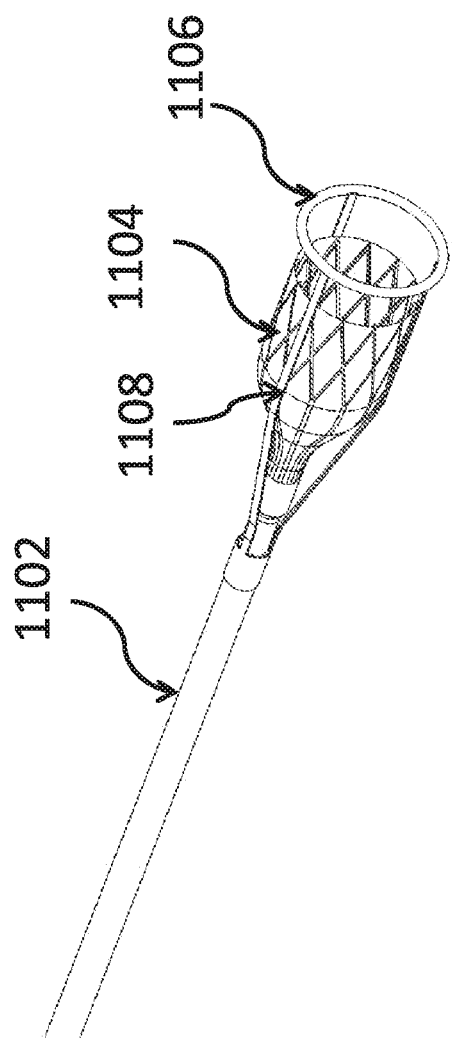
Figure 11B:
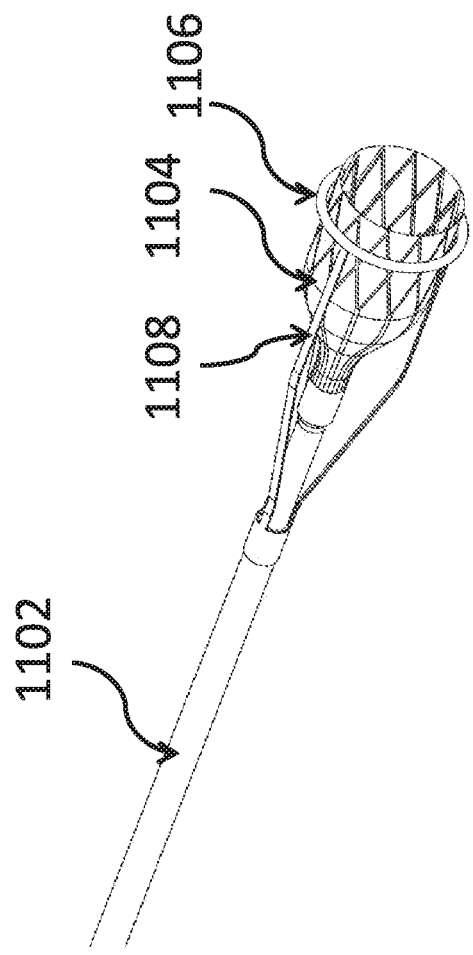

According to some exemplary embodiments, when the catheter is deployed in the LA, the ring 1106 is positioned distally to the mesh 1104. In some embodiments, for example when the ring is placed in contact with the LA wall, the mesh 1106 is advanced beyond the ring 1106, for example as shown in FIG. 11B. In some embodiments, when the mesh is pushed forward, for example into the LAA. Alternatively, the ring 1106 and the mesh are inserted into the LAA. In some embodiments, for example as shown in FIG. 11C when the ring 1106 is fully retracted, the mesh 1104 opens, optionally to an expanded conformation. In some embodiments, the mesh 1104 opens to an expanded conformation at least partly within the LAA. In some embodiments, when the mesh 1104 is in an expanded conformation it applies force against the inner wall of the LAA, for example to anchor the mesh 1104 at least partly within the LAA.

According to some exemplary embodiments, for example as shown in FIG. 11D, an inverting element, for example vacuum head 1110 is pushed forward through the lumen of catheter 1102 into the LAA. According to some exemplary embodiments, for example as shown in FIG. 11E, when an inverted section of the LAA is inside the mesh 1104, the mesh 1104 contracts. In some embodiments, the mesh 1104 contracts for example when a ring 1112 positioned around the distal opening of the mesh 1104 contracts.

Figure 12B:
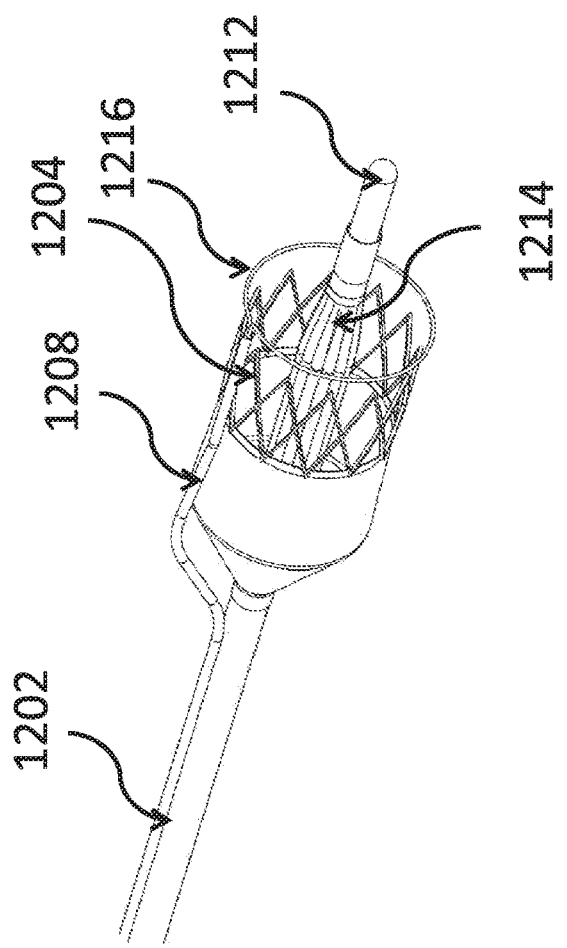
Figure 12C:
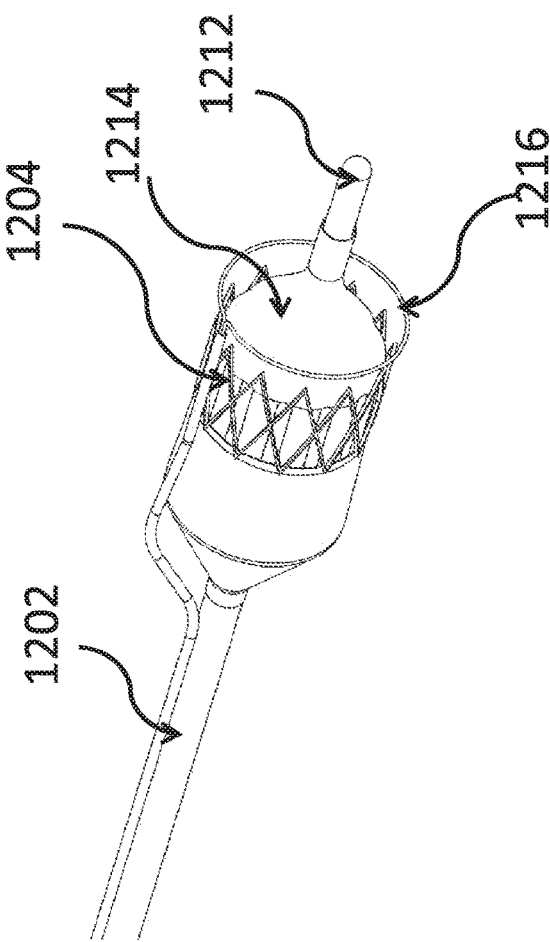
Figure 12D:
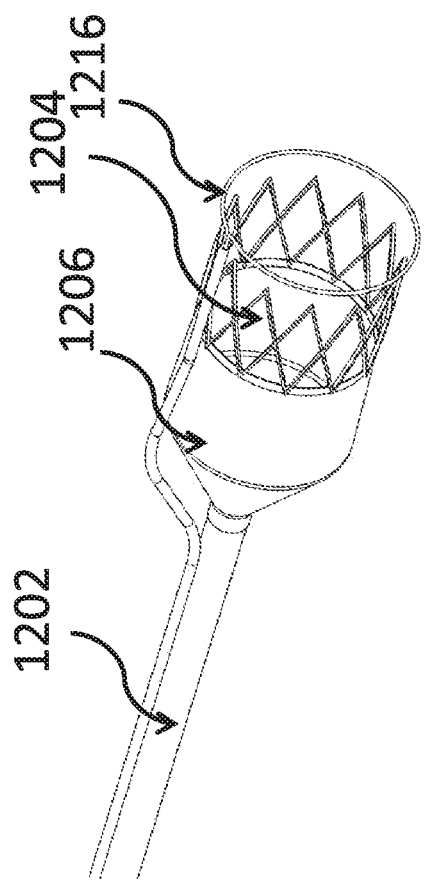
Figure 12E:
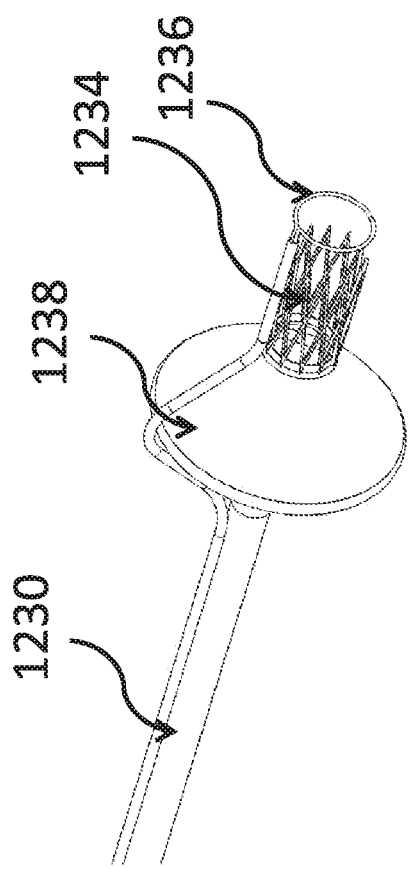

Reference is now made to FIGS. 12A-12D, describing an isolator shaped as a cup with a distal mesh, according to some embodiments of the invention. According to some exemplary embodiments, for example as shown in FIG. 12A, a catheter 1202 comprises a cup sealer 1206 with a mesh 1204, located distally to the cup sealer 1206. In some embodiments, a vacuum head 1210 is positioned inside the mesh 1210, facing the tissue. Alternatively, for example as shown in FIG. 12B, a shaft 1212 is positioned inside the mesh 1204. In some embodiments, a balloon 1214 is positioned inside the mesh 1204. In some embodiments, mesh 1204 is pushed at least partly into the LAA. In some embodiments, for example as shown in FIG. 12C the balloon 1214 is inflated, optionally to expand the mesh 1204. In some embodiments, inflating a balloon inside the mesh allows for example, to anchor the mesh inside the LAA. In some embodiments, after mesh 1204 is anchored, shaft 1212 optionally comprising an anchor, is advanced into the LAA to contact the LAA wall and to invert at least a section of the LAA.

Figure 12F:
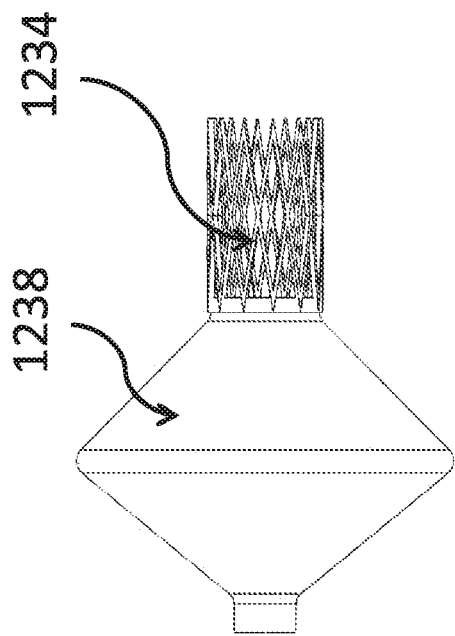
Figure 12G:
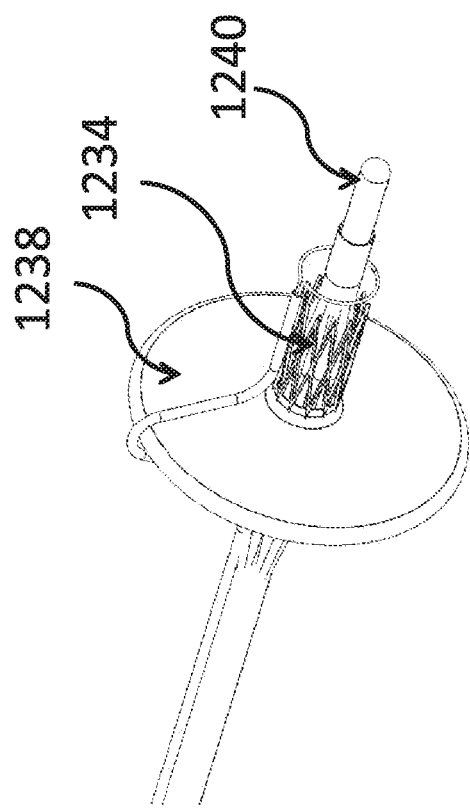

Reference is now made to FIGS. 12E-12H, describing a disc-shaped isolator with a distal mesh, according to some embodiments of the invention. According to some exemplary embodiments, a catheter 1230 comprises a disc-shaped isolator 1238 and a distal mesh 1234. In some embodiments, ring 1236 is positioned distally to the mesh 1234, and optionally faces the tissue. In some embodiments, for example as discussed in FIG. 11B, when ring 1236 is retracted, it allows, for example mesh 1234 to expand. Optionally, ring 1236 is retracted when mesh 1234 is placed inside the LAA. In some embodiments, for example as shown in FIG. 12G, a shaft 1240 is positioned inside mesh 1234. In some embodiments, shaft 1240 comprises an anchor at the distal end to allow capturing and retracting at least part of the LAA wall.

Figure 12H:
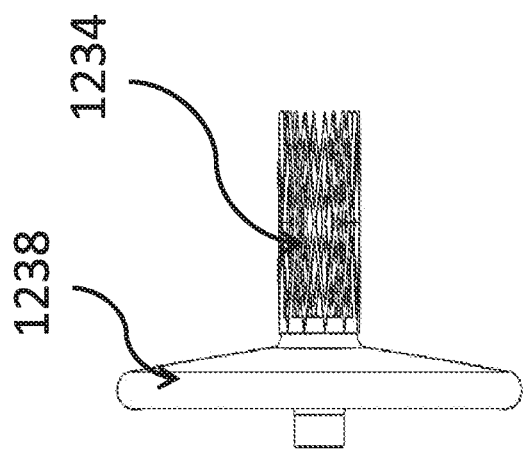

According to some exemplary embodiments, the disc-shaped isolator 1238 is capable of expanding and collapsing. In some embodiments, when the disc-shaped isolator 1238 is in an expanded conformation, for example as shown in FIG. 12F, an inverted section of the LAA is inserted into the lumen of the disc-shaped isolator 1238. In some embodiments, when the LAA tissue start to shrink, the disc-shaped isolator 1238 acquires a flattened shape, for example as shown in FIG. 12H.

Exemplary Grasping Member

According to some exemplary embodiments, in order to invert at least a portion of the LAA, at least part of the LAA wall is held and maneuvered into the LA. In some embodiments, in order to invert a portion of the LAA wall that includes one or more invaginations and optionally different shapes, a grasping member is introduced into the LAA, for example to contact and hold the LAA wall. Reference is now made to FIGS. 13A and 13B depicting a grasping member, according to some exemplary embodiments of the invention.

According to some exemplary embodiments, a grasping member 1302 comprises an elongated rod 1301 connected to a grasping head 1304 at a distal end of the rod 1301. In some embodiments, the grasping head 1304 comprises at least one movable section, for example an upper section 1308 and/or a lower section 1306. In some embodiments, at least one of the upper section 1308 and/or the lower section 1306 comprises a plurality of projections, for example teeth, shaped and sized for example to contact a tissue without piercing it. Optionally, the teeth in each section are aligned. In some embodiments, both the upper section 1308 and the lower section 1306 comprise a plurality of teeth, optionally aligned teeth. In some embodiments, the projections arrangement of the upper section 1308 is complementary to the projections arrangements of the lower section 1306. Optionally, the sections of the grasping head are connected by a hinge, for example hinge 1305.

According to some exemplary embodiments, the grasping member comprises a movable closing mechanism 1310 connected to an elongated closing rod 1311. In some embodiments, the closing mechanism 1310 is positioned at least partly around the elongated rod 1301 of the grasping member. In some embodiments, lateral movement of the closing mechanism 1310, optionally along the elongated rod 1301 moves the sections of the grasping head 1304 around the hinge 1305. In some embodiments, lateral movement of the closing mechanism, optionally around the elongated rod 1301 brings the sections of the grasping head 1304 for example sections 1308 and 1306 closer to each other. Alternatively, the lateral movement of the closing mechanism separates the sections. In some embodiments, retraction and/or advancement of the elongated closing rod 1311, laterally moves the closing mechanism 1310.

According to some exemplary embodiments, the grasping member is shaped and sized to be positioned and advanced through a working channel of a catheter positioned in the LA. Optionally, the grasping member is shaped and sized to be positioned within a lumen of a cover, for example cover 371 or 374.

According to some exemplary embodiments, for example as shown in FIG. 13B, the grasping member 1302 is shaped and sized to be positioned within a channel 1312 of a tissue inverting element 1316. In some embodiments, the grasping member 1302 is shaped and sized to move within the channel 1312. In some embodiments, the grasping head 1304 is shaped and sized to be positioned within a head of a tissue inverting element, for example vacuum head 1314. In some embodiments, the grasping head is configured to be advanced forward away from the vacuum head 1314, for example to make contact with a portion of the LAA wall. In some embodiments, the grasping head brings the sections closer to each other, for example to hold the portion of the LAA wall. In some embodiments, retraction of the grasping head into the vacuum head while the grasping head hold a portion of the LAA wall brings the portion of the LAA wall into the vacuum head. Optionally, when the portion of the LAA wall is held by vacuum force applied by the vacuum head, the grasping member is retracted, optionally through the channel of the inverting element.

According to some exemplary embodiments, the grasping head comprises at least one protrusion facing the LAA wall, optionally when the sections of the grasping head are spaced apart. In some embodiments, the grasping head comprises at least one distal protrusion facing the tissue. In some embodiments, the sections of the grasping head are configured to be spaced apart to a maximal distance of 50 mm, for example 50 mm, 40 mm, 30 mm or any intermediate smaller or larger distance from each other.

Exemplary Cover with a Sealing Adaptor

Figure 14A:
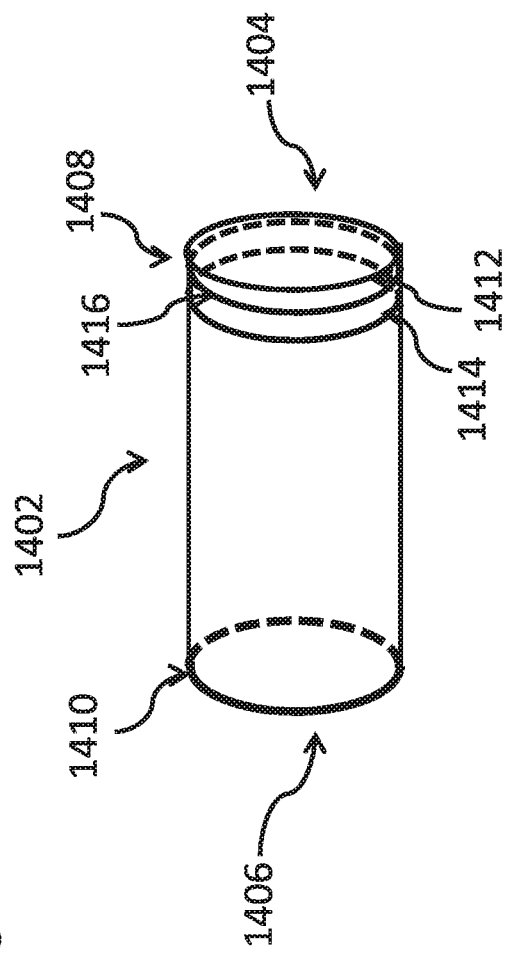
FIG. 14A is a schematic illustration of a cover with a sealing adaptor, according to some embodiments of the invention.

According to some exemplary embodiments, an isolator, for example a cover is used to seal the LAA from the LA. In some embodiments, the cover, for example a mesh is used to seal the LAA from the LA, for example to prevent blood clot and/or tissue debris passage from the LAA into the LA. In some embodiments, a distal opening of the cover is positioned at least partly with the LAA lumen. In some embodiments, in order to form a tight sealing between the external surface of the cover and the internal surface of the LAA opening, a sealing adaptor associated with the distal opening of the cover is configured to adjust at least some dimensions of the distal opening and/or the cover, for example diameter, width. In some embodiments, adjustment of the distal opening and/or the cover allows to position the cover within LAA openings with different shapes and/or dimensions. Reference is now made to FIG. 14A, depicting a cover with a sealing adaptor, according to some exemplary embodiments of the invention.

According to some exemplary embodiments, a cover 1402, optionally a tubular cover, comprising a distal opening 1404 and a proximal opening 1406. In some embodiments, a sealing adaptor 1408 is associated with the cover 1402. Optionally, the sealing adaptor 1408 is associated with the distal opening 1404. In some embodiments, the sealing adaptor is positioned at a distance of up to 20 mm from the distal opening, for example at a distance of 0.5 mm, 1 mm, 5 mm, 10 mm or any intermediate, smaller or larger value. In some embodiments, the sealing adaptor is made from an elastic material, for example rubber and can be fitted to different types or sizes of covers. Alternatively, the sealing adaptor is embedded within a metal web forming the cover or the scaffold of the cover.

According to some exemplary embodiments, the sealing adaptor comprises at least two axially spaced-apart rings, optionally elastic rings, for example a distal ring 1412, a proximal ring 1414 and an intermediate ring, for example intermediate ring 1416 positioned between the proximal ring and the distal ring. In some embodiments, at least some of the rings are configured to contract and expand independently from the rest of the rings. In some embodiments, the intermediate ring 1416 is configured to expand to a maximal expansion width which is smaller in up to 60% from the maximal expansion width of the proximal ring 1414 and/or the distal ring 1412, for example to a maximal expansion width of 10%, 20%, 30% or any intermediate maximal expansion width from the expansion width of one or more of the adjacent rings. In some embodiments, the proximal ring 1414 is configured to expand to a maximal width which is larger in at least 5% from the maximal width of the distal ring 1412, for example to maximal width which is larger in 5%, 10%, 15% or any intermediate, smaller or larger value from the maximal width of the distal ring 1412.

According to some exemplary embodiments, the proximal ring, for example proximal ring 1414 and/or the distal ring, for example distal ring 1412 are configured to expand, for example in a relaxed state, to a maximal diameter of 5 cm, for example 2 cm, 3 cm, 3.5 cm or any intermediate, smaller or larger value. In some embodiments, the intermediate ring is configured to expand, for example in a relaxed state, to a maximal diameter of 4 cm, for example 1 cm, 2 cm, 3 cm or any intermediate, smaller or larger value. In some embodiments, the sealing adaptor 1408 is made from a shape memory alloy, for example Nitinol. In some embodiments, the sealing adaptor 1408 is made from any elastic material.

According to some embodiments, at least one ring associated with the cover, for example cover 1402 is positioned around and on top of the cover. Alternatively, the at least one ring is positioned under the cover. Optionally, the at least one ring is interlaced within the cover. In some embodiments, one or more of the rings comprise a loop, for example a lasso loop. In some embodiments, the lasso loop is an adjustable lasso loop configured to be expanded and/or tightened in response to an external force applied on the loop.

According to some exemplary embodiments, the sealing adaptor is configured to apply force, for example radial force which optionally supports blood sealing up to 20 Newton (N), for example 1N, 2N, 5N, 10N or any intermediate, smaller or larger value against the internal surface of the LAA opening, the internal surface of the LA wall and/or the internal surface of the LAA wall. In some embodiments, the sealing adaptor is made from metal or from a memory shape alloy, for example Nitinol. In some embodiments, the sealing adaptor is associated with the internal surface of the cover, facing the lumen of the cover. Alternatively, the sealing adaptor is associated with external surface of the cover. In some embodiments, the length of the sealing adaptor is in a range of 1-30 mm, for example 1 mm, 3 mm, 5 mm, 10 mm or any intermediate, smaller or larger value.

According to some exemplary embodiments, the cover 1402 comprises at least one ring, for example ring 1410 associated with the proximal opening 1406 of the cover. In some embodiments, the ring 1410 is a metal ring or a lasso ring, configured to contract and close the proximal opening 1406. In some embodiments, the ring 1410 irreversibly closes the proximal opening 1406.

Figure 14B:
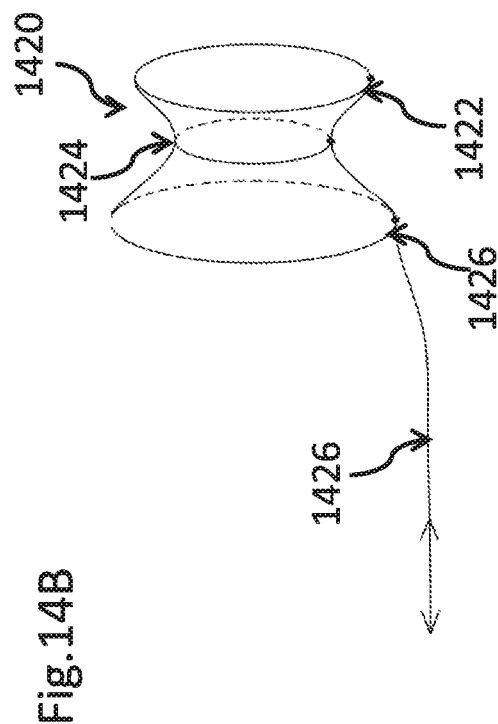
FIG. 14B is a schematic illustration of a sealing adaptor, according to some embodiments of the invention.

According to some exemplary embodiments, for example as shown in FIG. 14B, the sealing adaptor, for example a sealing adaptor 1420 is made from an elastic material, for example a metal web, optionally made from a memory shape alloy, for example Nitinol. In some embodiments, the sealing adaptor comprises at least two spaced apart rings, for example lasso rings or metal rings. In some embodiments, the sealing adaptor 1420 comprises a distal ring 1422, a proximal ring 1426 and one or more intermediate rings, for example ring 1424.

According to some exemplary embodiments, the intermediate ring 1426 is configured to expand to a maximal expansion width which is smaller in up to 60% from the maximal expansion width of the proximal ring 1426 and/or the distal ring 1422, for example to a maximal expansion width of 10%, 20%, 30% or any intermediate maximal expansion width from the expansion width of one or more of the adjacent rings. In some embodiments, the proximal ring 1426 is configured to expand to a maximal width which is larger in at least 5% from the maximal width of the distal ring 1422, for example to maximal width which is larger in 5%, 10%, 15% or any intermediate, smaller or larger percentage from the maximal width of the distal ring 1412.

According to some exemplary embodiments, the proximal ring is shaped and sized to contact at least partly the internal surface of the LA wall. In some embodiments, the distal ring is shaped and sized to contact, at least partly, the internal surface of the LAA wall. Optionally, one or more of the intermediate rings, positioned between the proximal and distal rings are shaped and sized to contact the internal surface of the LAA opening wall. In some embodiments, the one or more intermediate rings expand to a maximal width which is smaller than the maximal expansion width of the distal and/or proximal rings, optionally forming a saddle shape between the distal and proximal rings. In some embodiments, the saddle shape formed between the distal and proximal rings is shaped and sized to be in contact at least partially with the internal surface of the LAA opening wall.

According to some exemplary embodiments, the expansion and/or the contraction of the sealing adaptor, for example sealing adaptor 1420 is controlled by a wire, for example wire 1426, connected to the sealing adaptor. Optionally the sealing adaptor is connected to one or more of the rings of the sealing adaptor. In some embodiments, retraction and/or advancement of the wire 1426 controls the expansion and/or the contraction of the sealing adaptor 1420. In some embodiments, the wire passes through a working channel of a catheter or through a channel of an inverting element.

Exemplary LAA Closure by a Cover with a Sealing Adaptor

Figure 14D:
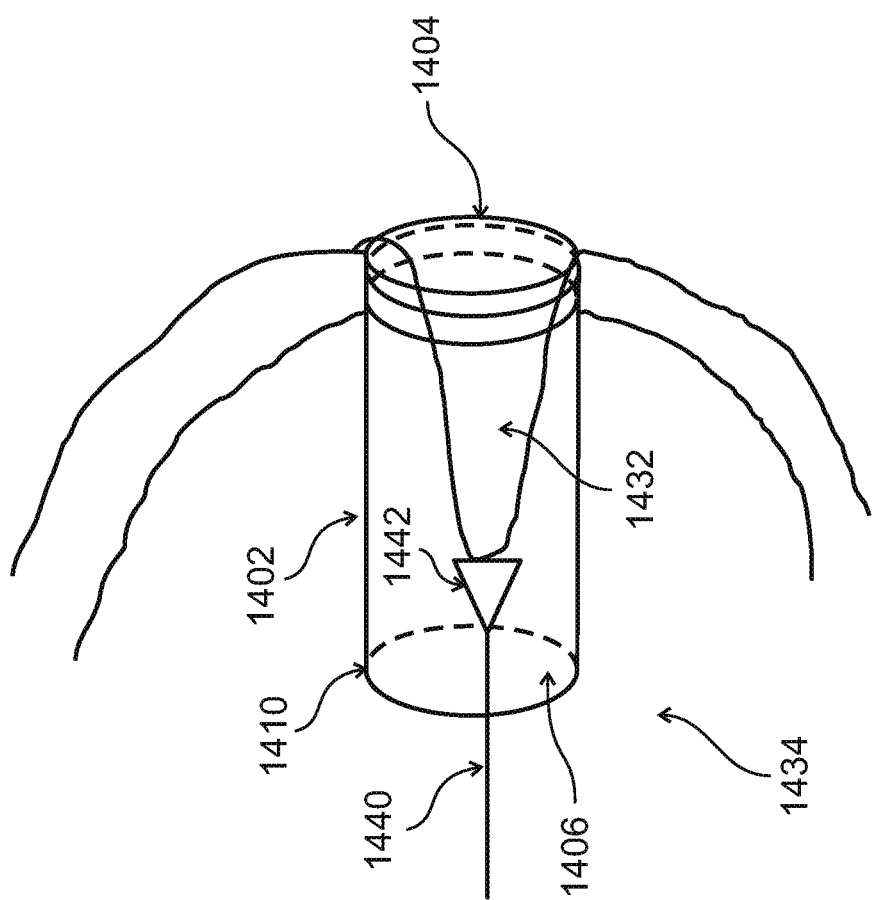
FIG. 14D is a schematic illustration of a portion of the LAA inverted into a cover, according to some embodiments of the invention.
Figure 14E:
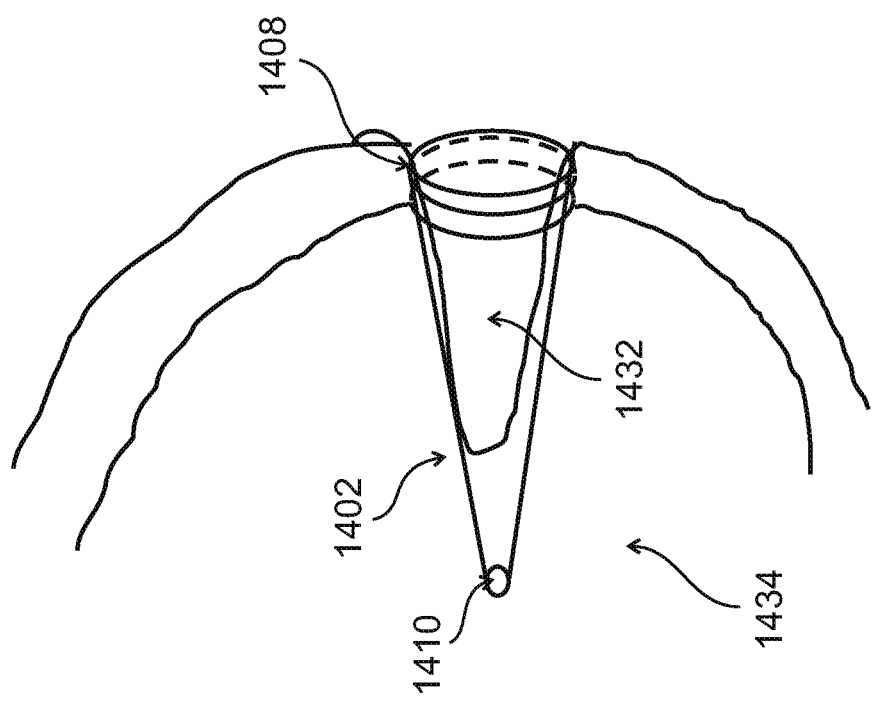
FIG. 14E is a schematic illustration of a cover in a closed conformation where a proximal opening of the cover is closed and a distal opening of the cover is in contact with an inverted portion of the LAA, according to some embodiments of the invention.

Reference is now made to FIGS. 14C-14E depicting sealing and closure of an inverted portion of the LAA by a cover with a sealing adaptor, according to some exemplary embodiments of the invention.

According to some exemplary embodiments, a cover, for example cover 1402 is introduced into the LA 1434. In some embodiments, the cover 1402 is at least partly introduced into the LAA opening 1430. In some embodiments, a sealing adaptor, for example a sealing adaptor 1408 associated with the distal opening of the cover 1402 is positioned at least partly within the LAA opening or within the LA 1432, for example for sealing a passage from the LAA 1432 into the LA 1434. In some embodiments, at least a portion of the sealing adaptor 1408 applies force against the LAA opening wall. Optionally, the force applied by the sealing adaptor attaches the external surface of the cover to the internal surface of the LAA opening wall with power sufficient to seal flow of blood clots and/or debris between the cover and the LAA opening wall. In some embodiments, the sealing adaptor 1408 is configured to attach the cover to LAA openings with varying shapes and sizes.

According to some exemplary embodiments, for example as shown in FIG. 14D, an inverting element 1440 comprising an inverting head, for example a vacuum head 1442 is introduced into the LAA 1432 through a working channel of a catheter, and contacts a portion of the LAA 1432. In some embodiments, the inverting element 1440 inverts the portion of the LAA 1432 through the proximal opening 1404 of the cover into the LA. In some embodiments, the LAA 1432 is inverted at least partly into the lumen of the cover 1402.

According to some exemplary embodiments, for example as shown in FIG. 14E, at least a portion of the sealing adaptor 1408 contracts and is tightened around a base of the inverted LAA 1432, for example, to prevent the release of the inverted LAA from the cover 1402. In some embodiments, the inverting element is retracted through a proximal opening of the cover 1402, and the at least one ring, for example ring 1410 contracts and closes the proximal opening of the cover.

According to some exemplary embodiments, the cover 1402 is formed at least partly from a mesh. In some embodiments, the mesh comprises a metal web, optionally a tubular metal web. In some embodiments, the tubular metal web comprises a plurality of openings larger enough to allow blood flow and smaller enough to prevents passage of cell and tissue debris. In some embodiments the openings width is in a range of 0.1 mm to 25 mm, for example 0.5 mm, 1 mm, 5 mm, 10 mm, 15 mm or any intermediate, smaller or larger value. Optionally, the mesh comprises a woven tube, for example a woven polyester tube associated at least partly with the metal web.

Exemplary Advancement of an Inverting Element into the LAA

Figure 14F:
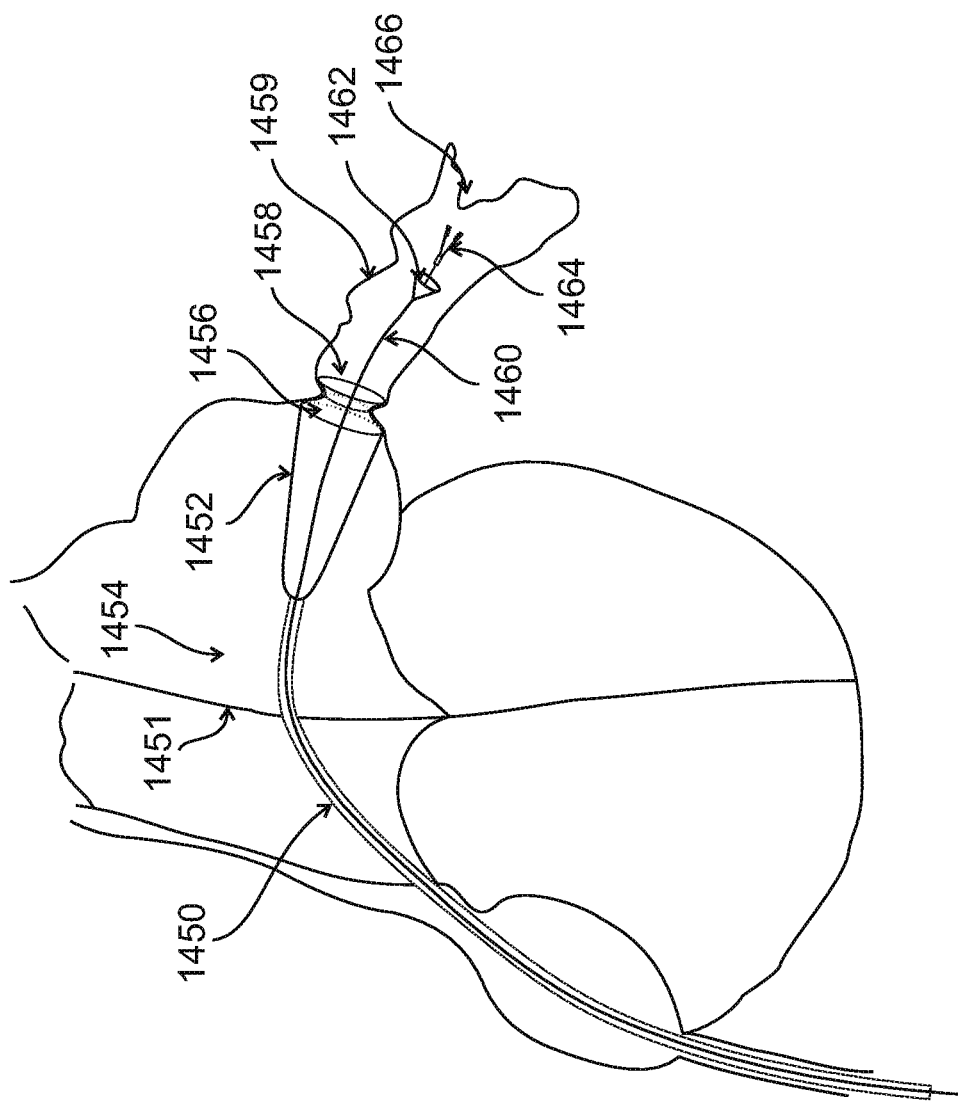
FIG. 14F is a schematic illustration of a cover with a sealing adaptor positioned within the LAA opening during LAA opening, according to some embodiments of the invention.

Reference is now made to FIG. 14F depicting the advancement of an inverting element into the LAA, according to some exemplary embodiments of the invention.

According to some exemplary embodiments, a catheter 1450 is advanced into the LA through an opening in septum 1451. In some embodiments, a cover 1452 is deployed at least partly within the LAA 1459. In some embodiments, a sealing adaptor 1456 associated with the cover 1452, optionally with a proximal opening of the cover 1452 is positioned at least partly within the LAA opening. In some embodiments, the sealing adaptor is configured to re-shape the cover near the proximal opening of the cover according to the shape of the LAA opening, for example to form a tight sealing between the cover and the wall of the LAA opening.

According to some exemplary embodiments, once a tight sealing between the cover and the LAA opening is formed, an inverting element, for example inverting element 1460 is advanced into the LAA 1459. In some embodiments, an inverting head at a distal end of the inverting element 1460, for example vacuum head 1462 is advanced into the LAA, for example to hold a portion of the LAA wall optionally using vacuum forces. Alternatively or additionally, a grasping member with a grasping head 1464 is advanced into the LAA, optionally within a channel of the inverting element 1460, for example to contact and grasp a portion of the LAA wall 1466.

Exemplary Mesh Cover with a Sealing Adaptor

Figure 15:
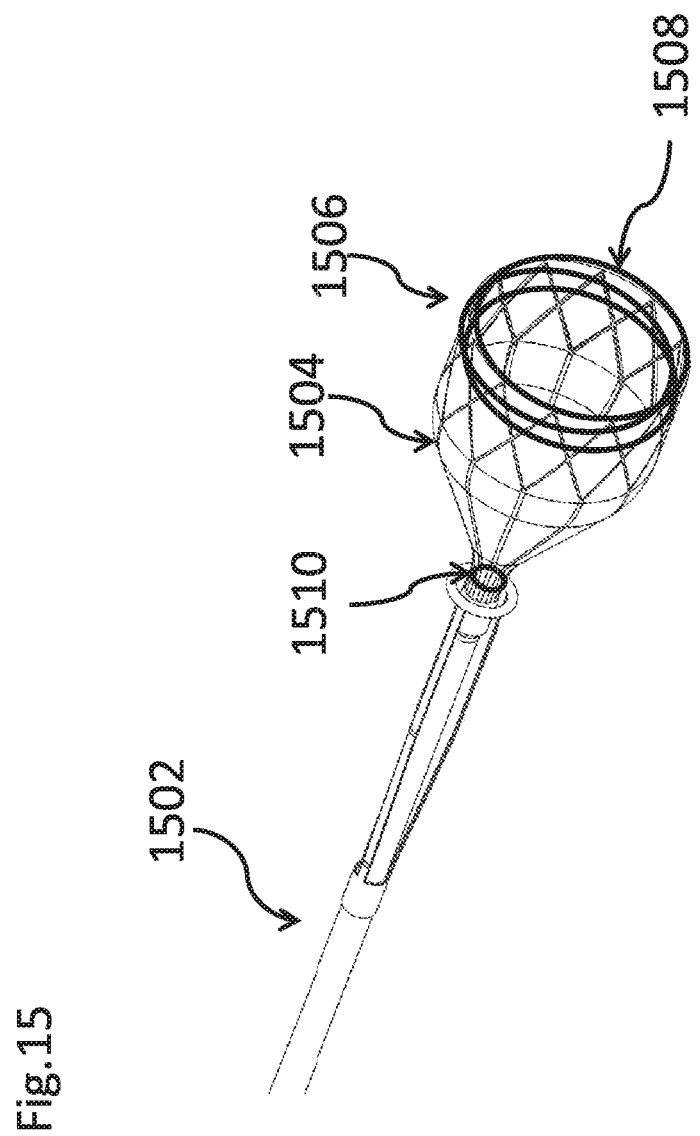
FIG. 15 is a schematic illustration of a catheter device with a mesh cover having a sealing adaptor, according to some embodiments of the invention.

Reference is now made to FIG. 15 depicting a mesh cover with a sealing adaptor, according to some exemplary embodiments of the invention.

According to some exemplary embodiments, a mesh cover, for example mesh cover 1504 is deployed from a lumen of a catheter, for example catheter 1502. In some embodiments, the mesh cover 1504 comprises a sealing adaptor 1506 associated with the mesh cover 1504, optionally near a distal opening of the 1508 of the mesh cover. Alternatively, the sealing adaptor 1506 is associated with the proximal opening 1508. According to some exemplary embodiments, the sealing adaptor 1506 is configured to reshape the mesh cover 1504 around the proximal opening 1508, optionally according to a shape and size of an LAA opening. In some embodiments, the sealing adaptor 1506 is configured to reshape the mesh cover 1504, for example to form a tight sealing between the mesh cover and the wall of the LAA opening, optionally to prevent passage of blood clots and/or debris from the LAA lumen into the LA between the cover and the LAA opening wall.

According to some exemplary embodiments, the mesh cover 1504 comprises at least one ring 1510, for example a metal ring or a lasso for closing a proximal opening of the mesh cover. In some embodiments, the mesh cover 1504 comprises a metal web, optionally a tubular metal web. In some embodiments, the tubular metal web comprises a plurality of openings larger enough to allow blood flow and smaller enough to prevents passage of blood clots and/or cells and tissue debris. In some embodiments the openings width is in a range of 0.1 mm to 25 mm, for example 0.5 mm, 1 mm, 5 mm, 10 mm, 15 mm or any intermediate, smaller or larger value. Optionally, the mesh comprises a woven tube, for example a woven polyester tube associated at least partly with the metal web.

Exemplary Activation Process of a Device for Closing the LAA

Reference is now made to FIG. 16, depicting an activation process of a device for closing the LAA, according to some exemplary embodiments of the invention.

According to some exemplary embodiments, a catheter is introduced into the LA at 1602. In some embodiments, the catheter is introduced from the right atrium through an opening in the septum between the atria into the LA.

According to some exemplary embodiments, a portion of the cover is positioned in the LAA at 1604. In some embodiments, a cover is delivered through a working channel of the catheter into the LA. In some embodiments, the catheter is deployed at least partly within the LA. In some embodiments, for example as shown in FIG. 14F, a portion of the cover is positioned within the LAA opening. In some embodiments, the portion of the cover positioned within the LAA opening comprises a sealing adaptor, for example a two-state sealing adaptor. In some embodiments, the sealing adaptor, for example sealing adaptor 1408 shown in FIGS. 14A-14E, or sealing adaptor 1506 shown in FIG. 15 positioned at least partly within the LAA opening is an integral part of the cover. Alternatively, the sealing adaptor, for example sealing adaptor 1420 is a structure shaped and sized to fit to a variety of covers.

According to some exemplary embodiments, the cover comprises a mesh, for example as shown in FIGS. 11A-11D. In some embodiments, the mesh comprises a metal web, optionally a tubular metal web. In some embodiments, the tubular metal web comprises a plurality of openings larger enough to allow blood flow and smaller enough to prevents passage of cell and tissue debris. In some embodiments the openings width is in a range of 0.1 mm to 25 mm, for example 0.5 mm, 1 mm, 5 mm, 10 mm, 15 mm or any intermediate, smaller or larger value. Optionally, the mesh comprises a woven tube, for example a woven polyester tube associated at least partly with the metal web.

According to some exemplary embodiments, a portion of the cover applies force against the LAA wall at 1606. In some embodiments, the portion of the cover positioned within the LAA opening applies force against the LAA opening wall, for example to prevent leakage of blood clots and/or cell debris between the cover and the LAA opening wall. In some embodiments, the portion of the cover applying force against the LAA opening wall comprises the sealing adaptor. Alternatively, the sealing adaptor is associated with the cover. In some embodiments, the force applied by a portion of the cover on the LAA wall is sufficient to fix the cover to the LAA open wall, for example to stabilize the attachment of the cover to the LAA wall.

According to some exemplary embodiments, LAA content is removed at 1608. In some embodiments, the LAA content comprising blood clots and/or cell or tissue debris is removed at 1608, optionally by a tissue inverting element generating negative pressure within the LAA. In some embodiments, the tissue inverting element comprising a vacuum head is introduced into the LAA, for example to remove the LAA content through a vacuum channel of the tissue inverting element passing within the working channel of the catheter. Additionally, the tissue inverting element is introduced into the LAA through a proximal opening of the cover, and through a distal opening of the cover, for example as shown in FIG. 14F.

According to some exemplary embodiments, the LAA is at least partly inverted into the LA at 1610. In some embodiments, an inverting head of the element, for example vacuum head 566 shown in FIG. 6E, contacts a portion of the LAA wall, optionally using vacuum forces. In some embodiments, the inverting element is retracted, for example into the working channel of the catheter, while inverting at least partly the LAA wall. In some embodiments, retraction of the inverting element inverts at least partly the LAA into the LA. Alternatively, at least 90% of the LAA wall is inverted into the LA, for example 90%, 92%, 97% or any intermediate, smaller or larger percentage of the LAA wall is inverted into the LA.

According to some exemplary embodiments, the LAA is at least partly inverted into the cover at 1612. In some embodiments, the LAA is at least partly inverted through a distal opening of the cover, for example as shown in FIG. 14D. In some embodiments, at least 90% of the LAA wall is inverted into the LA, for example 90%, 92%, 97% or any intermediate, smaller or larger percentage of the LAA wall is inverted into the LA.

According to some exemplary embodiments, the cover applies force on the inverted LAA at 1614. In some embodiments, the sealing adaptor contracts and applies force on part of the inverted LAA wall. In some embodiments, the sealing adaptor contracts following a manipulation of the sealing adaptor for example using a wire or a string connected to at least part of the sealing adaptor. Optionally, the wire or the string is retracted or pulled to contract the sealing adaptor on the inverted LAA. In some embodiments, the contraction of the sealing adaptor on the LAA is an irreversible contraction. In some embodiments, the sealing adaptor comprises at least one pin or needle facing outwards for contacting the LAA wall or LAA opening wall when attaching the cover to the LAA wall or LAA opening wall respectively. Alternatively or additionally, the sealing adaptor comprises at least one pin or needle facing inwards, for example to contact the inverted LAA.

According to some exemplary embodiments, the catheter is disconnected from the cover at 1616. In some embodiments, the catheter disconnects from the cover, and is retracted away from the heart, for example as shown in FIG. 6G. In some embodiments, when the catheter is retracted, a proximal opening of the cover is closed. In some embodiments, the proximal opening is closed by a ring or lasso associated with the proximal opening. In some embodiments, the ring or the lasso is manipulated prior to disconnection of the catheter from the cover, for example to irreversible close the proximal opening. Alternatively, a ring or a lasso associated with the proximal opening are tightened when the catheter is disconnected from the cover. In some embodiments, the cover around the proximal opening is shaped and sized, for example using a shape memory alloy optionally Nitinol, to collapse and close the proximal opening when the catheter is disconnected from the cover.

According to some exemplary embodiments, the cover collapses on the inverted LAA at 1618. In some embodiments, the cover optionally made from a shape memory alloy contracts on the inverted LAA portion positioned within the cover. In some embodiments, the cover contracts and reshapes the LAA portion positioned within the cover. In some embodiments, the cover contracts into a disc-shaped structure, for example as shown in FIG. 7B.

According to some exemplary embodiments, the cover attaches the inverted LAA to the LA wall at 1620. In some embodiments, the cover, optionally made at least partly from a shape memory alloy contracts into a pre-formed disc attaching the inverted LAA to the LA wall, for example as shown in FIG. 7C. In some embodiments, the cover attaches the inverted LAA to the LA wall, for example to reduce the volume of the inverted LAA within the LA.

It is expected that during the life of a patent maturing from this application many relevant methods and devices to cover the LAA will be developed; the scope of the term cover is intended to include all such new technologies a priori. As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A left atrial appendage (LAA) isolator system, comprising:
a catheter having a lumen, wherein said catheter is insertable via blood vessels into said left atrium (LA) of a subject;
an isolator extendable from said catheter lumen into said LA and having an inner lumen with a proximal opening facing said catheter and a distal opening large enough to at least match an opening of an LAA, and configured to prevent at least clots from exiting said LAA into said LA;
a LAA manipulation tool configured to at least partially invert a portion of said LAA into said LA and into said isolator by grasping a LAA wall;
wherein said isolator comprises a fastener attached to a circumference of the isolator,
wherein said fastener is configured to be fastened around said inverted portion of said LAA, and wherein said isolator is configured to detach from said system and to be attached to said inverted portion of said LAA.

2. A system according to claim 1, wherein said isolator is porous.

3. A system according to claim 1, wherein said isolator is configured to detach from said system and collapse or be collapsed on said inverted LAA portion.

4. A system according to claim 1, wherein said isolator comprises a porous mesh forming a web shaped structure with openings having a maximal dimension of up to 200 microns.

5. A system according to claim 4, wherein said porous mesh is formed from a memory shape alloy.

6. The system of claim 1, wherein said fastener surrounds said distal opening of said isolator.

7. The system of claim 1, wherein said fastener comprises at least one of a ring, a loop, a wire or a clip.

8. The system according to claim 1, wherein said LAA manipulation tool comprises a vacuum catheter configured to apply vacuum through said isolator on a wall of said LAA.

9. The system according to claim 1, wherein said LAA manipulation tool is configured to at least partially invert said portion of said LAA into said LA and into said isolator without penetrating through the LAA wall.

10. A method for reshaping a left atrial appendage (LAA), comprising:
inverting at least one section of said LAA at least partly into a left atrium (LA);
fastening a fastener around said inverted at least one section, wherein said fastener is attached to a circumference of a cover delivered to said LA by a catheter;
attaching said cover to said inverted at least one section; and
detaching said cover from said catheter.

11. The method of claim 10, comprising:
isolating said LAA from said LA before said inverting.

12. A method for closing an atrial appendage, comprising:
navigating a catheter through blood vessels into an atrium;
isolating said atrial appendage from said atrium to prevent a release of blood clots from said atrial appendage into said atrium by extending an isolator from said catheter into said atrium, wherein said isolator comprises a fastener attached to a circumference of said isolator;
inverting at least a portion of said atrial appendage into said atrium and into said expandable isolator by grasping a wall of said atrial appendage;
placing said fastener of said isolator around a section of said atrial appendage; and
fastening said fastener around said section of said atrial appendage, wherein fastening said fastener attaches said isolator to said inverted portion of said atrial appendage;
detaching said isolator from said catheter.

13. The method of claim 12, wherein said atrium is a left atrium (LA), and wherein said atrial appendage comprises a left atrial appendage (LAA).

14. The method of claim 13, wherein said placing comprising:
advancing said fastener to a desired location on said LAA before said fastening.

15. The method of claim 13, further comprising anchoring said fastener to said section of said LAA.

16. The method of claim 13, wherein said isolating comprises placing said isolator at least partially within said LAA or in contact with a wall of said LA around an opening of said LAA.

17. The method of claim 13, wherein said placing comprises placing said fastener around said inverted portion of said LAA.

18. The method of claim 17, wherein said inverting comprises applying a vacuum on said wall of said LAA sufficient to invert said portion of said LAA.

19. The method of claim 12, wherein said inverting comprises inverting said at least a portion of said atrial appendage into said atrium and into said expandable isolator without penetrating through the atrial appendage wall.

* * * * *